United States Patent [19]

Carceller et al.

[11] Patent Number: 4,997,843
[45] Date of Patent: Mar. 5, 1991

[54] 2,4-DISUBSTITUTED DERIVATIVES OF TETRAHYDROFURAN USEFUL FOR THE TREATMENT OF PAF MEDIATED ILLNESSES

[75] Inventors: Elena Carceller; Javier Bartroli, both of Barcelona, Spain

[73] Assignee: J Uriach & Cia S.A., Spain

[21] Appl. No.: 257,205

[22] Filed: Oct. 13, 1988

[30] Foreign Application Priority Data

Oct. 13, 1987 [ES] Spain .................................. 8702900
Jul. 19, 1988 [ES] Spain .................................. 8802276

[51] Int. Cl.$^5$ ..................... A61K 31/44; C07D 405/12
[52] U.S. Cl. .................................... 514/336; 546/283; 548/147; 548/204
[58] Field of Search .................... 546/283; 514/336

[56] References Cited

U.S. PATENT DOCUMENTS 4,766,132 8/1988 Kay ..................................... 514/332

OTHER PUBLICATIONS

Roubin et al. in "Lymphokines" Ed E. Pick, Acad. Press, New York, p. 249, 1983.
Vargaftig et al., *Ann. NY Acad. Sci.* 1981, 370, 119.
Pinckard et al., *Int. Arch. Allergy Appl. Immun.*, 1981, 66, 127.
Benveniste et al., *J. Exp. Med.*, 1972, 136.
Mazzoni et al., Proc. Physiol. Soc. Univ. Coll. Meet., Mar. 1985.
Blank et al., *Biochem. Biophys. Res. Commun.*, 1979, 90, 1194.
Feuerstein, et al., *Circul. Shock*, 1984, 13, 255.
Muirhead et al., *Hypertension*, 1981, 3, 107.
Otsuka et al., *J. Exp. Med.*, 1972, 136, 1356.
Nishihira et al., *Tohoku J. Exp. Med.*, 1985, 147, 145.
Norris et al., *JACS* 1933, 55, 4697.
Coppinger et al., *J. Am. Chem. Soc.*, 76 1372, 1954.

*Primary Examiner*—Alan L. Rotman
*Attorney, Agent, or Firm*—Rothwell, Figg, Ernst & Kurz

[57] ABSTRACT

The present invention describes novel 2,4-disubstituted derivatives of tetrahydrofuran, having the formula I

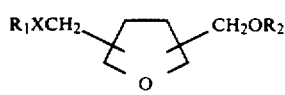

wherein: -X- is either an oxygen atom or a covalent single bond; —$CH_2XR_1$ group is in the position 2 and —$CH_2OR_2$ is in the position 4 of the tetrahydrofuran ring, or —$CH_2XR_1$ is in position 4 and —$CH_2OR_2$ in position 2; -$R_1$ represents an alkyl or an alkylaminocarbonyl group; -$R_2$ represents a group having the formula -Y-$(CH_2)_n$-Q.$(A^-)_q$ where -Y- is a covalent single bond, a carbonyl group, a carbonyloxy group or a carbonylamino group; n is an integer 0 to 10; Q is a nitrogen containing heterocycle; q is one when Q is charged or q zero when Q is neutral; and $A^-$ is a pharmaceutically acceptable anion. These compounds are PAF antagonists and, thus, useful for the treatment of diseases in which PAF is involved.

7 Claims, No Drawings

2,4-DISUBSTITUTED DERIVATIVES OF TETRAHYDROFURAN USEFUL FOR THE TREATMENT OF PAF MEDIATED ILLNESSES

FIELD OF THE INVENTION

The present invention relates to new 2,4-disubstituted derivatives of tetrahydrofuran with a potent antagonist activity of the platelet activating factor (PAF), together with a process for their preparation. The invention also applies to the pharmaceutical preparations which contain these compounds, and their use in the treatment of diseases in which PAF is involved, such as allergic and bronchial asthma, platelet aggregation disorders, septic shock, hypertension, etc.

BRIEF DESCRIPTION OF THE PRIOR ART

Platelet activating factor (PAF), or (1-O-alkyl-2-acetyl-sn-glyceryl-3-phosphorylcholine), also called acetyl glyceryl ether phosphorylcholine (AGEPC) or PAF-acether is a natural phospholipid synthesized by different cells (basophiles, macrophages, neutrophiles, platelets) and tissues (heart, lung and kidney) of the organism. (Roubin et al. in "Lymphokines" Ed. E. Pick, Acad. Press. New York, p. 249, 1983; Vargaftig et al., *Ann. N.Y. Acad. Sci.*, 1981, 370, 119; Pinckard et al., *Int. Arch. Allergy Appl. Immun.*, 1981, 66, 127.

PAF was described for the first time as a potent platelet aggregating agent (Benveniste et al., *J. Exp. Med.*, 1972, 136) and later it was demonstrated that it had other biological activities in vivo such as peripheral vasodilatation, increase of the vascular permeability, induction of bronchoconstriction and hyperreactivity of the respiratory tract (Mazzoni et al., Proc. Physiol. Soc. Univ. Coll. Meet., March 1985). PAF also produces immediate hypotension followed by pulmonary and renal hypertension in rats (Blank et al., *Biochem. Biophys. Res. Commun.*, 1979, 90, 1194), guinea pigs (Feuerstein, et al., *Circul. Shock*, 1984, 13, 255), rabbits (Muirhead et al., *Hypertension*, 1981, 3, 107) and dogs (Otsuka et al., *J. Exp. Med.*, 1972, 136, 1356), and it has been rated as the most potent ulcerogenic agent described until now.

Consequently, PAF is a mediator that is implicated in a large set of pathological processes such as asthma, septic shock, transplant rejection, thrombosis, ulceration, inflammation and renal diseases.

Even though its mechanism of action is still not known with precision, some studies show that the biological activities of PAF involve the existence of a specific receptor. Recently, it has been possible the isolation of one of these receptors from human platelets and it has been identified as a protein with a molecular weight of 160.000 daltons (Nishihira et al., *Tohoku J. Exp. Med.*, 1985, 147, 145). On the other hand, the capacity to inhibit the binding of $^3$H-PAF to their receptors is well correlated with the amount of PAF needed to provoke the in vitro and in vivo observed effects. These facts indicate that the compounds that act as specific antagonists of PAF could result of interest for the treatment of all those pathological processes related directly or indirectly with PAF.

Several PAF analogues have been examined with the pourpose to find compounds with the above mentioned antagonist activity and some of them are known as PAF antagonist, for example, the compounds described in patent Nos. EP 147768, EP 146258, EP 138559, EP 157609, JP 57/165394, JP 58/133116, JP 58/35116, EP 0209239, EP 0146258, WO 86/01507, EP 0210804, EP 0178261 among others.

The new compounds of the present invention, not only are structurally different from any of the compounds described in the above mentioned prior art, but also —and surprisingly— show a remarkable PAF antagonist activity. In fact, never before 2,4-disubstituted derivatives of tetrahydrofuran have been used as PAF antagonist substances.

DESCRIPTION OF THE INVENTION

The present invention relates to 2,4-disubstituted derivatives of tetrahydrofuran, having the general formula I

wherein:
—X— is either an oxygen atom or a covalent single bond;
either the —CH$_2$XR$_1$ group is in position 2 and the —CH$_2$OR$_2$ group is in position 4 of the tetrahydrofuran ring,
or the —CH$_2$XR$_1$ group is in position 4 and the —CH$_2$OR$_2$ group is in position 2;
either —R$_1$ is a linear or branched alkyl, alkenyl or alkynyl group, of 10 to 24 carbon atoms,
or —R$_1$ is a group having the formula —CO—NR$_3$R$_4$ and X=oxygen, where R$_3$ represents a linear or branched alkyl, alkenyl or alkynyl group of 10 to 24 carbon atoms, and R$_4$ is hydrogen, C$_1$-C$_4$ alkyl, C$_1$-C$_4$ acyl, haloacetyl or C$_1$-C$_4$ alcoxycarbonyl;
—R$_2$ represents a group having the formula —Y—(CH$_2$)$_n$—Q.(A$^-$)q, where
—Y— is a single covalent bond or one of the following groups: —C(=O)—, —C(=O)O— or —C(=O)NR$_4$—;
n is an integer from 0 to 10;
—Q is
either a neutral heterocycle group containing a non-quaternary nitrogen atom and connected to the alkylene chain by a ring carbon (in which case —Q is represented by —Q' and q=0);
or said —Q is the same radical Q' but quaternized (in which case —Q is represented by —Q''$^{(+)}$ and q=1);
or said —Q is a heterocyclic group connected to the alkylene chain by a quaternary nitrogen (in which case —Q is represented by —Q'''$^{(+)}$ and q=1);
—Q may optionally contain further nitrogen atoms, one or more oxygen or sulfur atoms, and may be substituted by one or several C$_1$-C$_6$ alkyl, C$_1$-C$_6$ alkyloxy, carbanoyl, C$_1$-C$_6$ hydroxyalkyl or halogen groups;
A$^-$ is a pharmaceutically acceptable anion such as halide (chloride, bromide or iodide), C$_1$-C$_{10}$ alkylsulfonate, arylsulfonate or carboxylate;
The title compounds I have at least two asymmetric carbons that can produce stereoisomers. The present invention includes these stereoisomers as well as their mixtures.

Although the present invention includes all the above mentioned compounds, the following compounds are specially preferred:

Those in which $-R_1$ is a linear alkyl chain of 13 to 18 carbon atoms or a $-(C_{12}-C_{18}\text{ alkyl})-NHC(=O)-$ group; those in which $-R_2$ is a group having the formula $-Y-(CH_2)_n-Q'''^{(+)}.A^{(-)}$ where $-Y-$ is a single covalent bond or a $-C(=O)-$ group, n is an integer from 4 to 8, and $Q'''^{(+)}$ is an aromatic heterocyclic cation radical, connected directly to the alkylene chain by the quaternary nitrogen of the ring, specially those in which $Q'''^{(+)}$ is thiazolium and $A^-$ is the anion previously described; those in which $-R_2$ is a group of formula $-Y-(CH_2)_n-Q''^{(+)}.A^{(-)}$ where $-Y-$ is a $-C(=O)NR_4-$, $-R_4$ is an acetyl group, n is 2, 1 or 0, and $Q''^{(+)}$ is an aromatic heterocyclic cation radical, specially those containing a quaternary nitrogen that belongs to the ring but is not connected directly to the alkylene chain $-Y-(CH_2)_n-$, and more specially those in which $-Q''^{(+)}$ is 1-($C_1-C_3$ alkyl)-2-pyridinium.

The specific compounds whose formulas are represented below, together with the number corresponding to the example in which their preparation is described, are still more preferred.

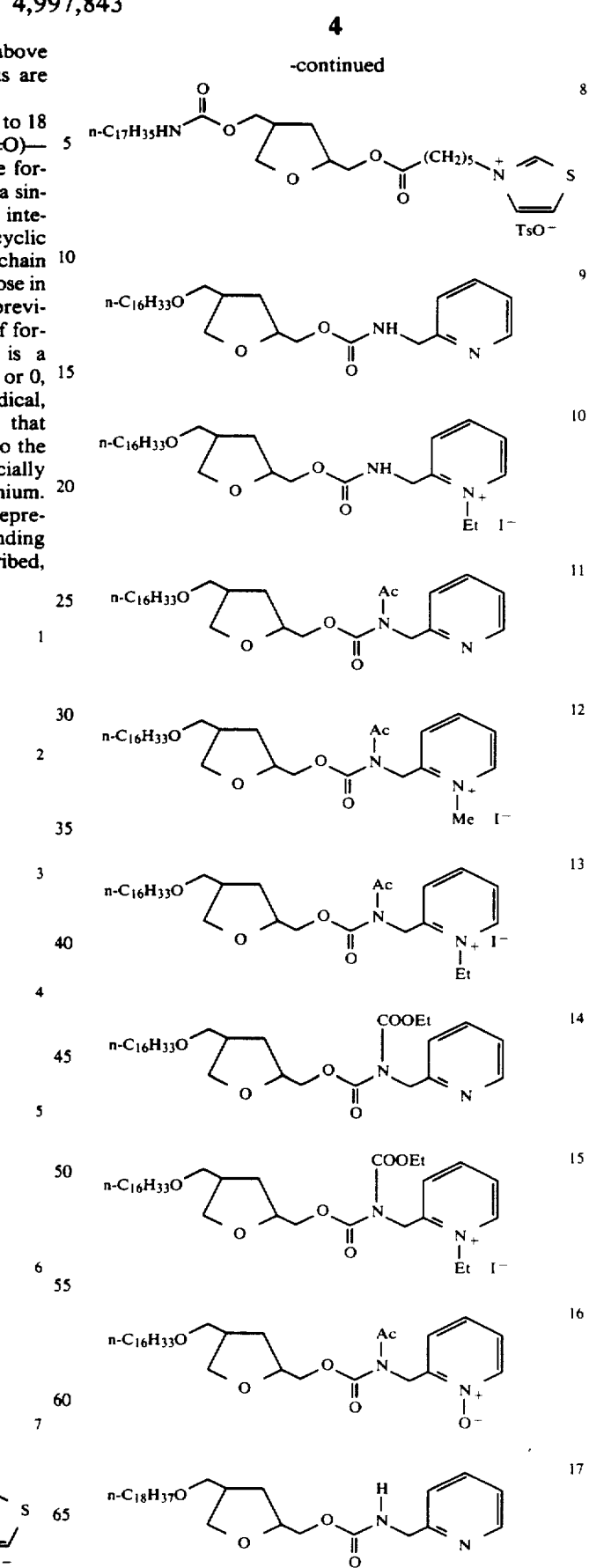

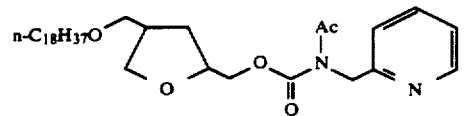
18
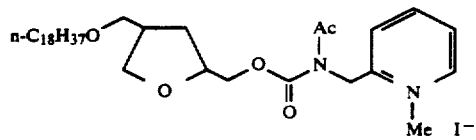
19
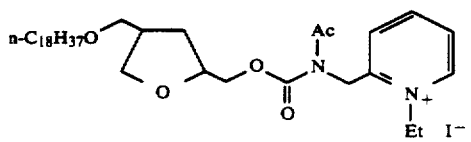
20
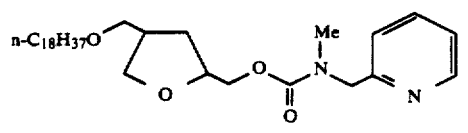
21
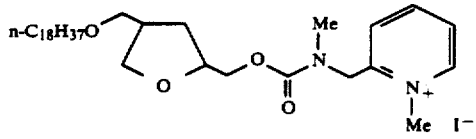
22
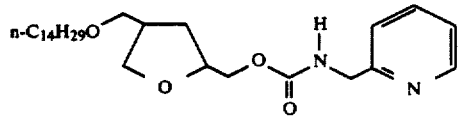
23
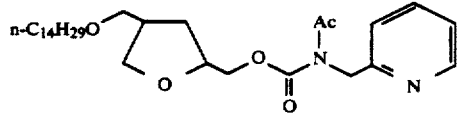
24
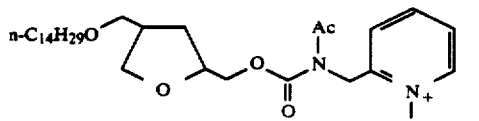
25
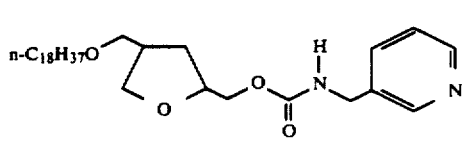
26
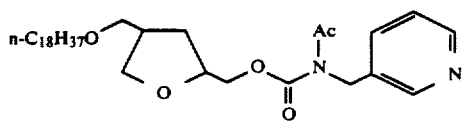
27
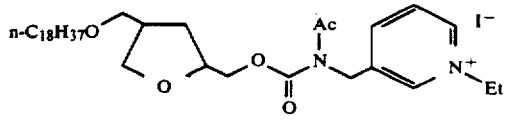
28
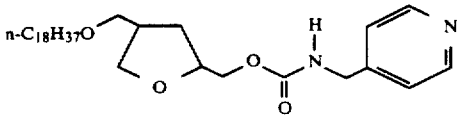
29
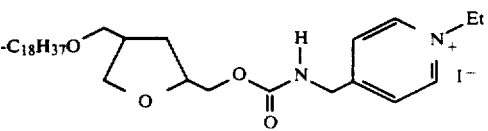
30
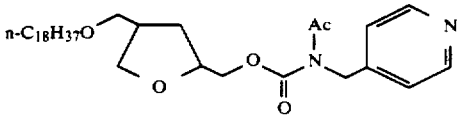
31
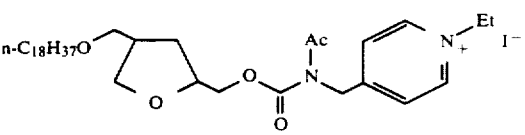
32
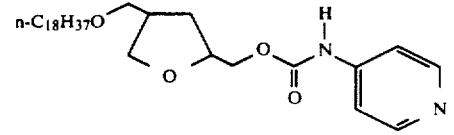
33
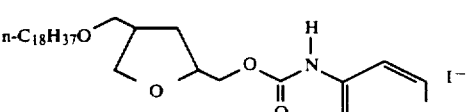
34
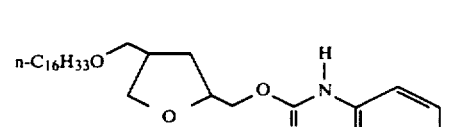
35
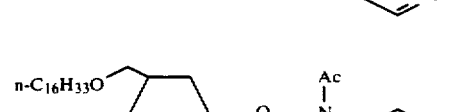
36
37
38
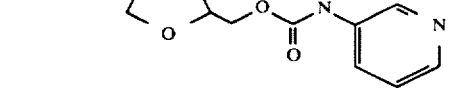

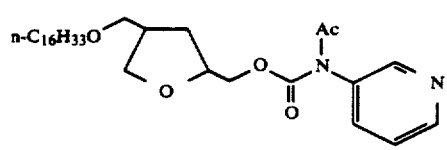
39
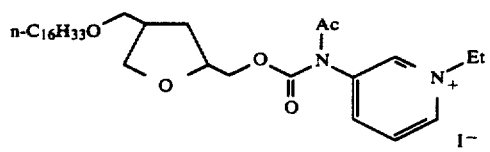
40
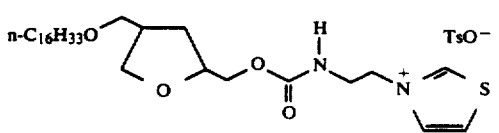
41
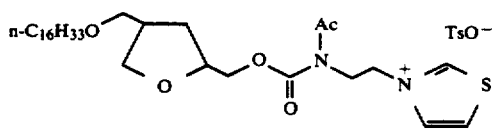
42
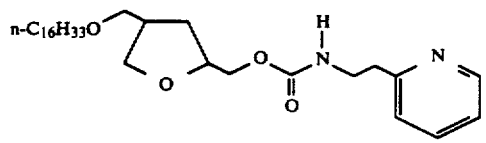
43
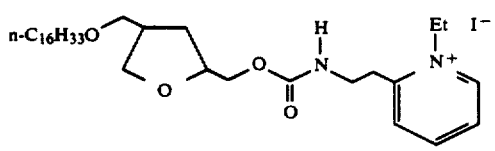
44
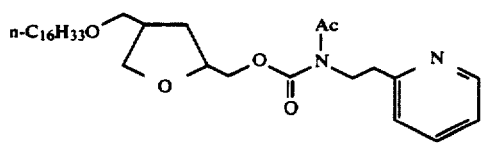
45
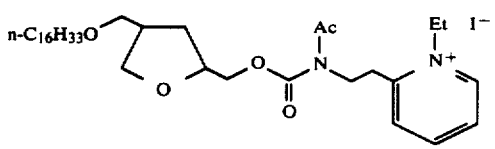
46
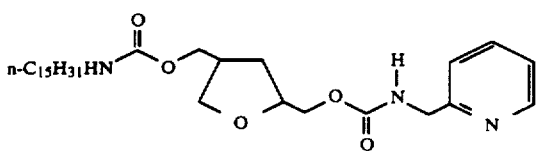
47
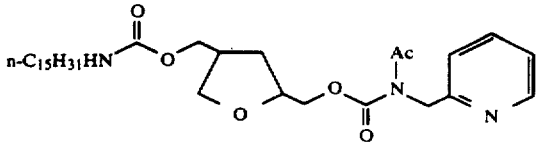
48
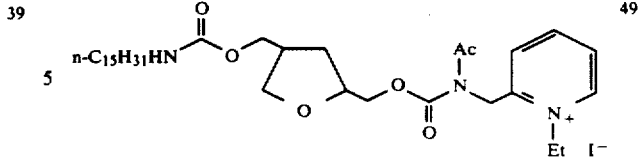
49
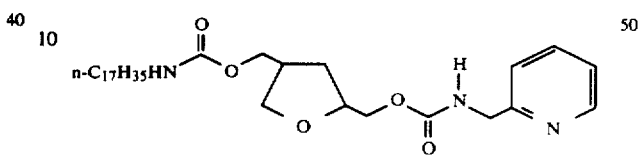
50
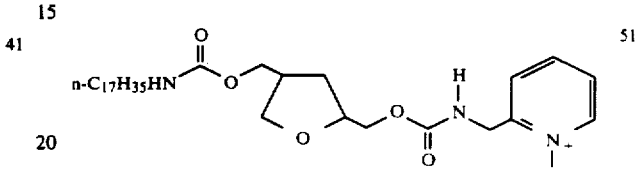
51
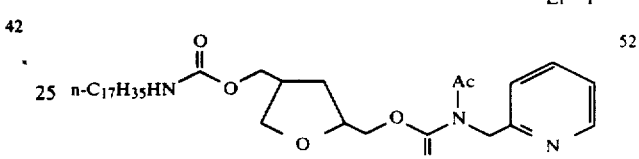
52
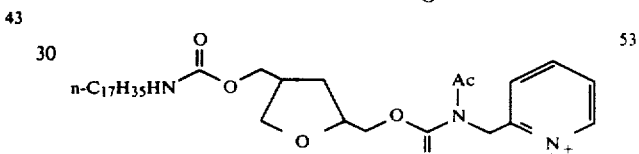
53
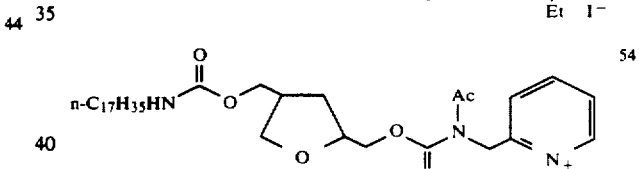
54
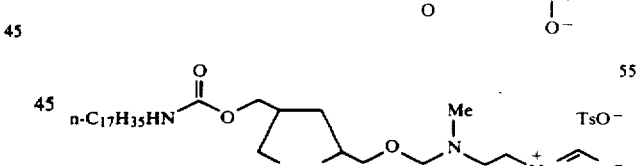
55
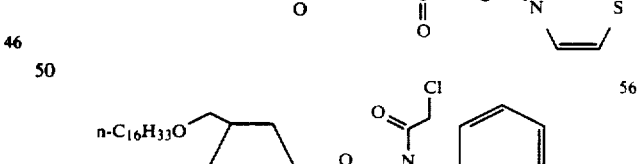
56
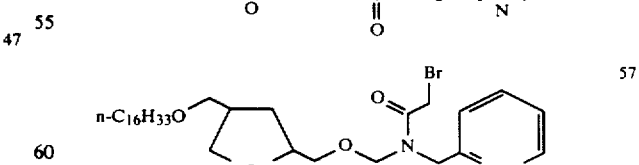
57
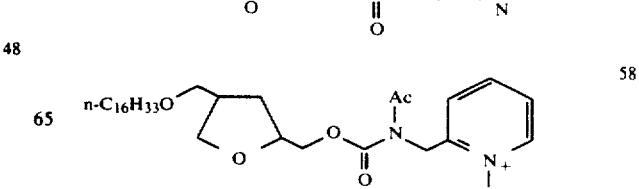
58

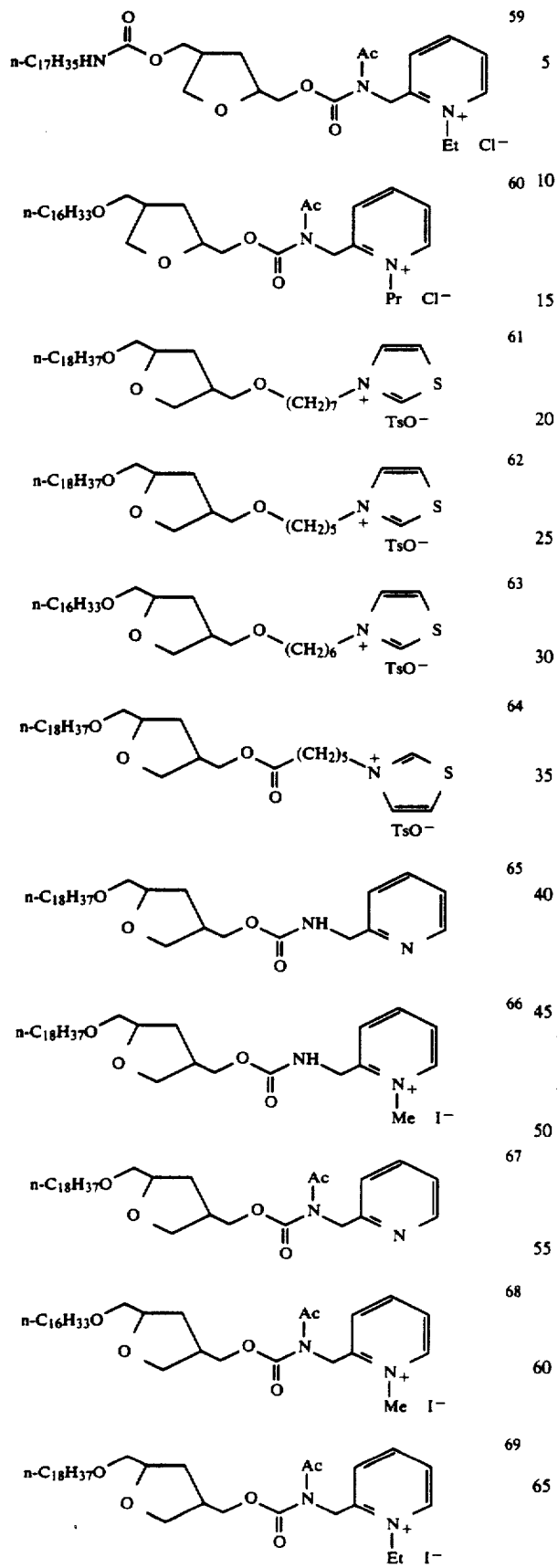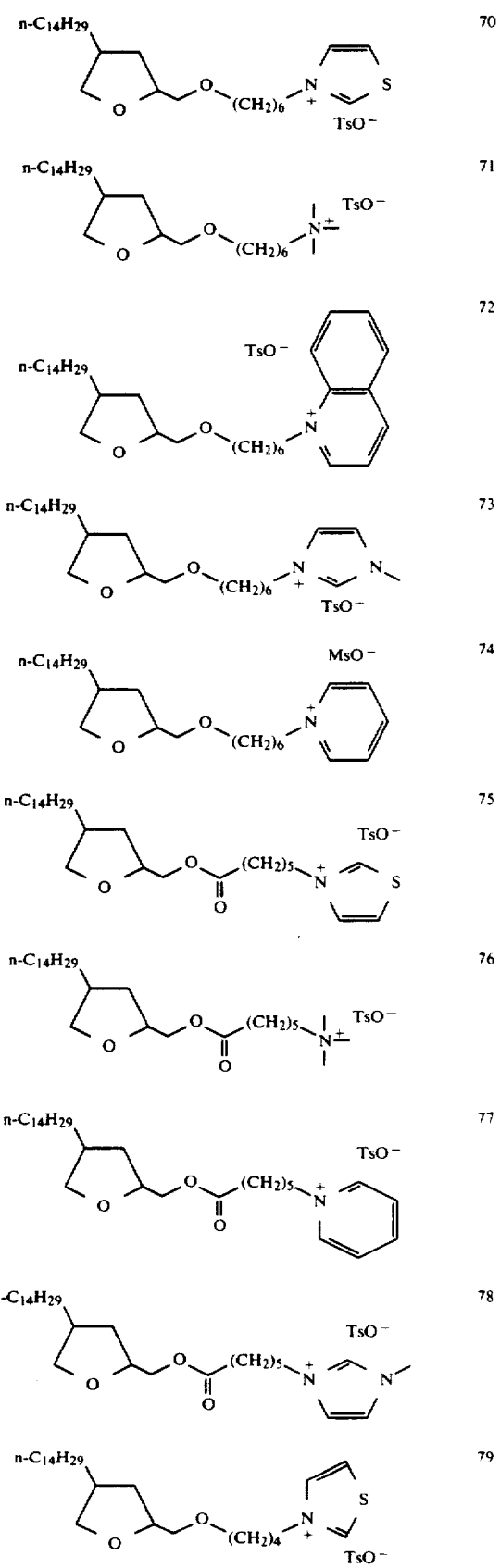

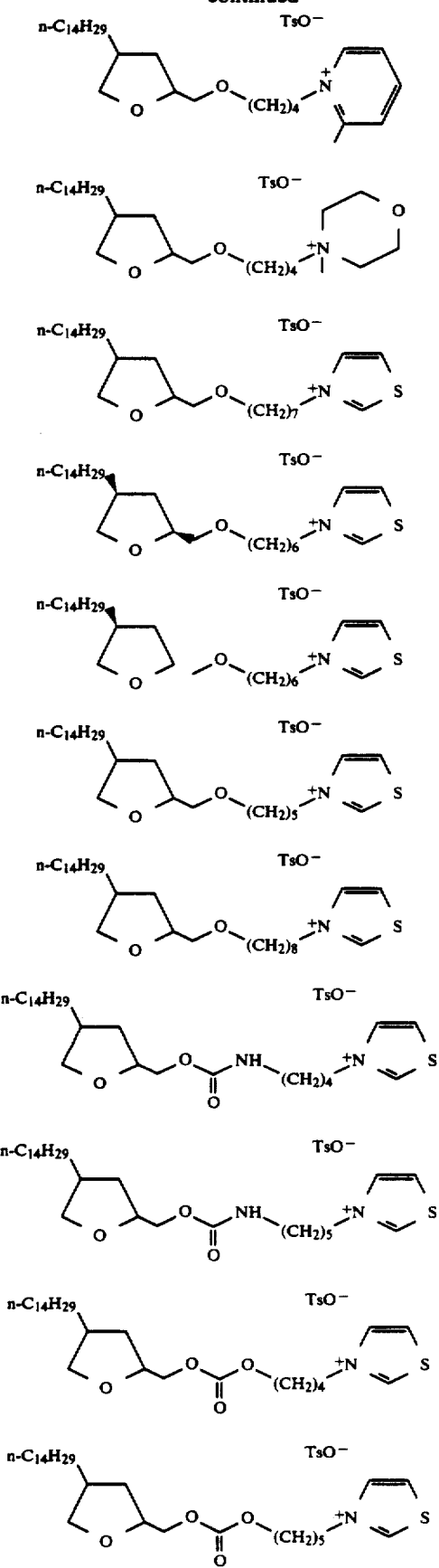
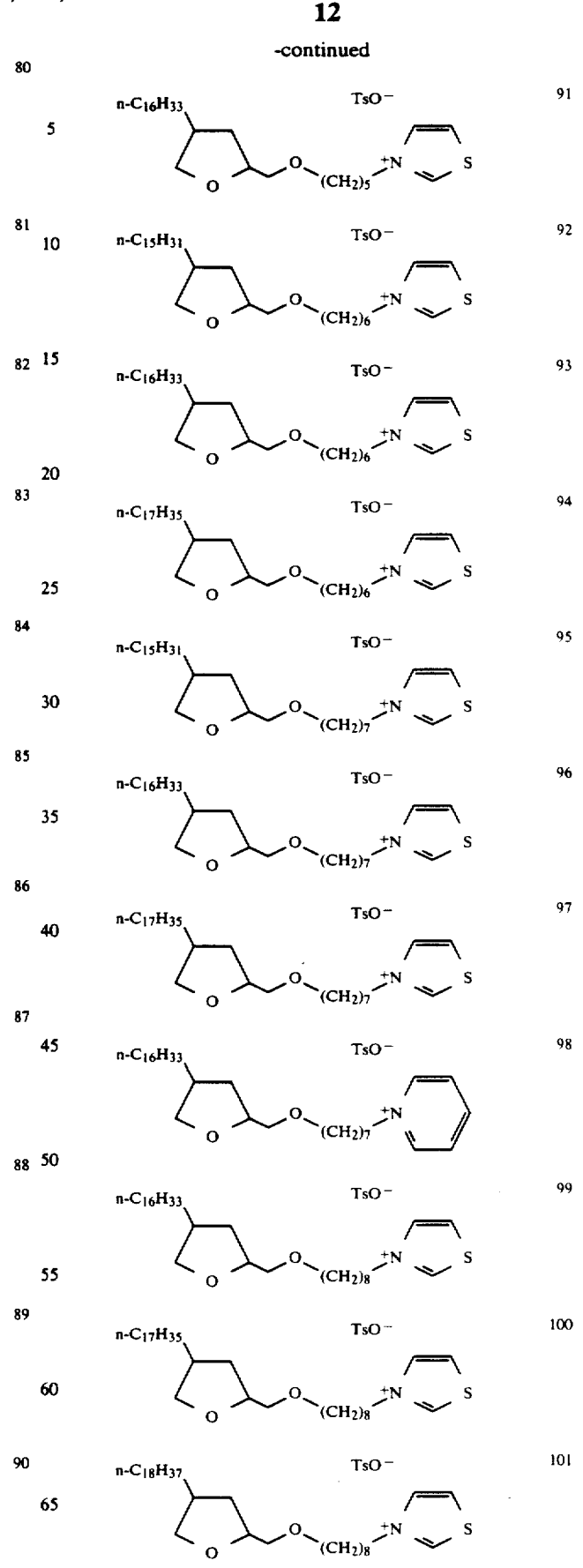

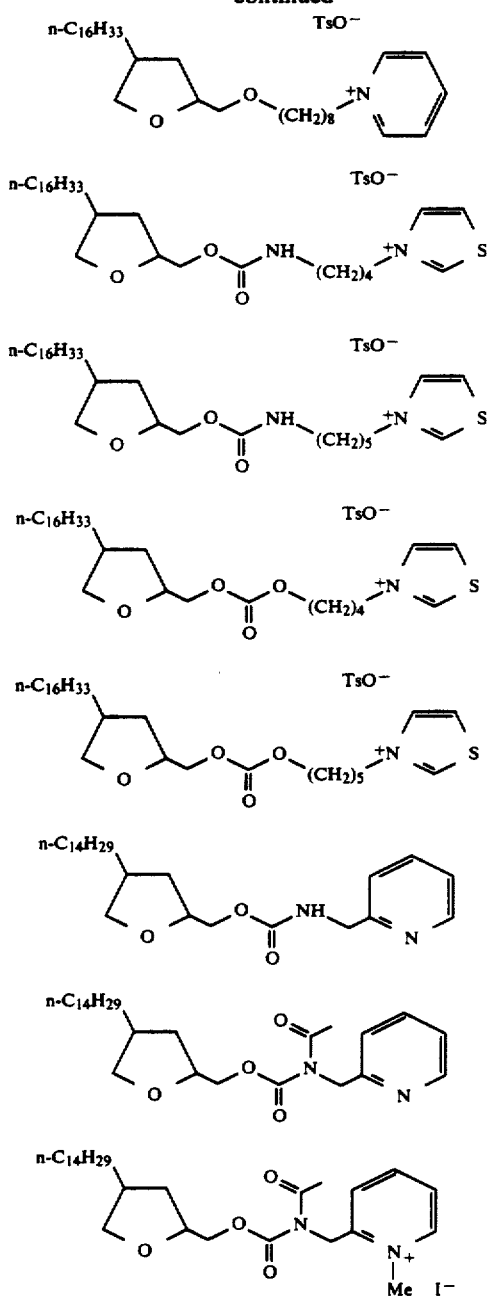

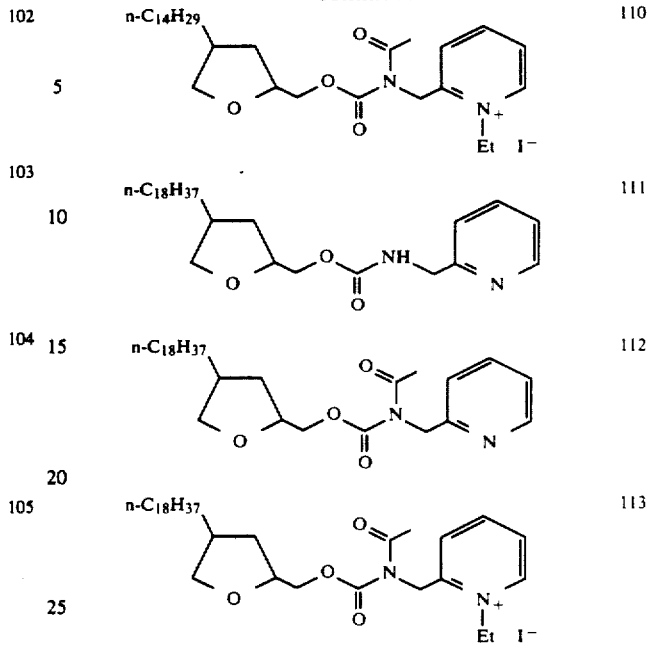

The compounds of the present invention are in vitro inhibitors of the platelet aggregation induced by PAF. On the other hand, these compounds have the capacity to revert the hypotension induced by PAF in anesthetized rats. These facts make them useful as PAF antagonists in the treatment of the diseases in which this substance is involved.

As already stated, the present invention includes not only the tetrahydrofuran derivatives having the general formula I with the —$CH_2XR_1$ group in position 2 and the —$CH_2OR_2$ group in position 4, but also the compounds having —$CH_2OR_2$ in position 2 and —$CH_2XR_1$ in position 4. The pharmacologic tests have demonstrated that, given two —$R_1$ and —$R_2$ groups, the compounds belonging to both families show very similar pharmacologic activities.

It is a further object of the present invention to provide a process for the preparation of the title compounds I. Thus, for the case in which X is an oxygen atom, Scheme I shows the synthetic steps for the preparation of the intermediate alcohols IIa and IIb.

In step A compound V, easily obtained starting with diethyl malonate and allyl bromide as described in the literature (JACS 1933, 55, 4697), is reacted with a reducing agent, such as lithium aluminium hydride, to give the diol III. The reaction is carried out in the presence of a solvent, that could be any solvent as long as does not interact with the reagents; such as for example tetrahydrofuran and diethyl ether. The reaction can be done in a wide range of temperature and time conditions.

Scheme I

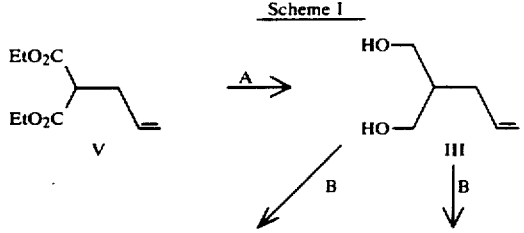

Scheme I

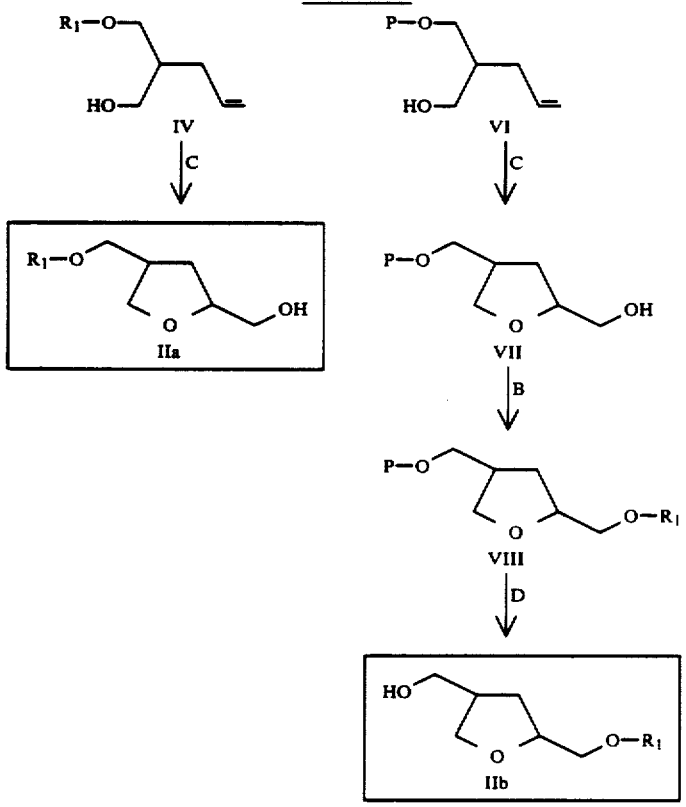

We have found that it is convenient to run the reaction between 0° C. and the boiling temperature of the solvent, for a period of time between 3 and 24 h. Once the reaction is completed, compound III can be separated and purified by conventional techniques, such as flash-chromatograhy or distillation.

In step B one of the two hydroxy groups present in the diol III is functionalized to give compound IV of compound VI. Similarly, the hydroxy group of compound VII is functionalized to give compound VIII.

When compound IV ($R_1$ = alkyl group) is desired, compound III is treated with an amount slightly larger than 1 equivalent of a strong base, such as 1.5 equivalents of sodium hydride, in a solvent compatible with the reagents, such as ether, tetrahydrofuran or dimethylformamide and the intermediate alcoxide is treated in situ with a slight excess of an alkylating reagent, such as an alkyl halide or an alkyl- or arylsulfonate, for example with 1.1 equivalents of n-alkyl bromide. The reaction is done in a wide range of temperatures without being a specific temperature particularly critical. We have found that it is convenient to run the reaction at a temperature ranging from 60° to 100° C. The time needed for the completion of the reaction is in function of the temperature and the nature of the reagents, but a period of time ranging between 3 and 24 h is generally enough. Once the reaction is completed, the desired compound can be isolated by conventional methods. The pure product is obtained by flash-chromatography purification.

If compound IV ($R_1$ = alkylaminocarbonyl) is desired, the diol III is reacted with an equivalent of the corresponding alkyl isocyanate. The reaction is done in the presence of a nitrogen-containing base, which can be used as solvent, if desired. We have found that pyridine is an excellent solvent for this reaction. The reaction can be done in a wide range of temperatures and the temperature of choice is not critical. We have found that the reaction can be conveniently done between 25° C. and the boiling temperature of pyridine, but more preferably between 50° and 70° C. The time required for the reaction depends on the temperature, but a period of time ranging from 30 min. to 6 h is generally preferred. The desired product is isolated following conventional techniques. The pure product can be obtained by flash-chromatography purification of the reaction crude.

Finally, if the compound to be obtained in step B is compound VI, wherein P is a protective group of the hydroxyl function, the reaction to be done is that of diol III with a protective reagent. Although P can be any protective group of the alcohol function, such as benzyl, benzoyl, trialkylsilyl, tetrahydropiranyl, etc., we have found that the trityl (triphenylmethyl) group is very useful for this reaction in terms of reaction conditions and cost of the reagent used (trityl chloride). The reaction is done in a solvent that does not interfere with the reagents, such as for example dichloromethane, chloroform, ether, tetrahydrofuran, etc., and in the presence of a base to neutralize the acid that is formed, such as pyridine and triethylamine. If desired, the reaction can be accelerated by the addition of a catalytic amount of 4-N,N-dimethylaminopyridine. The temperature of the reaction can be adjusted to different values depending on the protective group. When trityl chloride is used, we have found that the temperature of the reaction can range from 0° C. to the boiling temperature of the solvent, preferentially between 20° to 30° C. The reaction time depends on the temperature of choice, nevertheless, a period of time ranging between 2 and 12 h is generally enough. Once the reaction is completed, the desired compound can be isolated and purified by standard techniques, such as for example flash-chromatography.

The tetrahydrofuran ring is formed in step C. This step includes the reaction of a substrate like compound IV or VI with an epoxidating reagent, and the in situ cyclization to give the corresponding compound IIa or VII, respectively. As the epoxidating reagent of choice it is used m-chloroperbenzoic acid. The reaction is done in the presence of a solvent, preferentially a chlorinated hydrocarbon like dichloromethane or chloroform. The reaction can be carried out in a wide range of temperatures and times, although it can be conveniently done at room temperature for 6–48 h, depending on the substrate. We have found that in some occasions a mixture of the desired product and the intermediate epoxide is obtained. The reaction can be completed by treatment with a catalytic amount of an acid, such as perchloric or trifluoroacetic acid. The desired product can be isolated by conventional techniques. If desired, the product can be then purified by chromatography or recrystallization.

The alcohol VII can be converted into product VIII ($R_1$=alkyl or alkylaminocarbonyl), following a similar methodology to that used in step B for the preparation of compounds IV and VI.

Once compound VIII is obtained, step D implies the deprotection of the hydroxyl group to give compound IIb. The reagents needed to do this conversion are determined by the nature of the protecting group P. When P is a trityl group, the transformation to the compound IIb is done using an acid in the presence of an alcohol or water. Although any relatively strong organic or inorganic acid will perform the deprotection, we have found that the use of a sulfonic acid in the presence of methanol, ethanol, tetrahydrofuran, or a mixture of them is satisfactory. The reaction can be done in a wide range of temperatures and the temperature of choice is not particularly critical. In general, it is convenient to do the reaction between 0° C. and the boiling temperature of the solvent, preferentially around 25° C. The reaction time depends on the temperature and the concentration of the acid used. Normally, a period of time ranging between 3 and 24 h is enough. Once the reaction is finished, the isolation of the product is done following standard work-up. If desired, the reaction crude can be purified by flash chromatography or recrystallization.

In order to simplify the exposition, only the synthesis of the derivatives of the alcohol IIa has been presented in schemes II, III and IV. The synthesis of the derivatives of the alcohol IIb proceeds in a similar way and it has not been included in the schemes.

Scheme II shows the synthesis of the compounds of subfamilies Ia and Ib, that is to say, compounds I in which Y is —C(=O)NR$_4$—, R$_4$ being different from H, or equal to H, respectively. As it can be seen in the scheme, in step E the alcohol IIa is reacted with compound X, a phosgene-like compound (that is to say, a doubly activated carbonyl group).

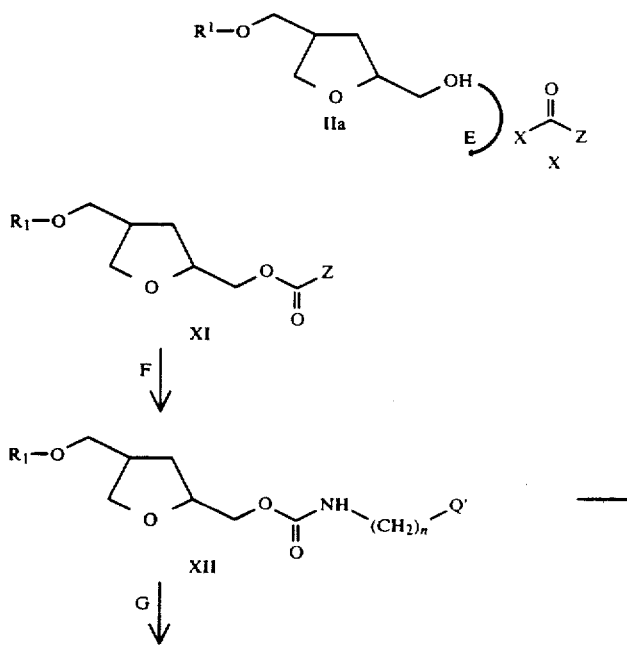

Scheme II

Scheme II

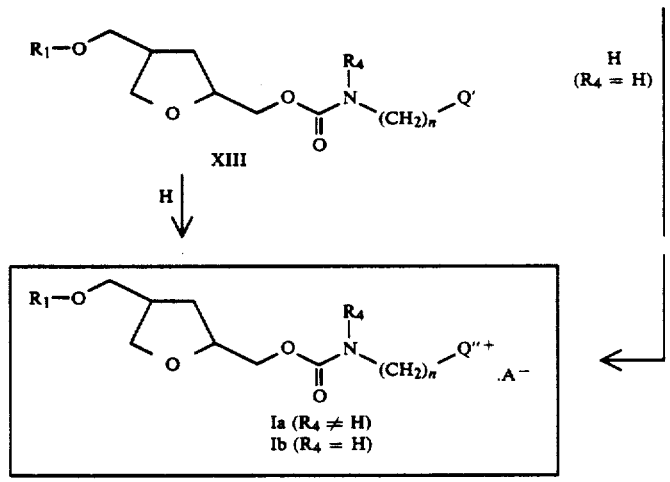

In compound X, the groups X and Z are leaving groups and can be equal (Cl, imidazole, etc.) or different from each other. Although in principle any previously described phosgene equivalent compound can be used, we have found that phenyl chlorocarbonate (X, X=Cl, Z=OPh) is an excellent reagent for this reaction, because of its convenient handling and low market cost. The reaction is done in the presence of a solvent and a base as acid-scavenger. There is not a particular restriction about the solvent utilized, as long as it does not interfere with the reaction and it is capable to dissolve all the reagents. As suitable solvents it can be mentioned the halogenated hydrocarbons, particularly dichloromethane and chloroform, ethers such as diethyl ether, tetrahydrofuran or dioxane, and aromatic hydrocarbons such as benzene or toluene. Furthermore, there is not any particular restriction in relation to the base, as long as it does not affect other parts of the molecule. It is convenient to use an amine, such as triethylamine or pyridine. The reaction can be done in a wide range of temperatures. Conveniently, we carry out the reaction between 0° and 100° C., preferably between 0° and 50° C. The reaction time depends on the nature of the starting materials, the base used, and the temperature of the reaction. A period of time between 30 min. and 24 h is generally satisfactory. The reaction is clean and normally it is not necessary to purify the resulting product. Nevertheless, if desired, product XI can be purified by flash chromatography.

In step F, compound XI (obtained in step E) is transformed to carbamate XII, using a compound of formula $_2$NH—(CH$_2$)$_n$—Q', wherein n is an integer from 0 to 10, and Q' is a heterocyclic group that contains a non-quaternary nitrogen atom and is linked to the alkylene chain by a ring carbon, or Q' is a OP group wherein P is a protective group of the hydroxyl function. The reaction is performed in the presence of a solvent, at a temperature and for a period of time similar to those described for step E. The reaction crude is washed, in that case, with an alkaline aqueous solution to remove the phenol produced during the reaction. The product obtained (XII) can be purified by standard techniques, such as flash chromatography.

When Q'=OP, the conversion of compound XII into compound I, wherein R$_2$ is a group of formula —Y—(CH$_2$)$_n$—Q'''(+) A(−), and Y is —CONR$_4$—, is done in steps L, M and J, which will be described in the discussion of scheme IV.

When Q' is an heterocycle that contains a non-quaternary nitrogen atom and is linked to the alkylene chain by a carbon of the ring, the conversion of compound XII into compound Ia can be done according to steps G and H explained below.

Step G includes the derivatization of the carbamic nitrogen of compound XII to give compound XIII. The reaction involves the use of a reagent of formula R$_4$-X where R$_4$ and X have the previously described meaning. When R$_4$ is an acyl group a compound of formula (R$_4$)$_2$O can also be used. The reaction can be done in two ways: directly using compound XII, or preparing first an alkaline salt of this compound. When R$_4$ is an acyl or alcoxycarbonyl group, of the two methods can be used; while, when R$_4$ is an alkyl group, it is necessary to use the second method. When compound XII is used directly, the reaction is performed in the presence of a solvent, whose nature is not critical as long as it is compatible to the reagents used. We have found that halogenated solvents, such as dichloromethane or chloroform, are efficient in this reaction. On the other hand, the reaction can be done in the presence of an amine as acid-scavenger, such as triethylamine. The use of the amine is optional because the heterocycle Q' already contains a basic nitrogen. The reaction can be done in a wide range of temperatures, between 0° C. and the boiling temperature of the solvent used, but it is preferred a temperature about room temperature. The reaction time depends on the temperature and the nature of the reagents used, nevertheless a period of time ranging between 2 and 72 h is generally enough. Once the reaction is finished, the desired product XIII, can be isolated and purified using conventional methods such as flash chromatography.

When an alkaline salt of compound XII is used, this salt is prepared in situ using a strong base, such as sodium hydride or butyl lithium. Compound R$_4$X is then added. The reaction is performed in a solvent that does not interfere with any of the reagents. As examples of the preferred solvents it can be mentioned ethers such as diethyl ether, tetrahydrofuran or dioxane; and aromatic hydrocarbons such as benzene or toluene. The reaction can be done in a wide range of temperatures, nevertheless we have found that it is preferred to run the reaction at low temperatures for example −78° C. and 0° C., in order to obtain an acceptable yield. The reaction time depends on the temperature and the nature of the reagents. A period of time ranging between 5 min. and 24 h is generally enough. The desired product can be isolated and purified following conventional techniques.

Step H implies the transformation of a compound XIII or XII into a compound Ia or Ib, respectively, where $Q'''(+)$ represents an heterocyclic group that contains a quaternary nitrogen in the ring, and that is linked to an alkylene chain by a carbon, and $A^-$ is a pharmaceutically acceptable anion. The reaction can be done employing the starting material and a reagent of formula $R_5A$ wherein $R_5$ is a lower alkyl group. The reaction can be performed in the absence of solvent in the case that $R_4A$ is a non volatile liquid, or in the presence of a solvent when $R_5A$ is solid or very volatile, but in any case an excess of this reagent is always used. It is preferred to use those solvents having a high polarity. As example of preferred solvents it can be mentioned acetonitrile, tetrahydrofuran, dioxane, dimethylformamide or dimethylsulfoxide. The reaction can be done in a wide range of temperatures and a precise temperature is not particularly critical. We have found that it is convenient to do the reaction at a temperature ranging between room temperature and 120° C. The reaction time depends on the nature of reagent $R_5A$ and the temperature used, but a period of time ranging from 1 to 72 h is generally enough. The desired product is isolated by concentration of the reaction crude or by precipitation with a less polar solvent. The resulting compound is generally pure enough. In the case that it is not pure, it can be purified by conventional techniques such as flash chromatography or recrystallization.

Compounds having formula Ia or Ib are salts wherein the anion $A^-$ comes from the reagent $R_5A$. If desired, this anion can be interchanged using ion exchange resins.

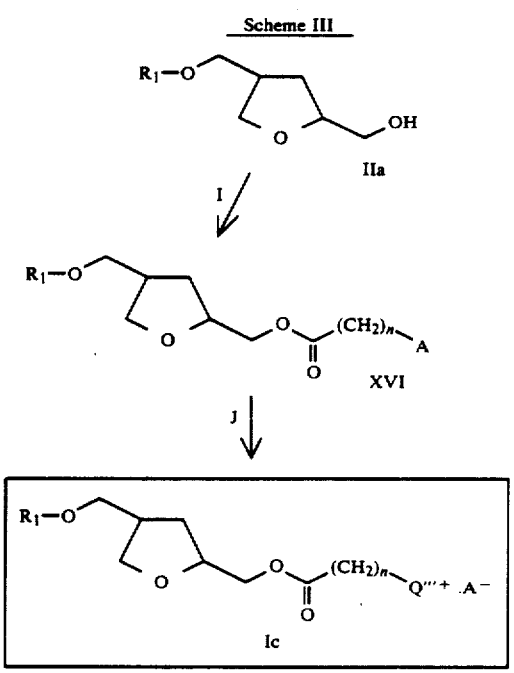

Scheme III shows the synthetic steps that lead to the compounds of the subfamily Ic, that is to say, compounds I in which −Y− is −C(=O)− and Q is an heterocyclic group that is linked to an alkylene chain directly by the quaternary nitrogen of the ring; in this case Q is represented by $Q'''(+)$.

Step I involves the reaction of IIa with a compound of formula Cl−C(=O)−(CH₂)ₙ−A to give compound XVI, wherein A is a leaving group such as an halogen atom or an alkyl or arylsulfonate group. The temperature conditions and the reaction time, as well as the isolation and purification methods, are similar to those described in step B.

In step J compound XVI is reacted with an heterocycle that contains at least a tertiary nitrogen atom in the ring, to give compound Ic wherein $Q'''(+)$ is an heterocyclic group linked to the alkylene chain by the quaternary nitrogen of the ring. The reaction can be done using the heterocycle as solvent or adding a cosolvent, preferably having a polar character such as acetonitrile, tetrahydrofuran, dimethylformamide or dimethylsulfoxide. The reaction is done in a wide range of temperatures. Generally it is convenient to perform the reaction at a temperature ranging between room temperature and 120° C. preferentially between 50 and 90° C. The reaction time depends on the heterocycle used and the temperature of the reaction, nevertheless a period of time ranging between 1 and 48 h is generally enough. The desired compounds can be isolated by evaporation of the volatile components and precipitation with a non polar solvent such as ether. If desired, the product can be purified by one or several recrystallizations.

Scheme IV shows the synthesis of the compounds of subfamily Id, that is to say the compounds of formula I in which Y is a covalent single bond and the heterocyclic group Q is linked to the alkylene chain directly by the quaternary nitrogen of the ring, in which case Q is represented by $Q'''(+)$. In the first step (step K) the alcohol IIa is transformed to the corresponding alcoxide and is reacted with a compound of formula A−(CH₂)ₙ−OP, wherein A is a leaving group, such as halogen, or an alkyl or arylsulfonate group, and P is a protecting group of the hydroxyl function. The reaction includes two steps, the formation of the alcoxide and the in situ reaction with an alkylating agent. For the formation of the alcoxide a strong base like sodium hydride or butyl lithium can be used. In the second step an alkylating agent, generally dissolved in the same solvent used in the previously step, is added. This solvent can be in principle any polar solvent that does not interfere with the reaction. We have found that dimethylformamide is particularly useful. The reaction can be performed in a wide range of temperatures. We have found that is convenient to do it at a temperature ranging between 50° and 120° C. The time needed for the reaction can vary widely, nevertheless a period of time ranging between 4 and 30 h is generally enough. Once the reaction is finished, the desired product can be purified by flash chromatography.

Step L includes the deprotection of the hydroxyl group of compound XVIII. The reagents and the reaction conditions utilized depend on the nature of the group P used. P can be any of the protective groups commonly used for the protection of the hydroxyl function, such as benzyl, trityl, trialkylsilyl or tetrahydropiranyl. In the present invention we have used the tetrahydropiranyl group.

Scheme IV

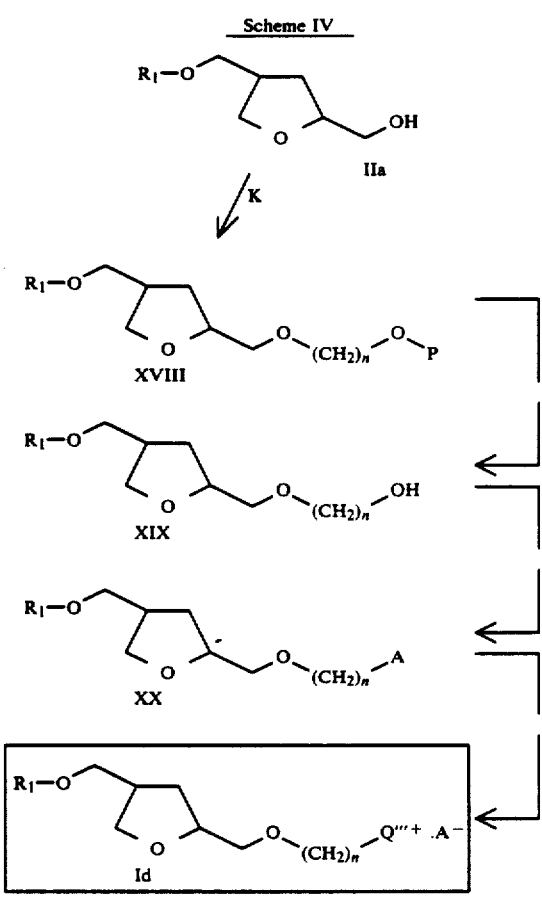

Step L involves, thus, an acid hydrolysis or alcoholysis. The reaction is carried out in a polar solvent, such as methanol for the alcoholysis, or a mixture of water and a cosolvent, such as tetrahydrofuran, for the hydrolysis. In both cases an acid is needed to catalyze the reaction. Such acid can be, in principle, any relatively strong acid, such as hydrochloric, sulfuric, camphorsulfonic or toluenesulfonic acid. The reaction can be done in a wide range of temperatures. Although the temperature of choice is not particularly critical, we have found that a temperature between 0° and 50° C. is convenient. The reaction time depends on the nature of the reagents, the temperature and the acid concentration, nevertheless a period of time ranging between 1 and 12 h is generally enough. Once the reaction is finished, the reaction mixture is neutralized and the desired product is isolated and purified using conventional techniques.

Step M involves the conversion of the hydroxyl group of compound XIX in a leaving group A. When A is an alkyl- or arylsulfonate group, compound XX is obtained by reacting compound XIX with the corresponding alkyl- or arylsulfonyl chloride in the presence of a base. The nature of the solvent and the base used, as well as the conditions of temperature and time used are similar to those described in step E.

Finally, compound XX can be transformed into the final product Id by the process described in step J.

For the case in which the group —X— of general formula I is covalent single bond, analogous syntheses to those described above can be carried out, but using compounds XXIa or XXIb as starting materials, instead of compounds IIa or IIb. The cyclic ethers XXIa can be prepared as a (1:1) mixture of cis and trans following Scheme V (in which XXIa and XXIb are shown).

In the formulas of Scheme V, $R_1$ is as previously defined, and $R_b$ is a lower alkyl group. In step N, an ester having the formula XXIV is treated with a strong base, like lithium diisopropylamidure, and the produced enolate is alkylated with a suitable haloalkene, like for example 3-bromo-1-propene, in the presence of an aliphatic ether or a cyclic ether, like tetrahydrofuran, at a temperature ranging from −40° C. to 0° C. for 3–12 h, to afford compound XXIII. The compound obtained in that way is reduced in step O by treatment with an excess of a metal hydride, such as lithium aluminium hydride, in an aliphatic ether or a cyclic ether, like tetrahydrofuran, at −40° C.-0° C., for 3–12 h to afford compound XXII. In step P, compound XXII is treated with an organic peracid, like m-chloroperbenzoic acid, in an inert organic solvent, such as for example a chlorinated solvent (like methylene chloride), at 0°-30° C., for a period of time long enough to consume the totality of the alkene, to afford compound XXIa as a (1:1) mixture of the cis and trans isomers.

The pure cis and trans isomers of the cyclic ether XXIa can be prepared diastereoselectively following the reaction sequence described in Scheme VI in which $R_c$ and $R_{c'}$ are lower alkyl groups, equal or different to each other, $R_d$ is a lower alkyl or aryl group, and Hal is an halogen atom.

Scheme V

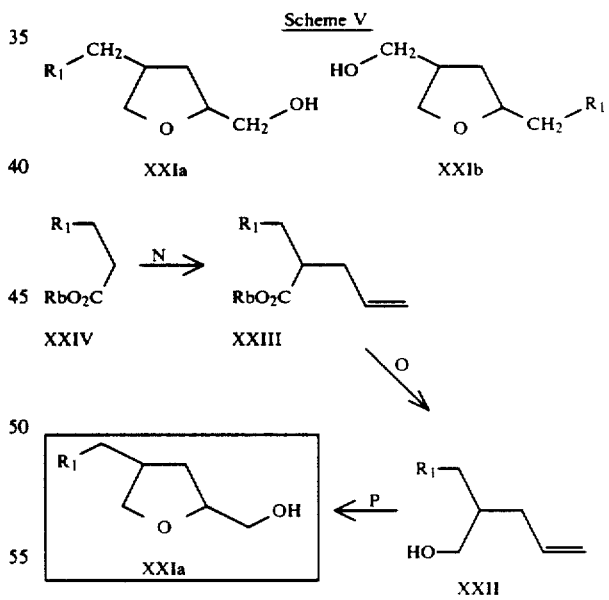

Scheme VI

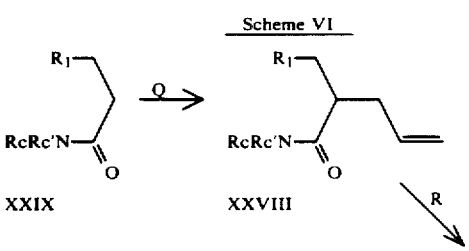

-continued
Scheme VI

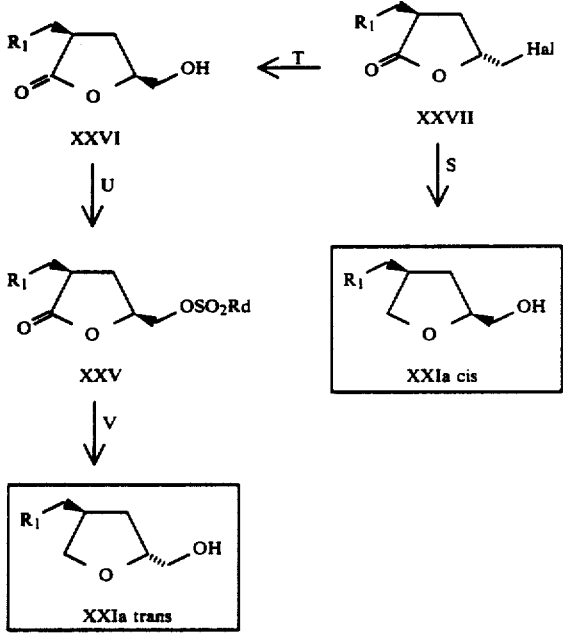

The amides having formula XXIX, which are the starting materials for the previous synthetic sequence, can be obtained by a conventional method starting from the corresponding acid chloride (*J. Am. Chem. Soc.*, 76, 1372, 1954). In the first step of the sequence, step Q, amide XXIX is alkylated with a suitable haloalkene to give compound XXVIII. In this reaction it is possible to follow the same methodology used in step N (scheme V). In step R, compound XXVIII is subject to a halolactonization process. The mentioned compound is treated with a source of positive halogen, such as for example iodine or N-bromosuccinimide, in an inert organic solvent, like methylene chloride, at 0°-30° C., for 10 h-5 days, to afford a mixture of cis and trans isomers in a very favorable proportion for the trans isomer XXVII. The pure trans isomer can be separated by silica gel chromatography. In step S, compound XXVII is treated with a metal hydride, such as borane-dimethylsulfide, in a solvent like tetrahydrofuran, at 0°-30° C., for 3-72 h, to give the corresponding diol. This compound is treated next with a base, for example, potassium carbonate, in a lower alcohol such as methanol, at 0°-60° C., for 30 min.–4 h, to afford compound XXIa cis. The pure XXIa trans can be prepared following a three-step sequence (steps T, U and V) that is initiated with the treatment of compound XXVII with a metal hydroxide, such as lithium hydroxide, in the presence of water and a cyclic ether, such as for example tetrahydrofuran, at a temperature ranging from −10° to 30° C. for 1-6 h, to give compound XXVI. Then, the mentioned compound is treated (step U) with an alkyl- or arylsulfonyl chloride, like 4-methylbenzenesulfonyl chloride, in the presence of an amine such as pyridine, in an organic solvent, such as for example methylene chloride, at 0°-30° C. for 1-36 h, to give compound XXV. In the last step (step V) compound XXV is reduced and treated with a base following the same procedure described for the step S, to give compound XXIa trans.

Finally, the cyclic ethers XXIb can be prepared as a (1:1) mixture of cis and trans isomers according to Scheme VII. In step X of this scheme, alcohol VII is transformed in the corresponding alkyl or arylsulphonate derivative, following the methodology described in step U of scheme VI, and then it is treated with $(R_1)_2CuLi$ to give compound XXX (cfr. *Tetrahedron* 1978, 34, 1449-1452). Compound XXIb is obtained by deprotection of the hydroxyl group present in compound XXX, as it is described in step D of scheme I.

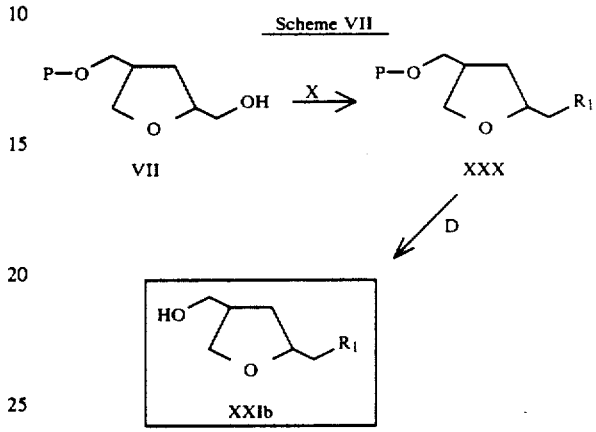

The title compounds I are useful as PAF inhibitors, as demonstrated by their ability to inhibit the in vitro platelet aggregation induced by PAF in rabbits according to test 1:

TEST 1: INHIBITION OF PLATELET AGGREGATION INDUCED BY PAF

The blood is obtained by cardiac puncture of male New Zealand albino rabbits (between 2 and 2.5 Kg of weight) and coagulation is prevented by adding 1 part of 3.16% sodium citrate dihydrate in 9 parts of blood. The platelet rich plasma (PRP) is prepared by blood centrifugation at 250 xg for 10 min. at 4° C. and it is diluted with platelet poor plasma (PPP) obtained by additional centrifugation at 300 xg for 10 min. The amount of platelets is adjusted to $3 \times 10^{-5}/mm^3$. The platelet aggregation induced by PAF ($C_{18}$, prepared in our laboratory) (16 nM, final) is determined by the Born nephelometric technique (*J. Physiol.*, 1962, 162, 67) using a aggregometer Chrono-log 500. The activities of the inhibitors are expressed as $IC_{50}$, that is to say the concentration of the drug needed to inhibit the platelet aggregation in a 50%. The results are shown in table 1:

TABLE 1

| Compound number | $IC_{50}$ (M) |
|---|---|
| 1 | 2.5 |
| 2 | 0.9 |
| 3 | 0.7 |
| 4 | 1.4 |
| 5 | 4.8 |
| 6 | 8.6 |
| 7 | 5.9 |
| 10 | 3.8 |
| 12 | 0.1 |
| 13 | 0.022 |
| 15 | 0.048 |
| 19 | 0.09 |
| 20 | 0.034 |
| 25 | 0.095 |
| 49 | 0.0045 |
| 53 | 0.027 |

TABLE 1-continued

| Compound number | IC$_{50}$ (M) |
| --- | --- |
| 58 | 0.009 |
| 61 | 2 |
| 62 | 2.1 |
| 63 | 1.4 |
| 64 | 1.5 |
| 66 | 1.6 |
| 68 | 0.14 |
| 70 | 2.2 |
| 71 | 8.2 |
| 72 | 3.4 |
| 73 | 15 |
| 74 | 6.3 |
| 75 | 50 |
| 76 | 180 |
| 77 | 120 |
| 78 | 210 |
| 79 | 39 |
| 80 | 75 |
| 81 | 51 |
| 82 | 1.8 |
| 83 | 2.6 |
| 84 | 2.6 |
| 109 | 0.24 |
| 113 | 0.20 |

Furthermore, it has been found that the title compounds I are inhibitors of the hypotension induced by PAF according to test 2.

TEST 2—INHIBITION OF THE HYPOTENSIVE EFFECT INDUCED BY PAF IN NORMOTENSE RATS

Male Sprague Dawley rats, of 180-220 g of weight, anesthetized with sodium pentobarbital (50 mg/Kg, i.p. 1 mL/100 g) have been used. In order to measure the average arterial pressure a polyethylene catheter was introduced into the carotid artery. The arterial pressure was recorded with the help of a transducer connected with a R611 Beckman polygraph. The tested compounds were administrated through the femoral vein 3 min. before the injection of PAF (0.5 mg/Kg, i.v.). The inhibition of the hypotension induced by PAF of the different compounds, expressed as IC$_{50}$, is shown in table 2.

TABLE 2

| Compound number | IC$_{50}$ (mg/Kg, i.v.) |
| --- | --- |
| 1 | 3.7 |
| 2 | 1.4 |
| 3 | 3 |
| 4 | 1.2 |
| 5 | 1.6 |
| 6 | 1.9 |
| 7 | 3.6 |
| 10 | 6.6 |
| 12 | 0.23 |
| 13 | 0.035 |
| 15 | 0.035 |
| 19 | 0.14 |
| 20 | 0.035 |
| 25 | 0.081 |
| 49 | 0.033 |
| 53 | 0.042 |
| 58 | 0.044 |
| 61 | 2.1 |
| 63 | 2.5 |
| 64 | 1.1 |
| 66 | 5 |
| 68 | 0.11 |
| 70 | 2.2 |
| 72 | 3.2 |
| 82 | 1.5 |
| 109 | 0.39 |
| 113 | 0.20 |

Solid compositions according to the present invention for oral administration include compressed tablets, dispersible powders, granules and capsules. In tablets, one or more of the active component (s) is admixed with at least one inert diluent such as lactose, starch, mannitol, microcrystalline cellulose or calcium phosphate; granulating and disintegrating agents for example corn starch, alginic acid; binding agents for example, starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrilic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as etoxylated saturated glycerides, and they may also present controlled release. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixtured with a dispersing or wetting agent; suspending agent, such as sodium carboxymethylcellulose, methylcellulose, hydroxypropylmethylcellulose, sodium alginate, polyvinylpirrolidone, gum tragacanth, xantham gum, gum acacia; and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing inert diluents commomly used, such as distilled water, ethanol, sorbitol, glycerol, propylene glycol. Such compositions may also comprise adjuvants such as wetting agents, suspending agents, sweetening, flavouring, perfuming, preserving agents and buffers.

Other compositions for oral administration include spray compositions which may be prepared by known methods and which comprise one or more active compound (s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may be also administered in the form of suppositories for rectal administration of the drug; creams, ointments, jellies, solutions or suspensions for topical use and pessaries for vaginal administration.

The following are representative pharmaceutical compositions for tablets, capsules, syrups, aerosols and injectable preparations. They can be prepared following standard procedures and they are useful as inhibitors of platelet activating factor.

| Tablets | | |
| --- | --- | --- |
| Title compound I | | 100 mg |
| Dibasic calcium phosphate | | 125 mg |
| Sodium starch glycolate | | 10 mg |
| Talc | | 12.5 mg |
| Magnesium stearate | | 2.5 mg |
| | | 250.0 mg |
| Hard gelatin capsules | | |
| Title compound I | | 100 mg |
| Lactose | | 197 mg |
| Magnesium stearate | | 3 mg |
| | | 300 mg |
| Syrup | | |
| Title compound I | | 0.4 g |
| Sucrose | | 45 g |
| Flavouring agent | | 0.2 g |
| Sweetening agent | | 0.1 g |
| Water | to | 100 mL |
| Aerosol | | |
| Title compound I | | 4 g |
| Flavouring agent | | 0.2 g |
| Propylene glycol | to | 100 mL |
| Suitable propellent | to | 1 unit |
| Injectable preparation | | |
| Title compound I | | 100 mg |
| Benzylic alcohol | | 0.05 mL |
| Propylene glycol | | 1 mL |
| Water | to | 5 mL |

The following examples illustrate, but do not limit, the preparation of the compounds of the present invention.

EXAMPLE 1

(±)-cis,
trans-3-[7-[(4-dodecyloxymethyltetrahydrofuran-2-yl)methoxy]heptyl]thiazolium 4-methylbenzenesulphonate (a) 2-dodecyloxymethyl-4-penten-1-ol To a suspension of sodium hydride (2.46 g, 56 mmol) in anhydrous dimethylformamide (30 mL) under argon atmosphere, it was added dropwise a mixture of 2-allyl-1,3-propanediol (5 g, 43 mmol) and bromododecane (12 g, 48 mmol) dissolved in anhydrous dimethylformamide (50 mL) and the resulting mixture is heated at 60° C. for 6 h. The mixture is cooled to room-temperature, poured into a 1M pH7 phosphate buffer and extracted with hexane. The organic phase was dried over anhydrous sodium sulfate and after removing the solvent, 13.4 g of an oil was obtained. The crude was purified by column chromatography (silica gel, hexane:ethyl acetate 15%) to afford 6.8 g of the desired product as a colorless oil (56% yield).

IR (film) v: 3425, 3072, 2919, 2850, 1637, 1463, 1440, 1373, 1112, 1042, 911 cm$^{-1}$.

(b) (±)-cis,
trans-(4-dodecyloxymethyltetrahydrofuran-2-yl)methanol

The compound prepared in example 1a (6.8 g, 24 mmol) was dissolved in methylene chloride (50 mL) and 55% m-chloroperbenzoic acid (9.8 g, 31 mmol) was added and the mixture was stirred for 24 h. Afterwards, it was diluted with methylene chloride and washed with 1N sodium thiosulfate. The organic phase was dried over anhydrous sodium sulfate, and the solvent was evaporated. To the resulting oil (7.1 g) dissolved in chloroform (100 mL) and cooled in a ice-bath was added 0.2 mL of trifluoroacetic acid and the mixture was stirred for 2 h. Afterwards, it was diluted with methylene chloride and washed with 5% sodium bicarbonate. The organic phase was dried over anhydrous sodium sulfate, the solvent was evaporated and the resulting oil purified by chromatography (silica gel, hexane: ethyl acetate 35%), to afford 4.1 g of a (1:1) mixture of the cis and trans isomers as a colorless oil (58% yield).

IR (film) v: 3429, 2919, 2850, 1463, 1375, 1113, 1046 cm$^{-1}$; $^1$H-NMR (90 MHz, CDCl$_3$) δ: 0.87 (m, 3H), 1.1-2.4 (complex signal, approx. 25H), 2.54 (q, J=0.6Hz, 1H), 3.25-4.00 (complex signal, 9H).

(c) (±)-cis,
trans-7-[(4-dodecyloxymethyltetrahydrofuran-2-yl)methoxy]heptyl, tetrahydropiranyl ether To a suspension of sodium hydride (0.4 g, 10 mmol) in anhydrous dimethylformamide (7 mL) under argon atmosphere was added a mixture of the compound prepared in example 1b (1.7 g, 5.6 mmol) and 7-(tetrahydropiranyl-2-oxy)heptyl 4-methylbenzenesulfonate (3.7 g, 10 mmol) and the resulting mixture was heated at 60° C. for 6 h. After cooling at room temperature, the mixture was poured into 1M pH 7 phosphate buffer and was extracted with hexane. The organic phase was dried over anhydrous sodium sulfate and after evaporation of the solvent 4.3 g of an oil was obtained. That solid was purified by column chromatography (silica gel, hexane: ethyl acetate 15%) to afford 1.04 g of the desired product as a colorless oil (66% yield).

IR (film) v: 2925, 2851, 1462, 1362, 1350, 1119, 1078, 1033 cm$^{-1}$; $^1$H-NMR (60 MHz, CDCl$_3$) δ: 0.7-1.9 (complex signal, 42H), 3.6 (m, 15H), 4.6 (m, 1H).

(d) (±)-cis,
trans-7-[(4-dodecyloxymethyltetrahydrofuran-2-yl)methoxy]heptanol

A mixture of the compound prepared in example 1c (1.84 g, 3.7 mmol), camphorsulfonic acid (0.36 g) and 54 mL of methanol was stirred at room temperature for 16 h. Afterwards, the mixture was concentrated to dryness and the group was treated with 1M pH7 phosphate buffer and extracted with ethyl acetate. The organic phase was dried over anhydrous sodium sulfate and after evaporating the solvent 1.32 g of a colorless oil were obtained (86% yield).

IR (film) v: 3437, 2923, 2851, 1462, 1366, 1115 cm$^{-1}$.

(e) (±)-cis, trans-7-[(4-dodecyloxymethyltetrahydrofuran-2-yl)methoxy]heptyl] 4-methylbenzenesulfonate The compound obtained in example 1d (1.3 g, 3.2 mmol) was dissolved in dry pyridine (5 mL), over this solution cooled at 0° C. it was added p-toluenesulfonyl chloride (0.69 g, 3.6 mmol) and it was stirred at 4° C. for 12 h. Afterwards, the reaction mixture was poured into water (50 mL), extracted twice with diethyl ether and the organic phase was washed with 0.1M HCl solution. The organic phase was dried over anhydrous sodium sulfate and after removal of the solvent, 1.32 g of a solid was obtained. That solid was purified by column chromatography (silica gel, hexane: ethyl acetate 10%) to afford 0.73 g of a white solid (40% yield).

IR (KBr) ν: 2924, 2852, 1595, 1462, 1361, 1187, 1176, 1112, 939 cm$^{-1}$; $^1$H-NMR (60 MHz, CDCl$_3$) δ: 0.8–1.8 (complex signal, 36H), 2.45 (s, 3H), 3.1–4 (m, 11H), 4.05 (t, 2H), 7.4 (d, J=8 Hz, 2H), 7.8 (d, J=8 Hz, 2H).

(f) Preparation of the Title Compound of this Example

A mixture of 0.73 g of the compound obtained in example 1e and 1 mL of thiazole was heated at 100° C. for 6 h. After cooling to room temperature, the mixture was diluted with diethyl ether and 0.27 g of the title compound of this example as a hemihydrate were separated (32% yield).

mp: 53.8°–61.0° C.; IR (KBr) ν: 3447, 2923, 1463, 1192, 1121, 1033, 1011 cm$^{-1}$; Analysis calculated for C$_{35}$H$_{59}$NO$_6$S$_2$·½H$_2$O: C 63.4%; H 9.1%; N 2.1%. Found: C 63.47%; H 9.46%; N 2.25%.

EXAMPLE 2

(±)-cis, trans-3-[7-(4-tetradecyloxymethyltetrahydrofuran-2-yl)methoxy]heptyl]thiazolium 4-methylbenzenesulfonate (a) 2-tetradecyloxymethyl-4-penten-1-ol Following the same procedure described in example 1a, and using instead of bromododecane an equivalent amount of tetradecyl 4-methylbenzenesulfonate, a colorless oil was obtained (37% yield). IR (film) ν: 3405, 3072, 2919, 2851, 1637, 1463, 1375, 1112, 1040 cm$^{-1}$; $^1$H-NMR (60 MHz, CDCl$_3$) δ: 0.6–2.1 (complex signal, 30H), 2.8 (t, J=6Hz, 1H), 3.4 (m, 6H), 5.0 (m, 2H), 5.7 (m, 1H).

(b) (±)-cis, trans-(4-tetradecyloxymethyltetrahydrofuran-2-yl)methanol

Following the same procedure described in example 1b, and using instead of the compound prepared in example 1a, an equivalent amount of the compound prepared in example 2a, a colorless oil was obtained (78% yield).

IR (film) ν: 3427, 2920, 2850, 1463, 1375, 1113, 1045 cm$^{-1}$; $^1$H-NMR (60 MHz, CDCl$_3$) δ: 0.6–1.8 (complex signal, 30H), 2.65 (m, 1H), 3–4.1 (m, 9H). (c) (±)-cis, trans-7-[(4-tetradecyloxymethyltetrahydrofuran-2-yl)methoxy]heptyl, tetrahydropiranyl ether Following the same procedure described in example 1c, and using instead of the compound prepared in example 1b, the compound prepared in example 2b, a colorless oil was obtained (42% yield).

IR (film) ν: 2923, 2850, 1462, 1363, 1350, 1119, 1078 cm$^{-1}$; $^1$H-NMR (60 MHz, CDCl$_3$) δ: 0.7–2.6 (complex signal, 46H), 3.1–4.3 (m, 15H), 4.6 (m, 1H).

(d) (±)-cis, trans-7-[(4-tetradecloxymethyltetrahydrofuran-2-yl)methoxy]heptanol Following the same procedure described in example 1d, and using instead of the compound prepared in example 1c, the compound prepared in example 2c, a colorless oil was obtained (quantitative yield).

IR (film) ν: 3443, 2922, 2850, 1462, 1373, 1114 cm$^{-1}$; $^1$H-NMR (60 MHz, CDCl$_3$) δ: 0.7–1.8 (complex signal, 40H), 3–4.3 (complex signal, 14H).

(e) (±)-cis, trans-7-[(4-tetradecyloxymethyltetrahydrofuran-2-yl)methoxy]heptyl 4-methylbenzenesulfonate Following the same procedure described in example 1e, and using instead of the compound prepared in example 1d, the compound prepared in example 2d, a white solid was obtained (50% yield).

IR (KBr) ν: 2922, 2851, 1595, 1463, 1361, 1187, 1176, 1113 cm$^{-1}$.

(f) Preparation of the title compound of this example

Following the same procedure described in example 1f, and using instead of the compound prepared in example 1e, the compound prepared in example 2e, the title compound of this example was obtained as a hemihydrate (81% yield).

mp: 60.8°–66.0° C.; IR (KBr) ν: 3440, 3141, 2917, 1846, 1464, 1213, 1193, 1120, 1034, 1010 cm$^{-1}$.

Analysis calculated for C$_{37}$H$_{63}$NO$_6$S$_2$·½H$_2$O: C 64.3%; H 9.3%; N 2.0%. Found: C 64.43%; H 9.55%; N 2.20%.

EXAMPLE 3

(±)-cis, trans-3-[6-[(4-tetradecyloxymethyltetrahydrofuran-2-yl)methoxy]hexyl]thiazolium 4-methylbenzenesulfonate (a) (±)-cis, trans-6-[(4-tetradecyloxymethyltetrahydrofuran-2-yl)methoxy]hexyl, tetrahydropiranyl ether Following the procedure described in example 2c, and using instead of 7-tetrahydropiranyl-2-oxy)heptyl 4-methylbenzenesulfonate, 6-(tetrahydropiranyl-2-oxy)-hexyl 4-methylbenzenesulfonate, the desired product was obtained as an oil (60% yield).

Rf=0.64 (silica gel, hexane: ethyl acetate 1:1); IR (film) ν: 2921, 2850, 1449, 1365, 1199, 1187, 1177, 1077 cm$^{-1}$; $^1$H-NMR (60 MHz, CDCl$_3$) δ: 1.7–2.1 (complex signal, 44H), 3.2–4.2 (complex signal, 15H), 4.6 (m, 1H).

(b) (±)-cis, trans-6-[(4-tetradecyloxymethyltetrahydrofuran-2-yl)methoxy]hexanol Following the procedure described in example 1d, and using instead of the compound prepared in example 1c, the compound prepared in example 3a, the desired compound was obtained as a colorless oil (88% yield).

Rf: 0.3 (silica gel, hexane:ethyl acetate 1:1); $^1$H-NMR (60MHz, CDCl$_3$) δ : 0.3–2 (complex signal, 48H), 3.1–4.2 (complex signal, 14H).

(c) (±)-cis, trans-6-[(4-tetradecyloxymethyltetrahydrofuran-2-yl)methoxy]hexyl 4-methylbenzenesulfonate Following the procedure described in example 1e, and using instead of the compound prepared in example 1d, the compound prepared in example 3b, the desired compound was obtained as a white solid (30% yield).

Rf=0.11 and 0.15 for the cis and trans isomers (silica gel, hexane:ethyl acetate 20%); IR (KBr) v: 2923, 2851, 1595, 1463, 1359, 1187, 1176, 1097, 960 cm$^{-1}$.

(d) Preparation of the Title Compound of this Example

Following the procedure described in example 1f, and using instead of the compound prepared in example 1e, the compound prepared in example 3c, the desired product was obtained in a dihydrated form (64% yield).

mp: 88.7°-123.2° C.; IR (KBr) v: 3441, 3065, 2921, 2851, 1547, 1462, 1188, 1122, 1034, 1010 cm$^{-1}$.

Analysis calculated for $C_{36}H_{61}NO_6S_2 \cdot 2H_2O$: C 61.4%; H 9.2%; N 2.0%. Found: C 61.48%; H 9.04%; N 2.38%.

EXAMPLE 4

(±)-cis, trans-3-[6-[(4-hexadecyloxymethyltetrahydrofuran-2-yl)methoxy]hexyl]thiazolium 4-methylbenzenesulfonate

(a) 2-hexadecyloxymethyl-4-penten-1-ol

Following the procedure described in example 1a, and using instead of bromododecane, bromohexadecane, the desired compound was obtained as a colorless oil (71% yield).

Rf: 0.31 (silica gel, hexane:ethyl acetate 20%); IR (film) v: 3425, 3072, 2921, 2850, 1637, 1463, 1373, 1236, 1114, 1043 cm$^{-1}$; $^1$H-NMR (60 MHz, CDCl$_3$) δ: 0.7–2.2 (complex signal, 35H), 3.5 (m, 6H), 5.05 (m, 2H), 5.6 (m, 1H).

(b) (±)-cis, trans-[(4-hexadecyloxymethyltetrahydrofuran-2-yl)methanol

Following the procedure described in example 1b, and using instead of the compound prepared in example 1a, the compound prepared in example 4a, the desired compound was obtained as a waxy white solid (65% yield).

Rf=0.3 (silica gel, hexane:ethyl acetate 1:1); mp: 36.7°-38.1° C.; IR (film) v: 3403, 2913, 1463, 1376, 1113, 1050, 721 cm$^{-1}$; $^1$H-NMR (60MHz, CDCl$_3$) δ: 0.7–1.8 (complex signal, 34H), 2.5 (m, 1H), 3.2–4.3 (complex signal, 9H); $^{13}$C-NMR (50.3 MHz, CDCl$_3$) δ: 14.13 (CH$_3$), 22.71 (CH$_2$), 26.17 (CH$_2$), 29.39 (CH$_2$), 29.51 (CH$_2$), 29.65 (CH$_2$), 29.72 (CH$_2$), 30.42 (CH$_2$), 30.55 (CH$_2$), 31.96 (CH$_2$), 39.59 (CH), 39.78 (CH), 64.65 (CH$_2$), 64.86 (CH$_2$), 71.13 (CH$_2$), 71.40 (CH$_2$), 72.52 (CH$_2$), 73.00 (CH$_2$), 79.04 (CH), 79.97 (CH).

(c) (±)-cis, trans-6-[(4-hexadecyloximethyltetrahydrofuran-2-yl)methoxy]hexyl tetrahydropiranyl ether Following the procedure described in example 3a, and using instead of the compound prepared in example 2b, the compound prepared in example 4b, the desired product was obtained as a colorless oil (33% yield).

IR (film) v: 2923, 2851, 1462, 1362, 1119, 1078, 1034 cm$^{-1}$; $^1$H-NMR (60 MHz, CDCl$_3$) δ: 0.7–2.2 (complex signal, 48H), 3.2–4.3 (complex signal, 15H), 4.6 (m, 1H).

(d) (±)-cis, trans-6-[(4-hexadecyloxymethyltetrahydrofuran-2-yl)methoxy]hexanol Following the procedure described in example 1d, and using instead of the compound prepared in example 1c, the compound prepared in example 4c, the desired compound was obtained as a colorless oil (94% yield).

Rf=0.33 (silica gel, hexane: ethyl acetate 1:1); IR (film) v: 3423, 2921, 2851, 1462, 1373, 1115 cm$^{-1}$; $^1$H-NMR (60 MHz, CDCl$_3$) δ: 0.6–2.1 (complex signal, 43H), 2.7 (m, 1H), 3.1–4.3 (complex signal, 13H).

(e) (±)-cis, trans-6-[(4-hexadecyloxymethyltetrahydrofuran-2-yl)methoxy]hexyl 4-methylbenzenesulfonate Following the procedure described in example 1e, and using instead of the compound prepared in example 1d, the compound prepared in example 4d, the desired compound was obtained as a white solid (27% yield).

Higher Rf isomer: IR (KBr) v: 2921, 2851, 1595, 1462, 1361, 1187, 1176, 1114 cm$^{-1}$; $^1$H-NMR (60 MHz, CDCl$_3$) δ: 0.7–2.0 (complex signal, 42H), 2.55 (s, 3H), 3.5 (m, 9H), 4.1 (m, 4H), 7.45 (d, J=8Hz, 2H), 7.9 (d, J=8Hz, 2H).

Lower Rf isomer: IR (KBr) v: 2921, 2850, 1595, 1462, 1361, 1187, 1176, 1114 cm$^{-1}$; $^1$H-NMR (60 MHz, CDCl$_3$) δ: 0.7–2.0 (complex signal, 42H), 2.55 (s, 3H), 3.5 (m, 8H), 4.0 (m, 5H), 7.45 (d, J=8Hz, 2H), 7.95 (d, J=8Hz, 2H).

(f) Preparation of the Title Compound of this Example

Following the procedure described in example 1f, and using instead of the compound prepared in example 1e, the compound prepared in example 4e, the desired compound was obtained as a white solid (72% yield).

mp: 68.7°-80.7° C.; IR (KBr) v: 3129, 2914, 2847, 1551, 1464, 1376, 1211, 1192, 1120, 1034, 1010, 817 cm$^{-1}$.

Analysis calculated for $C_{38}H_{65}NO_6S_2$: C 65.7%; H 10.3%; N 2.0%. Found: C 65.38%; H 9.90%; N 2.05%.

EXAMPLE 5

(±)-cis, trans-3-[6-[(4-hexadecyloxymethyltetrahydrofuran-2-yl)methoxy]-6-oxohexyl]thiazolium 4-methylbenzenesulfonate

(a) (±)-cis, trans-6-[(4-hexadecyloxymethyltetrahydrofuran-2-yl)methoxy]-6-oxohexyl 4-methylbenzenesulfonate To a solution of the compound prepared in example 4b (0.5 g, 1.4 mmol) in dichloromethane (3 mL) and pyridine (0.5 mL) was added 1.8 mmol of 6-(4-methylbenzenesulfonyloxy)hexanoyl chloride and the mixture was stirred at room temperature for 12 h. The mixture was diluted with dichloromethane (100 mL), washed with 1N HCl solution (twice) and dried over anhydrous sodium sulfate. Once the solvent was evaporated, 0.8 g of a solid was obtained that was purified by column cromatography (silica gel, hexane: ethyl acetate 20%) to yield 0.53 g of a white solid (60% yield).

IR (KBr) v: 2921, 2851, 1732, 1595, 1462, 1360, 1187, 1176, 1098 cm$^{-1}$; $^1$H-NMR (60 MHz, CDCl$_3$) δ: 0.7–2.0 (complex signal, 41H), 2.25 (m, 2H), 2.4 (s, 3H), 3.3 (m, 4H), 3.9 (m, 7H), 7.35 (d, J=8Hz, 2H), 7.85 (d, J=8Hz, 2H).

(b) Preparation of the Title Compound of this Example

Following the procedure described in example 1f, and using instead of the compound prepared in example 1e, the compound prepared in example 5a, the desired compound was obtained as hemihydrate (65% yield).

mp: 67.6°–72.8° C.; IR (KBr) v: 3420, 3142, 2915, 2847, 1730, 1562, 1463, 1212, 1192, 1143, 1121, 1093, 1035, 1011 cm$^{-1}$.

Analysis calculated for $C_{38}H_{63}NO_7S_2.\frac{1}{2}H_2O$: C 63.5%; H 8.9%; N 1.9%. Found: C 63.89%; H 9.02%; N 2.02%.

EXAMPLE 6

(±)-cis, trans-3-[6-[(4-octadecyloxymethyltetrahydrofuran-2-yl)methoxy]-6-oxohexyl]thiazolium 4-methylbenzenesulfonate (a) 2-octadecyloxymethyl-4-penten-1-ol Following the procedure described in example 1a, and using instead of bromododecane, bromooctadecane, the desired product was obtained as a colorless oil (30% yield).

Rf=0.35 (hexane:ethyl acetate 20%); IR (film) v: 3383, 3071, 2914, 2847, 1636, 1463, 1115, 1038, 910 cm$^{-1}$.; $^1$H-NMR (60 MHz, CDCl$_3$) δ: 0.6–2.2 (complex signal, 38H), 2.9 (m, 1H), 3.45 (m, 6H), 5.0 (m, 2H), 5.6 (m, 1H).

(b) (±)-cis, trans-(4-octadecyloxymethyltetrahydrofuran-2-yl)methanol

Following the procedure described in example 1b, and using instead of the compound prepared in example 1a, the compound prepared in example 6a, the desired product was obtained as a colorless oil (61% yield).

Rf=0.61 (silica gel, hexane:ethyl acetate 1:1); IR (film) v: 3390, 2913, 2846, 1730, 1463, 1372, 1236, 1187, 1043, 720 cm$^{-1}$; $^1$H-NMR (90 Hz, CDCl$_3$) δ: 0.87 (t, J=6.7Hz, 3H), 1.15–1.65 (complex signal, 38H), 2.53 (t, J=6.7Hz, 1H), 3.30–4.15 (complex signal, 9H).

(c) (±)-cis, trans-6-[(4-octadecyloxymethyltetrahydrofuran-2-yl)methoxy]-6-oxohexyl]

Following the procedure described in example 5a, and using instead of the compound prepared in example 1b, the compound prepared in example 6b, the desired product was obtained as a white solid (40% yield).

Rf=0.19 (silica gel, hexane:ethyl acetate 20%); IR (KBr) v: 2921, 2848, 1731, 1595, 1463, 1360, 1176, 1097, 959 cm$^{-1}$; $^1$H-NMR (60 MHz, CDCl$_3$) δ: 0.7–1.8 (complex signal, 46H), 2.25 (t, J=7.2Hz, 2H), 2.33 (s, 3H), 3.2–4.3 (complex signal, 11H), 7.3 (d, J=8Hz, 2H), 7.82 (d, J=8Hz, 2H).

d) Preparation of the Title Compound of This Example

Following the procedure described in example 1f, and using instead of the compound prepared in example 1e, the compound prepared in example 6c, the title compound of this example was obtained as a white solid 70% yield).

mp: 59.9°–68.3° C.; IR (KBr) v: 3442, 3122, 3050, 2914, 2846, 1730, 1463, 1213, 1190, 1122, 1034, 1009 cm$^{-1}$.

Analysis calculated for $C_{40}H_{67}NO_7S$. $4H_2O$: C 59.3%; H 9.2%; N 1.7%. Found: C 58.9%; H 8.87%; N 2.02%.

EXAMPLE 7

(±)-cis, trans-3-[6-oxo-6-[(4-pentadecylaminocarbonyloxymethyltetrahydrofuran-2-yl)methoxy]hexyl]thiazolium 4-methylbenzenesulfonate (a) 2-(pentadecylaminocarbonyloxymethyl)pent-4-en-1-ol A mixture of 2-allyl-1,3-propanediol (1 g, 8.6 mmol) and pentadecylisocyanate (16 mmol) dissolved in 8 mL of pyridine was heated at 60° C. for 3 h under Argon atmosphere. The mixture was cooled, the solvent was evaporated in vacuo and the group was treated with chloroform (75 mL) and 2N HCl solution (25 mL). The aqueous phase was reextracted with chloroform and the combined organic phases were washed with a 5% sodium bicarbonate solution. After drying the organic layer over anhydrous sodium sulfate and evaporating the solvent, 3.8 g of a yellowish solid was obtained that was purified by column chromatography (silica gel, hexane: ethyl acetate 20%) to afford 2.1 g of a white solid (67% yield).

IR (KBr) v: 3328, 3074, 2916, 2846, 1681, 1531, 1465, 1269, 1253, 1236, 1041 cm$^{-1}$; $^1$H-NMR (60 MHz, CDCl$_3$) δ: 0.7–2.3 (complex signal, 34H), 3.15 (m, 2H), 3.6 (m, 2H), 4.15 (m, 2H), 5.0 (m, 2H), 5.5 (m, 1H).

(b) (±)-cis, trans-(4-pentadecylaminocarbonyloxymethyltetrahydrofuran-2-yl)methanol Following the procedure described in example 1b, and using instead of the compound prepared in example 1a, the compound prepared in example 7a, the desired product was obtained as a white solid (90% yield).

Rf=0.13 (silica gel, hexane:ethyl acetate 1:1); mp: 70.4°–70.4° C.; IR (KBr) v: 3350, 2917, 2846, 1682, 1524, 1464, 1249, 1235 cm$^{-1}$; $^1$H-NMR (60 MHz, CDCl$_3$) δ: 0.7–2.1 (complex signal, 32H), 2.7 (m, 1H), 3.15 (m, 2H), 3.6 (m, 2H), 4.0 (m, 5H), 4.9 (m, 1H).

Analysis calculated for $C_{22}H_{43}NO_4$: C 68.5%; H 11.1%; N 3.6%. Found: C 68.80%; H 12.12%; N 3.53%.

(b) (±)-cis, trans-6-oxo-6-[(4-pentadecylaminocarbonyloxymethyltetrahydrofuran-2-yl)methoxy]hexyl 4-methylbenzenesulfonate Following the procedure described in example 5a, and using instead of the compound prepared in example 4b, the compound prepared in example 7b, the desired product was obtained as a white solid (74% yield).

Rf: 0.42 (silica gel, hexane:ethyl acetate 1:1); IR (KBr) v: 3335, 2917, 2847, 1725, 1685, 1595, 1530, 1464, 1361, 1270, 1251, 1237, 1173 cm$^{-1}$; $^1$H-NMR (60 MHz, CDCl$_3$) δ: 0.6–2.0 (complex signal, 38H), 2.25 (t, J=7.3Hz, 2H), 2.45 (s, 3H), 3.2 (m, 2H), 4 (m, 7H), 5.05 (m, 1H), 7.4 (d, J=8Hz, 2H), 7.9 (d, J=8Hz, 2H).

(d) PREPARATION of the TITLE COMPOUND of this EXAMPLE

Following the procedure described in example 1f, and using instead of the compound prepared in example 1e, the compound prepared in example 7c, the title compound of this example was obtained as a white solid (52% yield).

mp: 82.1°–82.8° C.; IR (KBr) ν: 3339, 3139, 2914, 2846, 1727, 1689, 1531, 1464, 1254, 1213, 1192, 1035, 1011, cm$^{-1}$.

Analysis calculated for $C_{38}H_{62}N_2O_8S_2.\frac{1}{2}$ $H_2O$: C 61.2%; H 8.5%; N 3.7%. Found: C 61.13%; H 8.93%; N 3.52%.

EXAMPLE 8

(±)-cis, trans-3-[6-oxo-6-[(4-heptadecylaminocarbonyloxymethyltetrahydrofuran-2-yl)methoxy]hexyl]thiazolium 4-methylbenzenesulfonate Following the procedure described in example 7, but using heptadecylisocyanate instead of pentadecylisocyanate, the title compound of this example was obtained in a similar yield.

EXAMPLE 9

(±)-cis, trans-2-[[[[(4-hexadecyloxymethyltetrahydrofuran-2-yl)methoxy]carbonyl]amino]methyl]]pyridine To a solution of the compound prepared in example 4b (2.26 g, 6.64 mmol) in dichloromethane (30 mL) at 0° C., was added pyridine (1.05 mL) and phenyl chloroformate (0.95 mL) and the resulting mixture was stirred at room temperature for 1 h. Afterwards, the solution was diluted with dichloromethane and washed successively with water and a 1% sodium bicarbonate solution. After drying the organic phase over anhydrous sodium sulfate and evaporating the solvent, 3.2 g of silica gel, hexane:ethyl acetate 1:1).

To the resulting crude dissolved in acetonitrile (15 mL), 2-aminomethylpyridine (0.9 mL) was added and the resulting mixture was refluxed for 12 h. The mixture was cooled, the solvent was evaporated and the residue was treated with chloroform (100 mL) and water (20 mL). The organic phase was washed with 1N sodium hydroxide solution (twice), dried over sodium sulfate and after evaporating the solvent 3.15 g of a yellowish solid were obtained (97% yield).

Rf=0.15 (silica gel, hexane:ethyl acetate 1:1); IR (KBr) ν: 3305, 3053, 2915, 2846, 1673, 1586, 1539, 1466, 1264, 1225 cm$^{-1}$; $^1$H-NMR (90MHz, CDCl$_3$) δ: 0.88 (m, 3H), 1.00–1.85(complex signal, 33H), 2.58 (m, 1H), 3.30–4.26 (complex signal, 9H), 4.50 (d, J=4.8Hz, 2H), 5.58 (m, 1H, NH), 7.26 (m, 2H), 7.66 (t of d, J$_a$=7.6Hz, J$_b$=1.8Hz, 1H), 8.53 (d, J=5.2Hz, 1H).

EXAMPLE 10

(±)-cis, trans-N-ethyl-2-[[[(4-hexadecyloxymethyltetrahydrofuran-2-yl)methoxy]carbonyl]amino]methylpyridinium iodide.

A mixture of the compound prepared in example 9 (0.3 g, 0.61 mmol) and ethyl iodide (2 mL) dissolved in acetonitrile (1 mL) was refluxed under argon atmosphere for 12 h. The mixture was permitted to cool, the solvent was evaporated in vacuo and the residue was recrystallized with dichloromethane and diethyl ether to yield 0.36 g of the title compound of this example as a yellowish solid (90% yield).

mp: 49.0°–50.7° C.; IR (KBr) ν: 3450, 3248, 2913, 2845, 1713, 1625, 1575, 1504, 1463, 1246, 1116 cm$^{-1}$; $^1$H-NMR (90 MHz, CDCl$_3$) δ: 0.87 (m, 3H), 1.20–1.59 (complex signal, 32H), 1.70 (t, J=7.3Hz, 3H), 2.58 (m, 1H), 3.3–4.1 (complex signal, 9H), 4.91 (q, J=7.3Hz, 2H), 4.98 (d, J=5.4Hz, 2H), 6.80 (m, 1H, NH), 7,92 (t of d, J$_a$=5.4 Hz, J$_b$=2.1Hz, 1H), 8.29 (m, 2H), 8,98 (d, J=5.3Hz, 1H).

Analysis calculated for $C_{31}H_{55}IN_2O_4.H_2O$: C 56.0%; H 8.6%; N 4.2%. Found: C 55.91%; H 8.55%; N 4.53%.

EXAMPLE 11

(±)-cis, trans-2-[N-acetyl-[[[(4-hexadecyloxymethyltetrahydrofuran-2-yl)methoxy]carbonyl]amino]methyl pyridine To a solution of the compound prepared in example 9 (1.47 g, 3 mmol) at −40° C., under argon atmosphere, a solution of 1.6M butyl lithium (2.2 mL) was added dropwise. After 5 min., acetic anhydride (1 mL) was added and the mixture was stirred at room temperature for 1 h. The reaction mixture was poured over a saturated solution of ammonium chloride and was extracted several times with ethyl acetate. After drying over anhydrous sodium sulfate and evaporating the solvent 2.2 g of an oil were obtained that was purified by column chromatography (silica gel, hexane:ethyl acetate 45%) to afford 0.9 g of a colorless oil (56% yield).

Rf=0.29 (silica gel, hexane:ethyl acetate 1:1); IR (KBr) ν: 2920, 2850, 1740, 1702, 1590, 1367, 1346, 1207, 1113 cm$^{-1}$; $^1$H-NMR (60MHz, CDCl$_3$) δ: 0.6–2 (complex signal, 34H), 2.4 (s, 3H), 2.8–4 (complex signal, 9H), 4.9 (s, 2H), 6.95 (m, 2H), 7.45 (t, J=7.5Hz, 1H), 8.2 (d, J=5.0Hz, 1H).

EXAMPLE 12

(±)-cis, trans-N-methyl-2-[N-acetyl-[[[(4-hexadecyloxymethyltetrahydrofuran-2-yl)methoxy]carbonyl]amino]methyl]pyridinium iodide A mixture of the compound prepared in example 11 (0.3 g, 0.6 mmol) and methyl iodide (1 mL) dissolved in acetonitrile (3 mL), was heated under argon atmosphere for 12 h. The mixture was permitted to cool, the solvent was evaporated in vacuo and the residue was recrystalized from dichloromethane and diethyl ether, to afford 0.31 g of the title compound of this example as a yellow solid (77% yield).

mp: 44.8°–45.8° C.; IR (KBr) ν: 3437, 2914, 2846, 1740, 1677, 1626, 1464, 1367, 1210, 1115 cm$^{-1}$.

Analysis calculated for $C_{32}H_{55}O_5N_2I.H_2O$: C 55.5%; H 8.2%; N 4.0%. Found: C 55.65%; H 8.29%; N 3.98%.

EXAMPLE 13

(±)-cis, trans-N-ethyl-2-[N-acetyl-[[[(4-hexadecyloxymethyltetrahydrofuran-2-yl)methoxy]carbonyl]amino]methyl]-pyridinium iodide Following the procedure described in example 12, and using ethyl iodide instead of methyl iodide, the title compound of this example was obtained as a yellow solid (72% yield).

mp: 41.3°–42.1° C.; IR (KBr) ν: 3439, 2913, 2846, 1744, 1679, 1625, 1463, 1447, 1427, 1367, 1210, 1115 cm$^{-1}$; $^1$H-NMR (90MHz, CDCl$_3$) δ: 0.93 (m, 3H), 1.25–1.70 (complex signal, 36H), 1.79 (t, J=7.3Hz, 3H), 2.72 (s, 3H), 2.30–4.30 (complex signal, 9H), 5.13 (q, J=7.3Hz, 2H), 5.47 (s, 2H), 7.80 (d, J=7.8Hz, 1H), 8.10 (t, J=6.5Hz, 1H), 8.49 (t of d, J$_a$=7.8Hz, J$_b$=1.5Hz, 1H), 9.80 (d, J=6.0Hz, 1H).

Analysis calculated for $C_{33}H_{57}N_2O_5I.H_2O$: C 56.0%; H 8.4%; N 4.0%. Found: C 56.22%; H 8.71%; N 3.94%.

EXAMPLE 14

(±)-cis, trans-2-[N-ethoxycarbonyl-[[[(4-hexadecyloxymethyltetrahydrofuran-2-yl)methoxy]carbonyl]amino]methyl]pyridinium iodide To a solution of the compound prepared in example 9 (0.81 g, 1.74 mmol) in dichloromethane (5 mL), at 0° C. and under argon atmosphere, ethyl chloroformate (0.18 mL, 1.9 mmol) was added and the mixture was stirred at room temperature for 15 h. Afterwards, 0.4 mL of triethylamine was added, the mixture was diluted with dichloromethane and washed with water. After drying the organic phase over anhydrous sodium sulfate and evaporating the solvent, 0.83 g of an oil was obtained that was purified by column chromatography (silica gel, hexane:ethyl acetate 50%) to yield 0.43 g of a colorless oil (46% yield).

IR (film) v: 2920, 2849, 1793, 1753, 1591, 1463, 1434, 1371, 1338, 1295, 1204, 1109 cm$^{-1}$; $^1$H-NMR (60 MHz, CDCl$_3$) δ: 0.7–2.5 (complex signal, 34H), 3.1–4.4 (complex signal, 14H), 5.0 (s, 2H), 7.18 (m, 2H), 7.52 (t, J=7.4Hz, 1H), 8.52 (d, J=5.0Hz, 1H).

EXAMPLE 15

(±)-cis, trans-N-ethyl-[N-ethoxycarbonyl-[[[(4-hexadecyloxymethyltetrahydrofuran-2-yl)methoxy]carbonyl]amino]methyl]pyridinium iodide Following the procedure described in example 10, and using the compound prepared in example 14, instead of the compound prepared in example 9, the title compound of this example was obtained as a yellow solid (62% yield).

mp: 40.5°–41.5° C.; IR (KBr) v: 3441, 2914, 2846, 1791, 1758, 1696, 1625, 1509, 1463, 1448, 1371, 1340, 1213, 1111 cm$^{-1}$.

Analysis calculated for C$_{34}$H$_{59}$N$_2$O$_6$I.½H$_2$O: C 56.1%; H 8.3%; N 3.9%. Found: C 56.23%; H 8.48%; N 3.92%.

EXAMPLE 16

(±)-cis, trans-2-[N-acetyl-[[[(4-hexadecyloxymethyltetrahydrofuran-2-yl)methoxy]carbonyl]amino]methyl]pyridinium N-oxide To a solution of the compound prepared in example 11 (0.1 g, 0.2 mmol) in dichloromethane (1 mL) cooled with an ice-bath, m-chloroperbenzoic acid (0.26 mmol) was added and the mixture was stirred for 2 h while the temperature of the reaction was rising to room temperature. The mixture was diluted with dichloromethane, washed with 10% sodium thiosulfate and 1N sodium hydroxide. The organic solution was dried over anhydrous sodium sulfate and the solvent was evaporated. The residue was recrystallized from diethyl ether: hexane, to yield 0.07 g of a white solid (68% yield).

Rf=0.11 (silica gel, ethyl acetate); mp: 50.7°–54.7° C.; $^1$H-NMR (90MHz, CDCl$_3$) δ: 0.95 (m, 3H), 0.97–1.50 (complex signal, 34H), 2.32 (m, 3H), 2.57 (s, 3H), 3.20–4.35 (complex signal, 9H), 5.13 (s, 2H), 7.16 (m, 3H), 8.20 (m, 1H).

Analysis calculated for C$_{31}$H$_{52}$N$_2$O$_6$.½H$_2$O: C 66.7%; H 9.5%; N 5.0%. Found: C 66.44%; H 9.47%; N 4.43%.

EXAMPLE 17

(±)-cis, trans-2-[[[[(4-octadecyloxymethyltetrahydrofuran-2-yl)methoxy]carbonyl]amino]methyl]pyridine Following the procedure described in example 9, and using instead of the compound prepared in example 4b, the compound prepared in example 6b, the desired product was obtained as a colorless oil (84% yield).

Rf=0.14 (silica gel, hexane:ethyl acetate 1:1); IR (film) v: 3303, 3053, 2914, 2845, 1673, 1587, 1539, 1465, 1263, 1120, 1053 cm$^{-1}$; $^1$H-NMR (90MHz, CDCl$_3$) δ: 0.7–2.2 (complex signal, 38H), 2.53 (t, J=7.8Hz, 2H), 3.2–4.2 (complex signal, 9H), 4.49 (d, J=5.6Hz, 2H), 6.0 (m, 1H, NH), 7.29 (m, 2H), 7.60 (t, J=6.2Hz, 1H), 8.52 (d, J=4.0Hz, 1H).

EXAMPLE 18

(±)-cis, trans-2-[N-acetyl-[[[(4-octadecyloxymethyltetrahydrofuran-2-yl)methoxy]carbonyl]amino]methyl]pyridine Following the procedure described in example 11, and using instead of the compound prepared in example 9, the compound prepared in example 17, the desired product was obtained as a colorless oil (37% yield).

Rf=0.24 (hexane:ethyl acetate 1:1); IR (film) v: 2921, 2849, 1739, 1701, 1589, 1431, 1367, 1207, 1114 cm$^{-1}$.

EXAMPLE 19

(±)-cis, trans-N-methyl-2-[N-acetyl-[[[(4-octadecyloxymethyltetrahydrofuran-2-yl)methoxy]carbonyl]amino]methyl]pyridinium iodide Following the procedure described in example 12, and using instead of the compound prepared in example 11, the compound prepared in example 18, the title compound of this example was obtained as a whiteyellowish solid (77% yield).

mp: 56.6°–57.6° C.; IR (KBr) v: 3442, 2913, 2846, 1740, 1676, 1626, 1463, 1367, 1211, 1116 cm$^{-1}$.

Analysis calculated for C$_{34}$H$_{59}$IN$_2$O$_5$. H$_2$O: C 56.6%; H 8.5%; N 3.9%. Found: C 56.92%; H 8.45%; N 3.85%.

EXAMPLE 20

(±)-cis, trans-N-ethyl-2-[N-acetyl-[[[(4-octadecyloxymethyltetrahydrofuran-2yl)methoxy]carbonyl]amino]methyl]pyridinium iodide Following the procedure described in example 10, and using instead of the compound prepared in example 9, the compound prepared in example 18, the titled compound of this example was obtained as a yellow solid (72% yield).

mp: 53.4°–53.9° C.; IR (KBr) v: 3445, 2914, 2846, 1744, 1676, 1625, 1464, 1367, 1211, 1116 cm$^{-1}$; $^1$H-NMR (90MHz, CDCl$_3$) δ: 0.87 (m, 3H), 1.1–2.0 (complex signal, 38H), 1.74 (t, J=7.2Hz, 3H), 2.66 (s, 3H), 3.2–4.3 (complex signal, 9H), 5.08 (q, J=7.2Hz, 2H), 5.41 (s, 2H), 7.75 (d, J=8.4Hz, 1H), 8.10 (t, J=6.6Hz, 1H), 8.49 (t, J=7.8Hz, 1H), 9.78 (d, J=5.8Hz, 1H).

Analysis calculated for C$_{35}$H$_{61}$IN$_2$O$_5$.½H$_2$O: C 57.9%; H 8.6%; N 3.9%. Found: C 57.72%; H 8.68%; N 3.75%.

EXAMPLE 21

(±)-cis, trans-2-[N-methyl-[[[(4-octadecyloxymethyltetrahydrofuran-2-yl)methoxy]carbonyl]amino]methyl pyridine To a solution of the compound prepared in example 17 (0.8 g, 1.5 mmol) in anhydrous tetrahydrofuran, under argon atmosphere and at −40° C., a 1.6M butyl lithium solution (1.2 mL, 1.9 mmol) was added dropwise. After 5 min., methyl iodide (0.5 mL) was added and the mixture was stirred for 30 min. while the temperature was rising to room temperature. The mixture was poured over a saturated solution of ammonium chloride (10 mL), was extracted with ethyl acetate and the organic phase was dried over anhydrous sodium sulfate. After evaporating the solvent, 0.78 g of a waxy solid was obtained that was purified by column chromatography (silica gel, hexane:ethyl acetate 1:1), to yield 0.4 g of the title compound of this example.

IR (film) v: 2920, 2850, 1702, 1589, 1567, 1463, 1433, 1401, 1212, 1114 cm$^{-1}$; $^1$H-NMR (90MHz, CDCl$_3$) δ: 0.90 (m, 3H), 1.1–2.6 (complex signal, 38H), 2.98 (s, 3H), 3.25–4.20 (complex signal, 9H), 4.61 (s, 2H), 7.24 (m, 2H), 7.68 (t of d, $J_a$=7.4Hz, $J_b$=1.9Hz, 1H), 8.55 (d, J=4.8Hz, 1H).

EXAMPLE 22

(±)-cis, trans-N-methyl-2-[N-methyl-[[[(4-octadecyloxymethyltetrahydrofuran-2-yl)methoxy]carbonyl]amino]-methyl]pyridinium iodide Following the procedure described in example 12, and using instead of the compound prepared in example 11, the compound prepared in example 21, the title compound of this example was obtained with a similar yield

EXAMPLE 23

(±)-cis, trans-[[[[(4-tetradecyloxymethyltetrahydrofuran-2-yl)methoxy]carbonyl]amino]methyl pyridine Following the procedure described in example 9, and using instead of the compound prepared in example 4b, the compound prepared in example 2b, the title compound of this example was obtained as a white solid (quantitative yield).

Rf=0.15 (silica gel, hexane:ethyl acetate 1:1); IR (KBr) v: 3304, 3053, 2952, 2915, 2846, 1673, 1587, 1539, 1464, 1264, 1121 cm$^{-1}$; $^1$H-NMR (90MHz, CDCl$_3$) δ: 0.87 (m, 3H), 1.10–1.70 (complex signal, 29H), 2.57 (m, 1H), 3.20–4.35 (complex signal, 9H), 4.48 (d, J=5.6Hz, 2H), 6.07 (m, 1H, NH), 7.20 (m, 2H), 7.65 (t of d, $J_a$=7.6Hz, $J_b$=1.8Hz, 1H), 8,53 (d, J=5.2Hz, 1H).

EXAMPLE 24

(±)-cis, trans-[N-acetyl-[[[(4-tetradecyloxymethyltetrahydrofuran-2-yl)methoxy]carbonyl]amino]methyl]pyridine To a solution of the compound prepared in example 23 (3.21 g, 6.9 mmol) in dichloromethane (20 mL) at 0° C., acetyl chloride (0.64 mL), 9 mmol) was added and the mixture was stirred at room temperature for 2 days. Triethylamine (1.9 mL) was added, the solvents were evaporated and the crude was chromatographed (silica gel, hexane:ethyl acetate 50%), to yield the title compound of this example as a colorless oil (64% yield).

Rf=0.52 and 0.47 (cis and trans isomers, silica gel, hexane:ethyl acetate 1:3); IR (film) v: 2921, 2850, 1739, 1700, 1589, 1567, 1431, 1367, 1207 cm$^{-1}$; $^1$H-NMR (90 MHz, CDCl$_3$) δ: 0.85 (m, 3H), 0.95–1.70 (complex signal, 29H), 2.28 (m, 1H), 2.51 (s, 3H), 3.10–4.20 (complex signal, 9H), 4.99 (s, 2H), 7.02 (m, 3H), 7.50 (t, J=7.5Hz, 1H), 8.39 (d, J=5.0Hz, 1H).

EXAMPLE 25

(±)-cis, trans-N-ethyl-2-[N-acetyl-[[[(4-tetradecyloxymethyltetrahydrofuran-2-yl)methoxy]carbonyl]amino]-methyl]-pyridinium chloride.

Following the procedure described in example 10, and using instead of the compound prepared in example 9, the compound prepared in example 24, the iodide of title compound of this example was obtained as a yellow solid. This solid was treated with an IRA-410 ion exchange resin (Cl$^-$form) (eluent:methanol/water: 7/3) and the resulting chloride was recrystallized in acetone (66% yield). mp: 43.5°–86.4° C.; IR (KBr) v: 3389, 2919, 2848, 1744, 1680, 1626, 1367, 1214, cm$^{-1}$; $^1$H-NMR (90 MHz, CDCL$_3$) δ: 0.88 (m, 3H), 1.26 (m, 28H), 1.73 (t, J=7.1Hz, 3H), 2.6 (m, 1H), 2.66 (s, 3H), 3.20–4.28 (complex signal, 9H), 5.28 (q, J=7.2Hz, 2H), 5.38 (s, 2H), 7.64 (d, J=7.8Hz, 1H), 8.02 (t, J=6.6Hz, 1H), 8.34 (t, J=7.8Hz, 1H), 10.30 (d, J=5.7Hz, 1H).

Analysis calculated for C$_{33}$H$_{57}$N$_2$O$_5$Cl.H$_2$O: C 64.4%; H 9.6%; N 4.6%. Found: C 64.70%; H 9.73%; N 4.61%.

EXAMPLE 26

(±)-cis, trans-3-[[[[(4-octadecyloxymethyltetrahydrofuran-2-yl) methoxy]carbonyl]amino]methyl]pyridine Following the procedure described in example 9, and using instead of the compound prepared in example 4b, the compound prepared in example 6b, and instead of 2-aminomethylpyridine, 3-aminomethylpyridine a yellowish solid was obtained (quantitative yield).

Rf=0.08 (silica gel, hexane:ethyl acetate 1:3); IR (KBr) v: 3301, 2914, 2845, 1675, 1539, 1466, 1260, 1120, cm$^{-1}$; $^1$H-NMR (90 MHZ, CDCl$_3$) δ: 0.87 (m, 3H), 1.26 (m, 38H), 2.50 (m, 1H), 3.2–4.3 (complex signal, 9H), 4.33 (d, J=6.4Hz, 2H), 6.3 (t, J=5.2Hz, 1H), 7.15 (m, 1H), 7.60 (d, J=7.2Hz, 1H), 8.45 (m, 2H).

EXAMPLE 27

(±)-cis, trans-3-[N-acetyl-[[[(4-octadecyloxymethyltetrahydrofuran-2-yl)methoxy]carbonyl]amino]methyl]pyridine Following the procedure described in example 11, and using instead of the compound prepared in example 9, the compound prepared in example 26, the desired product was obtained as a colorless oil (34% yield).

Rf=0.27 (silica gel, hexane:ethyl acetate 1:3); IR (film) v: 2921, 2850, 1739, 1702, 1367, 1206, 1115 cm$^{-1}$; $^1$H-NMR (90MHz, CDCl$_3$) δ: 0.85–1.6 (complex signal, 38H), 2.55 (s, 3H), 3.3–4.2 (complex signal, 9H), 4.95 (s, 2H), 7.21 (m, 1H), 7.70 (d, J=7.9Hz, 1H), 8.60 (m, 2H).

EXAMPLE 28

(±)-cis,
trans-N-ethyl-3-[N-acetyl-[[[(4-octadecyloxymethyltetrahydrofuran-2-yl)methoxy]carbonyl]amino]methyl]-pyridinium iodide Following the procedure described in example 10, and using instead of the compound prepared in example 9, the compound prepared in example 27, the title compound of this example was obtained as a yellow solid (52% yield).

mp: 52.5°–59.0° C.; IR (KBr) v: 3443, 2913, 2846, 1740, 1673, 1628, 1464, 1367, 1212 cm$^{-1}$.

Analysis calculated for $C_{35}H_{61}IN_2O_5 \cdot H_2O$: C 57.2%; H 8.6%; N 3.8%. Found: C 57.20%; H 8.41%; N 3.60%.

EXAMPLE 29

(±)-cis,
trans-4-[[[[(4-octadecyloxymethyltetrahydrofuran-2-yl)methoxy]carbonyl]amino]methyl]pyridine Following the procedure described in example 9, and using instead of the compound prepared in example 4b, the compound prepared in example 6b, and instead of 2-aminomethylpyridine, 4-aminomethylpyridine, a white solid was obtained (quantitative yield).

Rf=0.05 (silica gel, hexane: ethyl acetate 1:1), mp: 52.3°–53.8° C.; IR (KBr) v: 3304, 3067, 2913, 2845, 1681, 1598, 1562, 1465, 1265, 1120 cm$^{-1}$; $^1$H-RMN (90MHz, CDCl$_3$) δ: 0.89 (m, 3H), 1.1–2.2 (complex signal, 37H), 2.58 (m, 1H), 3.40 (t, J=7.6Hz, 4H), 3.9 (m, 3H), 4.38 (d, J=6.6Hz, 2H), 5.45 (t, J=6.4Hz, 1H), 7.21 (d, J=6Hz, 2H), 8.55 (d, J=6Hz, 2H).

Analysis calculated for $C_{31}H_{54}N_2O_4 \cdot \frac{1}{2}H_2O$; C 71.2%; H 10.4%; N 5.4%. Found: C71.04%; H 10.46%; N 5.04%.

EXAMPLE 30

(±)-cis,
trans-N-ethyl-4-[[[[(4-octadecyloxymethyltetrahydrofuran-2-yl)methoxy]carbonyl]amino]methyl]-pyridinium iodide Following the procedure described in example 10, and using instead of the compound prepared in example 9, the compound prepared in example 29, the title compound of this example was obtained as a yellow solid (74% yield).

mp: 57.7°–61.0° C.; IR (KBr) v: 3456, 3320, 2913, 2845, 1710, 1637, 1514, 1463, 1248, 1117 cm$^{-1}$; $^1$H-NMR (90MHz, CDCl$_3$) δ: 0.89 (m, 3H), 1.28 (m, 38H), 1.72 (t, J=7.2Hz, 3H), 2.61 (m, 1H), 3.30–4.13 (complex signal, 9H), 4.68 (m, 2H), 4.90 (q, J=7.2Hz, 2H), 6.46 (m, 1H), 8.07 (d, J=6.4Hz, 2H), 9.11 (d, J=6.4Hz, 2H).

Analysis calculated for $C_{33}H_{59}IN_2O_4 \cdot \frac{1}{2}H_2O$: C 57.9%; H 8.8%; N 4.1%. Found: C 57.43%; H 8.85%; N 3.89%.

EXAMPLE 31

(±)-cis,
trans-4-[N-acetyl-[[[(4-octadecyloxymethyltetrahydrofuran-2-yl)methoxy]carbonyl]amino]methyl]pyridine Following the procedure described in example 11, and using instead of the compound prepared in example 9, the compound prepared in example 29, a colorless oil was obtained (11% yield).

Rf=0.12 (silica gel, hexane: ethyl acetate 1:1); IR (film) v: 2919, 2849, 1740, 1702, 1598, 1367, 1318, 1213, 1197, 1115 cm$^{-1}$. $^1$H-NMR (90 MHz, CDCl$_3$)δ: 0.88 (m, 3H), 1.0–1.8 (complex signal, 34H), 2.58 (s, 3H), 3.2–4.16 (complex signal, 9H), 4.94 (s, 2H), 7.18 (d, J=6.3Hz, 2H), 8.52 (d, J=6.3Hz, 2H).

EXAMPLE 32

(±)-cis,
trans-N-ethyl-4-[N-acetyl-[[[(4-octadecyloxymethyltetrahydrofuran-2-yl)methoxy]carbonyl]amino]-methyl]-pyridinium iodide Following the procedure described in example 10, and using instead of the compound prepared in example 9, the compound prepared in example 31, the title compound of this example was obtained as a yellow solid (31% yield).

mp: 51.6°–54.4° C.; IR (KBr) v: 3451, 2913, 2846, 1737, 1673, 1638, 1464, 1367, 1212, 1117 cm$^{-1}$.

Analysis calculated for $C_{35}H_{61}IN_2O_5 \cdot H_2O$: C 57.2%; H 8.6%; N 3.8%. Found: C 57.47%; H 8.57%; N 3.63%.

EXAMPLE 33

(±)-cis,
trans-4-[[[(4-octadecyloxymethyltetrahydrofuran-2-yl)methoxy]carbonyl]amino]pyridine To the carbonate prepared starting from the compound obtained in example 6b (1.2 g, 3.37 mmol), phenyl chloroformate (0.46 mL, 3.7 mmol) and pyridine (0.5 mL), was added 4-aminopyridine (0.450 g, 4.5 mmol) and 2 ml of pyridine. The mixture was refluxed, under argon atmosphere for 2 days. The mixture was cooled, diluted with chloroform and washed with water and a 2N sodium hydroxide solution. The organic phase was dried over anhydrous sodium sulfate and the solvent was evaporated to yield 1.4 g of crude that was purified by chromatography (silica gel, ethyl acetate) to give 0.28 g of a white solid (16% yield).

mp: 80.0°–85.7° C.; IR (KBr) v: 3246, 3163, 2914, 2847, 1730, 1625, 1592, 1541, 1464, 1332, 1247, 1224, 1118 cm$^{-1}$. $^1$H-NMR (90 MHz, CDCl$_3$) δ: 0.90 (m, 3H), 1.0–2.1 (complex signal, 33H), 2.55 (q, J=6.5Hz, 2H), 3.3–4.2 (complex signal, 9H), 7.34 (d, J=6.0Hz, 2H), 8.05 (s, 1H), 8.45 (d, J=6.0Hz, 2H).

Analysis calculated for $C_{30}H_{52}N_2O_4$: C 71.4%; H 10.3%; N 5.5%. Found: C 71.51%; H 10.69%; N 5.35%.

EXAMPLE 34

(±)-cis,
trans-N-ethyl-4-[[[(4-octadecyloxymethyltetrahydrofuran-2-yl)methoxy]carbonyl]amino]pyridinium iodide Following the procedure described in example 10, and using instead of the compound prepared in example 9, the compound prepared in example 33, a white-yellowish solid was obtained (88% yield). mp: 118°–123.0° C.

Analysis calculated for $C_{32}H_{57}IN_2O_4 \cdot \frac{1}{2}H_2O$: C 57.3%; H 8.6%; N 4.2%. Found: C 57.55%; H 8.66%; N 4.02%.

EXAMPLE 35

(±)-cis,
trans-4-[[[(4-hexadecyloxymethyltetrahydrofuran-2-yl)methoxy]carbonyl]amino]pyridine Following the procedure described in example 33, and using instead of the compound prepared in example 6b, the compound prepared in example 4b, the title compound of this example was obtained as a white solid (44% yield).

Rf=0.08 (silica gel, hexane:ethyl acetate 1:1); IR (KBr) v: 3164, 2916, 2847, 1730, 1624, 1592, 1541, 1464, 1332, 1307, 1247, 1224 cm$^{-1}$; $^1$H-NHR (90 MHz, CDCl$_3$) δ: 0.89 (m, 3H), 1.27 (m, 31H), 2.60 (m, 1H), 3.30–4.25 (complex signal, 9H), 7.27 (m, 1H, NH), 7.32 (dd, J$_a$=4.8Hz, J$_b$=1.6Hz, 2H), 8.47 (dd, J$_a$=4.8Hz, J$_b$=1.6Hz, 2H).

EXAMPLE 36

(±)-cis, trans-4-[N-acetyl-[[(4-hexadecyloxymethyltetrahydrofuran-2-yl)methoxy]carbonyl]amino]pyridine Following the procedure described in example 24, and using instead of the compound prepared in example 23, the compound prepared in example 35, the title compound of this example was obtained as a white solid (43% yield).

Rf=0.19 (silica gel, hexane:ethyl acetate 1:1); IR (KBr) v: 3440, 2923, 2850, 1743, 1714, 1636, 1456, 1369, 1259 cm$^{-1}$; $^1$H-NMR (90MHz, CDCl$_3$) δ: 0.90 (m, 3H), 1.24 (m, 31H), 2.3 (m, 2H), 2.61 (s, 3H), 3.17–4.16 (complex signal, 9H), 7.10 (d, J=4.9Hz, 2H), 8.65 (m, J=4.9 Hz, 2H).

EXAMPLE 37

(±)-cis, trans-N-ethyl-4-[N-acetyl-[[(4-hexadecyloxymethyltetrahydrofuran-2-yl)methoxy]carbonyl]amino]pyridinium iodide Following the procedure described in example 10, and using instead of the compound prepared in example 9, the compound prepared in example 36, the title compound of this example was obtained as a white solid (57% yield). mp: 43.9°–73.5° C.; IR (KBr) v: 3442, 2913, 2846, 1745, 1695, 1633, 1512, 1463, 1253 cm$^{-1}$.

Analysis calculated for C$_{32}$H$_{55}$IN$_2$O$_5$.H$_2$O: C 55.5%; H 8.2%; N 4.0%. Found: C 55.61%; H 7.90%; N 3.86%.

EXAMPLE 38

(±)-cis, trans-3-[[[(4-hexadecyloxymethyltetrahydrofuran-2-yl)methoxy]carbonyl]amino]pyridine Following the procedure described in example 33, and using instead of 4-aminopyridine, 3-aminopyridine, and instead of the compound prepared in example 6b, the compound prepared in example 4b, the title compound of this example was obtained as a white solid (36% yield).

Rf=0.16 (silica gel, hexane:ethyl acetate 1:1); IR (KBr) v: 3241, 3185, 2918, 2845, 1721, 1613, 1584, 1556, 1428, 1222, 1113 cm$^{-1}$.

EXAMPLE 39

(±)-cis, trans-3-[N-acetyl-[[(4-hexadecyloxymethyltetrahydrofuran-2-yl)methoxy]carbonyl]amino]pyridine Following the procedure described in example 24, and using instead of the compound prepared in example 23, the compound prepared in example 38, a colorless oil was obtained (44% yield).

Rf=0.19 and 0.24 (cis and trans isomers, silica gel, hexane:ethyl acetate 1:1); IR (film) v: 2915, 2847, 1740, 1702, 1575, 1464, 1419, 1295, 1115 cm$^{-1}$; $^1$H-NMR (90 MHz, CDCl$_3$) δ: 0.87 (m, 3H), 1.26 (m, 31H), 2.20 (m, 2H), 2.66 (s, 3H), 3.1–4.4 (complex signal, 9H), 7.44 (m, 2H), 8.40 (dd, J$_a$=2.3Hz, J$_b$=0.9Hz, 1H), 8.57 (dd, J$_a$=4.4Hz, J$_b$=1.8Hz, 1H).

EXAMPLE 40

(±)-cis, trans-N-ethyl-3-[N-acetyl-[[(4-hexadecyloxymethyltetrahydrofuran-2-yl)methoxy]carbonyl]amino]pyridinium iodide Following the procedure described in example 10, and using instead of the compound prepared in example 9, the compound prepared in example 39, the title compound of this example was obtained as a yellow solid (56% yield).

mp: 43.8°–45.0° C.; IR (KBr) v: 3456, 2913, 2846, 1753, 1692, 1631, 1497, 1255, 1111 cm$^{-1}$.

Analysis calculated for C$_{32}$H$_{55}$IN$_2$O$_5$.H$_2$O :C 55.5%; H 8.2%; N 4.0%. Found: C 55.39%; H 8.11%; N 3.95%.

EXAMPLE 41

(±)-cis, trans-3-[2-[[[(4-hexadecyloxymethyltetrahydrofuran-2-yl)methoxy]carbonyl]amino]ethyl]thiazolium 4-methylbenzensulfonate (a) (±)-cis, trans-2-[[[(4-hexadecyloxymethyltetrahydrofuran-2-yl)methoxy]carbonyl]amino]ethan-1-ol Following the procedure described in example 9, and using instead of 2-aminomethylpyridine, 2-aminoethanol, the title compound of this example was obtained as a colorless oil (quantitative yield).

Rf: 0.12 (silica gel, hexane:ethyl acetate 1:1); IR (film): 3309, 2916, 2847, 1683, 1542, 1462, 1279, 1119 cm$^{-1}$. $^1$H-NMR (90MHz, CDCl$_3$) δ: 0.88 (m, 3H), 1.25 (m, 33H), 2.55 (m, 1H), 3.20–4.25 (complex signal, 13H), 5.60 (m, 1H).

(b) (±)-cis, trans-2-[[[(4-hexadecyloxymethyltetrahydrofuran-2-yl)methoxy]carbonyl]amino]ethan-1-yl 4-methylbenzenesulfonate To the compound prepared in the example 41a (1.65 g, 3.8 mmol) dissolved in triethylamine (5 mL) at 0° C., 4-methylbenzenesulfonyl chloride (0.87 g, 4.6 mmol) was added and the mixture was stirred at room temperature for 18 h. The solvents were evaporated and the crude was chromatographed (silica gel, hexane: ethyl acetate 30%) to yield 1.05 g of a white-yellowish solid (48% yield).

IR (KBr) v: 3389, 2913, 2846, 1714, 1595, 1528, 1493, 1464, 1352, 1290, 1252, 1174 cm$^{-1}$. $^1$H-NMR (90 MHz, CDCl$_3$) δ: 0.80 (m, 3H), 1.19 (m, 33H), 2.35 (s, 3H), 2.42 (m, 1H), 3.20–4.10 (complex signal, 13H), 5.35 (m, 1H, NH), 7.25 (d, J=8.0Hz, 2H), 7.70 (d, J=8.0Hz, 2H).

(c) Preparation of the title compound of this example

Following the procedure described in example 1f, and using instead of the compound prepared in example 1e, the compound prepared in example 41b, the title compound of this example was obtained as a white solid (46% yield).

mp: 40.1°–40.5° C.; IR (KBr) v: 3442, 3065, 2913, 2846, 1702, 1537, 1463, 1189, 1126, 1011 cm$^{-1}$; $^1$H-NMR (90 MHz, CDCl$_3$) δ: 0.86 (m, 3H), 1.24 (m, 29H), 2.33 (s, 3H), 2.35 (m, 1H), 3.25–3.93 (complex signal, 9H), 4.85 (m, 2H), 7.0 (m, 1H), 7.15 (d, J=8.1Hz, 2H), 7.73 (d, J=8.1Hz, 2H), 8.02 (m, 1H), 8.36 (d, J=3.2Hz, 1H), 10.52 (s, 1H).

Analysis calculated for $C_{35}H_{58}N_2S_2O_7.\frac{1}{2}H_2O$: C 60.8%; H 8.5%; N 4.0%. Found: C 60.51%; H 8.49%; N 3.92%.

EXAMPLE 42

(±)-cis, trans-3-[2-[N-acetyl-[[(4-hexadecyloxymethyltetrahydrofuran-2-yl)methoxy]carbonyl]amino]ethyl]thiazolium 4-methylbenzenesulfonate (a) (±)-cis, trans-2-[N-acetyl-[[[(4-hexadecyloxymethyltetrahydrofuran-2-yl)methoxy]carbonyl]amino]ethan-1-yl 4-methylbenzenesulfonate Following the procedure described in example 24, and using instead of the compound prepared in example 23, the compound prepared in example 41b, the desired compound was obtained in a similar yield.

(b) Preparation of the Title Compound of this Example

Following the procedure described in example 1f, and using instead of the compound prepared in example 1e, the compound prepared in example 42a, the title compound of this example was obtained in a similar yield.

EXAMPLE 43

(±)-cis, trans-2-[2-[[[(4-hexadecyloxymethyltetrahydrofuran-2-yl)methoxy]carbonyl]amino]ethyl]pyridine Following the procedure described in example 9, and using instead of 2-aminomethylpyridine, 2-(2-aminoethyl)pyridine, the title compound of this example was obtained as a white solid (quantitative yield).

Rf=0.08 (silica gel, hexane:ethyl acetate 1:1); IR (KBr) ν: 3225, 3050, 2914, 2845, 1710, 1591, 1566, 1466, 1265 cm$^{-1}$; $^1$H-NMR (90 MHz, CDCl$_3$) δ: 0.94 (m, 3H), 1.26 (m, 33H), 2.58 (q, J=6.6Hz, 1H), 2.94 (t, J=6.4Hz, 2H), 3.20–4.09 (complex signal, 13H), 5.9 (m, 1H, NH), 7.08 (m, 2H), 7.57 (t of d, $J_a$=7.6Hz, $J_b$=1.8Hz, 1H), 8.50 (d, J=5.2Hz, 1H).

EXAMPLE 44

(±)-cis, trans-N-ethyl-2-[2-[[[(4-hexadecyloxymethyltetrahydrofuran-2-yl)methoxy]carbonyl]amino]ethyl]pyridinium iodide Following the procedure described in example 10, and using instead of the compound prepared in example 9, the compound prepared in example 43, the title compound of this example was obtained as a yellow solid (53% yield).

mp=52.2°–54.1° C.; IR (KBr) ν: 3431, 3290, 2913, 2846, 1702, 1625, 1505, 1463, 1254, 1116 cm$^{-1}$.

Analysis calculated for $C_{32}H_{57}IN_2O_4.\frac{1}{2}H_2O$: C 57.3%; H 8.7%; N 4.2%. Found: C 57.19%; H 8.74%; N 4.10%.

EXAMPLE 45

(±)-cis, trans-2-[2-[N-acetyl-[[(4-hexadecyloxymethyltetrahydrofuran-2-yl)methoxy]carbonyl]amino]ethyl]pyridine Following the procedure described in example 24, and using instead of the compound prepared in example 23, the compound prepared in example 43, the title compound of this example was obtained as a colorless oil (35% yield).

Rf: 0.45 and 0.39 (cis and trans isomers, silica gel, hexane: ethyl acetate 1:3); IR (film) ν: 2921, 2850, 1735, 1698, 1588, 1449, 1431, 1387, 1179 cm$^{-1}$; $^1$H-NMR (90 MHz, CDCl$_3$) δ: 0.88 (m, 3H), 1.26 (m, 33H), 2.49 (s, 3H), 2.64 (q, J=6.5Hz, 1H), 3.05 (dd, $J_a$=9.6Hz, $J_b$=6.5Hz, 2H), 3.35 (m, 4H), 3.68 (m, 2H), 4.15 (m, 5H), 7.19 (m, 2H), 7.59 (t of d, $J_a$=7.6Hz, $J_b$=1.9Hz, 1H), 8,51 (d, J=4.9Hz, 1H).

EXAMPLE 46

(±)-cis, trans-N-ethyl-2-[2-[N-acetyl-[[(4-hexadecyloxymethyltetrahydrofuran-2-yl)methoxy]carbonyl]amino]methyl]pyridinium iodide Following the procedure described in example 10, and using instead of the compound prepared in example 9, the compound prepared in example 45, the title compound of this example was obtained as a yellow solid (53% yield).

mp: 37.1°–40.0° C.; IR (KBr) ν: 3442, 2917, 2848, 1738, 1673, 1462, 1186 cm$^{-1}$.

Analysis calculated for $C_{34}H_{59}O_5N_2.\frac{1}{2}H_2O$: C 57.4%; H 8.4%; N 3.9%. Found: C 57.83%; H 8.50%; N 3.81%.

EXAMPLE 47

(±)-cis, trans-2-[[[[(4-pentadecylaminocarbonyloxymethyltetrahydrofuran-2-yl)methoxy]carbonyl]amino]methyl]pyridine Following the procedure described in example 9, and using instead of the compound prepared in example 4b, the compound prepared in example 7b, a white solid was obtained (66% yield).

Rf=0.23 (silica gel, ethyl acetate); mp=75.5°–79.6° C.; IR (KBr) ν: 3320, 3051, 2915, 2847, 1681, 1532, 1262, cm$^{-1}$. $^1$H-NMR (90MHz, CDCl$_3$) δ: 0.88 (m, 3H), 0.5–1.90 (complex signal, 28H), 2.55 (m, 1H), 3.14 (m, 2H), 3.7 (m, 1H), 4.00 (m, 5H), 4.48 (d, J=5.6Hz, 2H), 5.1 (m, 1H, NH), 6.2 (m, 1H, NH), 7.23 (m, 2H), 7.60 (t of d, $J_a$=7.4Hz, $J_b$=1.6Hz, 1H), 8.50 (d, J=4.6Hz, 1H).

Analysis calculated for $C_{29}H_{49}N_3O_5$: C 67.0%; H 9.4%; N 8.0%. Found: C 67.34%; H 9.57%; N 7.80%.

EXAMPLE 48

(±)-cis, trans-2-[N-acetyl-[[[(4-pentadecylaminocarbonyloxymethyltetrahydrofuran-2-yl)methoxy]carbonyl]amino]methylpyridine Following the procedure described in example 24, and using instead of the compound prepared in example 33, the compound prepared in example 47, a white solid was obtained (63% yield).

Rf=0.23 (silica gel, hexane:ethyl acetate 1:3); $^1$H-NMR (90MHz, CDCl$_3$) δ: 0.90 (m, 3H), 1.05–2.20 (complex signal, 28H), 2.50 (m, 1H), 2.63 (s, 3H), 3.15 (q, J=5.7Hz, 2H), 3.52 (t, J=6.4Hz, 1H), 3.90 (m, 5H), 4.77 (m, 1H, NH), 5.10 (s, 2H), 7.16 (m, 2H), 7.63 (t, J=8.6Hz, 1H), 8.50 (d, J=4.0Hz, 1H).

EXAMPLE 49

(±)-cis,
trans-N-ethyl-2-[N-acetyl-[[[(4-pentadecylaminocarbonyloxymethyltetrahydrofuran-2-yl)methoxy]-carbonyl]amino]methyl]pyridinium iodide Following the procedure described in example 10, and using instead of the compound prepared in example 9, the compound prepared in example 48, a yellow solid was obtained (44% yield). mp: 34.2°–37.8° C.

Analysis calculated for $C_{33}H_{56}IN_3O_6.H_2O$: C 53.8%; H 7.9%; N 5.7%. Found: C 53.98%; H 7.83%; N 5.63%.

EXAMPLE 50

(±)-cis,
trans-2-[[[[(4-heptadecylaminocarbonyloxymethyltetrahydrofuran-2-yl)methoxy]carbonyl]amino]methyl]-pyridine Following the procedure described in example 9, and using instead of the compound prepared in example 7b, an alcohol obtained starting from heptadecylisocyanate and prepared in a similar way to the alcohol in example 7b, a white solid was obtained (quantitative yield).

Rf: 0.23 (silica gel, ethyl acetate); mp: 77.1°–81.2° C.; IR (KBr) ν: 3320, 3050, 2914, 2846, 1680, 1531, 1465, 1263, cm$^{-1}$; $^1$H-NMR (90MHz, CDCl$_3$) δ: 0.86 (m, 3H), 1.24 (m, 35H), 2.55 (q, J=6.7Hz, 1H), 3.15 (q, J=7.2Hz, 2H), 3.40–4.40 (complex signal, 7H), 4.46 (d, J=5.6Hz, 2H), 5.00 (m, 1H, NH), 6.10 (m, 1H, NH), 7.21 (m, 2H), 7.62 (t of d, J$_a$=7.4Hz, J$_b$=1.6Hz, 1H), 8.49 (d, J=4.6Hz, 1H).

Analysis calculated for $C_{31}H_{53}N_3O_5$: C 68.0%; H 9.7%; N 7.7%. Found: C 67.70%; H 9.53%; N 8.00%.

EXAMPLE 51

(±)-cis,
trans-2-[[[[(4-heptadecylaminocarbonyloxymethyltetrahydrofuran-2-yl)methoxy]carbonyl]amino]methyl]-pyridinium iodide Following the procedure described in example 10, and using instead of the compound prepared in example 9, the compound prepared in example 50, a white solid was obtained (88% yield).

mp 52.7°–54.8° C.; IR (KBr) ν: 3331, 2913, 2846, 1706, 1625, 1524, 1463, 1247 cm$^{-1}$.

Analysis calculated for $C_{33}H_{58}IN_3O_5.1\frac{1}{2}H_2O$: C 54.2%; H 8.3%; N 5.8%. Found: C 54.15%; H 7.96%; N 5.93%.

EXAMPLE 52

(±)-cis,
trans-2-[N-acetyl-[[[(4-heptadecylaminocarbonyloxymethyltetrahydrofuran-2-yl)methoxy]-carbonyl]amino]methyl]pyridine Following the procedure described in example 24, and using instead of the compound prepared in example 23, the compound prepared in example 50, the title compound of this example was obtained as a white-pink solid (78% yield).

Rf=0.44 (silica gel, ethyl acetate); mp: 49.5°–49.6° C.; IR (KBr) ν: 3365, 2919, 2846, 1740, 1687, 1518, 1377, 1333, 1228 cm$^{-1}$; $^1$H-NMR (90MHz, CDCl$_3$) δ: 0.88 (m, 3H), 1.26 (m, 35H), 1.93 (m, 1H), 2.50 (m, 1H), 2.63 (s, 3H), 3.15 (m, 2H), 3.52 (t, J=6.6Hz, 1H), 4.00 (m, 6H), 5.11 (s, 2H), 7.16 (m, 2H), 7.64 (t of d, J$_a$=7.4Hz, J$_b$=1.9Hz, 1H), 8.49 (d, J=4.0Hz, 1H).

Analysis calculated for $C_{33}H_{55}N_3O_6$: C 67.2%; H 9.3%; N 7.1%. Found C 67.24%; H 9.41%; N 7.08%.

EXAMPLE 53

(±)-cis,
trans-N-ethyl-2-[N-acetyl-[[[(4-heptadecylaminocarbonyloxymethyltetrahydrofuran-2-yl)methoxy]carbonyl]amino]methyl]pyridinium iodide Following the procedure described in example 10, and using instead of the compound prepared in example 9, the compound prepared in example 52, the title compound of this example was obtained as a white solid (86% yield).

mp: 48.2°–59.2° C.; IR (KBr) ν: 3410, 3329, 2913, 2846, 1687, 1463, 1212, 1161, 1085, 985 cm$^{-1}$; $^1$H-NMR (90 MHz, CDCl$_3$) δ: 0.87 (m, 3H), 1.25 (m, 35H), 1.73 (t, J=7.2Hz, 3H), 2.66 (s, 3H), 3.13 (q, J=6.2Hz, 2H), 3.80 (m, 4H), 4.25 (m, 3H), 4.9 (m, 1H), 5.06 (q, J=7.2Hz, 2H), 5.43 (s, 2H), 7.76 (d, J=8.0Hz, 1H), 8.04 (t, J=6.1Hz, 1H), 8.44 (t, J=8.1Hz, 1H), 9.63 (m, 1H).

Analysis calculated for $C_{35}H_{60}IN_3O_6.H_2O$: C 55.0%; H 8.1%; N 5.5%. Found: C 54.73%; H 7.95%; N 5.37%.

EXAMPLE 54

(±)-cis,
trans-2-[N-acetyl-[[[(4-heptadecylaminocarbonyloxymethyltetrahydrofuran-2-yl)methoxy]carbonyl]amino]methyl]pyridine N-oxide Following the procedure described in example 16, and using instead of the compound prepared in example 11, the compound prepared in example 52, a white solid was obtained (73% yield).

Rf=0.08 (silica gel, ethyl acetate); mp: 40.9°–50.5° C.; IR (KBr) ν: 3357, 2916, 2846, 1740, 1686, 1519, 1464, 1431, 1336, 1211 cm$^{-1}$.

Analysis calculated for $C_{33}H_{55}N_3O_7$: C 65.4%; H 9.0%; N 6.9%. Found: C 65.03%; H 9.31%; N 6.51%.

EXAMPLE 55

(±)-cis,
trans-3-[2-[N-methyl-[[(4-heptadecylaminocarbonyloxymethyltetrahydrofuran-2-yl)methoxy]carbonyl]amino]ethyl]thiazolium 4-methylbenzenesulfonate (a) (±)-cis,
trans-2-[N-methyl-[[(4-heptadecylaminocarbonyloxymethyltetrahydrofuran-2-yl)methoxy]carbonyl]amino]ethan-1-ol Following the procedure described in example 9, and using instead of the compound prepared in example 4b, (±)-cis, trans-(4-heptadecylaminocarbonyloxymethyltetrahydrofuran-2-yl)methanol prepared in example 8, and instead of 2-aminomethylpyridine, 2-(methylamino)ethanol, the desired product was obtained as a colorless oil (95% yield).

IR (film) ν: 3351, 2915, 2844, 1680, 1524, 1479, 1464, 1243 cm$^{-1}$. $^1$H-NMR (90MHz, CDCl$_3$) δ: 0.87 (m, 3H), 1.26 (m, 33H), 2.60 (m, 1H), 2.98 (s, 3H), 3.15 (q, J=4.9Hz, 2H), 3.35–4.15 (complex signal, 11H), 5.2 (m, 1H).

(b) (±)-cis,
trans-2-[N-methyl-[[(4-heptadecylaminocarbonyloxymethyltetrahydrofuran-2-yl)methoxy]carbonyl]amino]ethan-1-yl 4-methylbenzenesulfonate Following the procedure described in example 1e, and using instead of the compound prepared in example 1d, the compound prepared in example 55a, a white solid was obtained (57% yield).

Rf=0.19 (silica gel, hexane: ethyl acetate 1:1); IR (KBr) v: 3345, 2918, 2848, 1702, 1524, 1464, 1360, 1188, 1175 cm$^{-1}$; $^1$H-NMR (90MHz, CDCl$_3$) δ: 0.88 (m, 3H), 1.26 (m, 35H), 2.43 (m, 3H), 2.89 (m, 3H), 3.10 (m, 2H), 3.45–4.16 (complex signal, 11H), 5.2 (m, 1H), 7.36 (d, J=8.3Hz, 2H), 7.77 (d, J=8.3Hz, 2H).

(c) Preparation of the title Compound of this Example

Following the procedure described in example 1f, and using instead of the compound prepared in example 1 g, the compound prepared in example 55b, a white solid was obtained (65% yield).

mp: 40.8°–66.8° C.; IR (KBr) v: 3448, 3063, 2913, 1692, 1463, 1191 cm$^{-1}$; $^1$H-NMR (90 MHz, CDCl$_3$) δ: 0.88 (m, 3H), 1.26 (m, 34H), 2.35 (s, 3H), 2.57 (m, 2H), 2.88 (s, 3H), 3.12 (m, 2H), 3.94 (m, 9H), 5.0 (m, 3H), 7.16 (d, J=8Hz, 2H), 7.75 (d, J=8Hz, 2H), 8.12 (m, 1H), 8.45 (m, 1H), 10.68 (m, 1H).

EXAMPLE 56

(±)-cis, trans-2-[N-chloroacetyl-[[[(4-hexadecyloxymethyltetrahydrofuran-2-yl)methoxy]carbonyl]amino]methyl]-pyridine Following the procedure described in example 24, and using instead of the compound prepared in example 23, the compound prepared in example 9, and instead of acetyl chloride, chloroacetyl chloride, the title compound of this example was obtained as a white solid (85% yield).

Rf=0.38 and 0.32 (cis and trans isomers, silica gel, hexane:ethyl acetate 1:1); mp: 40.2°–42.2° C.; IR (KBr) v: 2921, 2850, 1737, 1590, 1463, 1392, 1352, 1199, 1113, 1032 cm$^{-1}$; $^1$H-NMR (90 MHz, CDCl$_3$) δ: 0.87 (m, 3H), 1.24 (m, 33H), 2.5 (m, 1H), 3.2–4,3 (complex signal, 9H), 4.85 (s, 2H), 5.11 (s, 2H), 7.19 (m, 2H), 7.60 (t of d, J$_a$=7.9Hz, J$_b$=1.8Hz, 1H), 8.45 (m, 1H).

Analysis calculated for C$_{31}$H$_2$O$_5$H$_{51}$Cl: C 65.7%; H 9.0%; N 4.9%. Found: C 65.56%; H 9.30%; N 4.70%.

EXAMPLE 57

(±)-cis, trans-2-[N-bromoacetyl-[[[(4-hexadecyloxymethyltetrahydrofuran-2-yl)methoxy]carbonyl]amino]methyl]-pyridine Following the procedure described in example 24, and using instead of the compound prepared in example 23, the compound prepared in example 9, and instead of acetyl chloride, bromoacetyl chloride, the title compound of this example was obtained as a white solid (57% yield).

Rf=0.33 and 0.40 (cis and trans isomers, silica gel, hexane:ethyl acetate 1:1); mp: 51.4°–57.3° C.; IR (KBr) v: 2920, 2850, 1736, 1591, 1392, 1352, 1198 cm$^{-1}$; $^1$H-NMR (90 MHz, CDCl$_3$) δ: 0.88 (m, 3H), 1.26 (m, 33H), 2.45 (m, 1H), 3.2–4.3 (complex signal, 9H), 4.85 (s, 2H), 5.14 (s, 2H), 7.20 (m, 2H), 7.65 (t of d, J$_a$=7.9 Hz, J$_b$=1.8 Hz, 1H), 8.52 (dd, J$_a$=4.0Hz, J$_b$=1.8Hz, 1H).

Analysis calculated for C$_{31}$N$_2$O$_5$H$_{51}$Br: C 60.9%; H 8.4%; N 4.6%. Found: C 60.85%; H 8.68%; N 4.44%.

EXAMPLE 58

(±)-cis, trans-N-ethyl-2-[N-acetyl-[[[(4-hexadecyloxymethyltetrahydrofuran-2-yl)methoxy]carbonyl]amino]methyl]-pyridinium chloride The compound prepared in example 13 was treated with a IRA-410 ion exchange resin (Cl$^-$form) (eluent- :methanol/water 7:3) and the resulting chloride was recrystallized from acetone (47% yield).

mp: 55.9°–79.9° C.; IR (KBr) v:3427, 3206, 2914, 2846, 1737, 1677, 1626, 1464, 1368, 1213 cm$^{-1}$; $^1$H-NMR (90 MHz, CDCl$_3$) δ: 0.88 (m, 3H), 1.26 (m, 33H), 1.73 (t, J=7.3Hz, 3H), 2.66 (s, 3H), 3.2–4.3 (complex signal, 9H), 5.22 (q, J=7.3Hz, 2H), 5.39 (s, 2H), 7.65 (d, J=7.0Hz, 1H), 8.04 (t, J=4.9Hz, 1H), 8.31 (t, J=6.6Hz, 1H), 10.31 (d, J=5.7Hz, 1H).

EXAMPLE 59

(±)-cis, trans-N-ethyl-2-[N-acetyl-[[[(4-heptadecylaminocarbonyloxymethyltetrahydrofuran-2-yl)methoxy]carbonyl]amino]methyl]pyridinium chloride The compound prepared in example 53 was treated with IRA-410 ion exchange resin (Cl$^-$form) (eluent- :methanol:water 7:3) and the resulting chloride was recrystallized from acetone (85% yield).

mp: 48.6°–62.3° C.; IR (KBr) v:3418, 2912, 2846, 1740, 1687, 1625, 1530, 1463, 1448, 1367, 1224, 1161 cm$^{-1}$; $^1$H-NMR (90MHz, CDCl$_3$) δ: 0.88 (m, 3H), 1.24 (m, 35H), 1.72 (t, J=7.3Hz, 3H), 2.5 (m, 1H), 2.65 (s, 3H), 3.14 (m, 2H), 3.4–4.4 (complex signal, 9H), 5.20 (q, J=7.3Hz, 2H), 5.41 (s, 2H), 7.63 (d, J=6.9Hz, 1H), 8.02 (t, J=5,0Hz, 1H), 8.30 (t, J=6.5Hz, 1H), 10.24 (d, J=5,0Hz, 1H).

Analysis calculated for C$_{35}$H$_{60}$N$_3$O$_6$CL.H$_2$O:C 62.5%; H 9.2%; N 6.2%. Found: C 62.37%; H 9.49%; N 6.13%.

EXAMPLE 60

(±)-cis, trans-N-propyl-2-[N-acetyl-[[[(4-hexadecyloxynethyltetrahydrofuran-2-yl)methoxy]carbonyl]amino]methyl]pyridinium chloride Following the procedure described in example 58, and using instead of ethyl iodide, propyl iodide the title compound of this example was obtained in a similar yield.

EXAMPLE 61

(±)-cis, trans-3-[7-[(2-octadecyloxymethyltetrahydrofuran-4-yl)methoxy]heptyl]thiazolium chloride (a) 2-Trityloxymethylpent-5-1-ol To a solution of 2-allyl-1,3-propandiol (8 g, 69 mmol) in dichloromethane (60 mL) and anhydrous pyridine (10 mL), trityl chloride (19.7 g, 70 mmol) was added and the mixture was stirred at room temperature for 18 h. The mixture was diluted with dichloromethane (300 mL) and washed with 1N HCl solution (×4). The organic phase was dried over anhydrous sodium sulfate and after evaporating the solvent, 29 g of a crude were obtained that was purified by column chromatography (silica gel, hexane:ethyl acetate 10%), to afford 12.6 g of a white solid (51% yield).

IR (KBr) ν: 3421, 3055, 3027, 2919, 2871, 1635, 1593, 1486, 1445, 1219, 1151, 1087, 1067, 1033 cm$^{-1}$; $^1$H-NMR (60 MHz, CDCl$_3$) δ: 2.1 (m, 4H), 3.25 (m, 2H), 3.7 (m, 2H), 5.0 (m, 1H), 5.7 (m, 1H), 7.4 (m, 15H).

(b) (±)-cis,
trans-(4-trityloxymethyltetrahydrofuran-2-yl)methanol

To a solution of the compound prepared in example 61a (12.6 g, 35 mmol) in dichloromethane (100 mL), m-chloroperbenzoic acid (53 mmol) was added, dissolved in dichloromethane (50 mL) and the mixture was stirred at room temperature for 2 days. The mixture was diluted with dichloromethane (100 mL) and was washed with a 10% sodium thiosulfate solution and a 1N sodium hydroxide solution (×2). The organic phase was dried over anhydrous sodium sulfate and after evaporating the solvent 14.8 g of a white solid was obtained (quantitative yield).

Rf=0.29 (silica gel, hexane:ethyl acetate 1:1), IR (KBr) ν: 3419, 3081, 3053, 3027, 2924, 2863, 1486, 1445, 1215, 1070, 1032 cm$^{-1}$; $^1$H-NMR (90 MHz, CDCl$_3$) δ: 1.65 (m, 2H), 2.55 (q, J=7.3Hz, 1H), 3.13 (m, 3H), 3.48 (m, 2H), 3.91 (m, 2H), 7.28 (m, 15H); $^{13}$C-NMR (20.15 MHz, CDCl$_3$) δ: 30.74, 31.15, 39.94, 40.38, 64.76, 64.92, 65.21, 65.56, 71.22, 71.47, 79.37, 80.35, 86.67, 127.18, 127.97, 128.84, 144.30.

(c) (±)-cis,
trans-4-trityloxymethyl-2-octadecyloxymethyltetrahydrofuran

To a solution od sodium hydride (2.1 g 47.8 mmol) in anhydrous dimethylformamide (40 mL) under argon atmosphere, it was added dropwise a mixture of the compound prepared in example 61b (12 g, 32 mmol) and bromooctadecane (15.9 g, 47.8 mmol) dissolved in anhydrous dimethylformamide (40 mL) and the mixture was heated at 60° C. for 6 h. The reaction mixture was cooled, poured over a 1M pH 7 phosphate buffer and extracted with hexane. The organic solution was dried over sodium sulfate and after evaporating the solvent 25 g of a crude was obtained that was purified by column chromatography (silica gel, hexane:ethyl acetate 4%), to yield 10.48 g of a white solid (52% yield).

IR (KBr) ν: 3082, 3054, 3027, 2921, 2850, 1593, 1486, 1463, 1446, 1117, 1071, 1032 cm$^{-1}$.

(d) (±)-cis,
trans-(2-octadecyloxymethyltetrahydrofuran-4-yl)methanol

To the compound prepared in example 61c (10.4 g, 16.6 mmol) dissolved in methanol (120 mL) and tetrahydrofuran (30 mL) p-toluenesulfonic acid (1.68 g) was added and the mixture was stirred at room temperature under argon atmosphere for 15 h. Afterwards, the solvent was evaporated, the residue was dissolved in diethyl ether and washed with a saturated solution of sodium bicarbonate. The organic phase was separated and dried over anhydrous sodium sulfate and after evaporating the solvent 11.8 g of a crude were obtained that was purified by column chromatography (silica gel, hexane:ethyl acetate 25%) to afford 5.48 g of a waxy solid (86% yield).

IR (KBr) ν: 3410, 2918, 2850, 1464, 1214, 1101 cm$^{-1}$; $^1$H-NMR (60 MHz, CDCl$_3$) δ: 0.6–2.0 (complex signal, 33H), 2.55 (m, 3H), 3.2–4.3 (complex signal, 9H).

(e) (±)-cis,
trans-7-[(2-octadecyloxymethyltetrahydrofuran-4-yl)methoxy]heptyl tetrahydropiranyl ether Following the procedure described in example 1c, and using instead of the compound prepared in example 1b, the compound prepared in example 61d, the desired product was obtained as a colorless oil (63% yield).

Rf=0.67 (silica gel, hexane:ethyl acetate 1:1); IR (film) ν: 3223, 2851, 1462, 1362, 1350, 1120, 1078, 1033 cm$^{-1}$; $^1$H-NMR (60 MHz, CDCl$_3$) δ: 0.7–2.0 (complex signal, 51H), 3.1–4.3 (complex signal, 15H), 4.5 (m, 1H).

(f) (±)-cis,
trans-7-[(2-octadecyloxymethyltetrahydrofuran-4-yl)methoxy]heptanol Following the procedure described in example 1d, and using instead of the compound prepared in example 1c, the compound prepared in example 61f, a colorless oil was obtained (95% yield).

Rf=0.44–0.39 (cis and trans isomers, silica gel, hexane:ethyl acetate 1:1); $^1$H-NMR (60 MHz, CDCl$_3$) δ: 0.6–2.0 (complex signal, 48H), 2.9–4.3 (complex signal, 13H).

(g) (±)-cis,
trans-7-[(2-octadecyloxymethyltetrahydrofuran-4-yl)methoxy]heptyl 4-methylbenzenesulfonate Following the procedure described in example 1e, and using instead of the compound prepared in example 1d, the compound prepared in example 61f, a white solid was obtained (40% yield).

Rf=0.19 and 0.17 cis and trans isomers (silica gel, hexane:ethyl acetate 20%).

High Rf isomer (0.23 g): mp: 35.5°–35.8° C.; $^1$H-NMR (60 MHz, CDCl$_3$) δ: 0.6–1.9 (complex signal, 48H) 2.4 (s, 3H), 3.4 (m, 9H), 4.0 (m, 4H), 7.4 (d, J=7.6 Hz, 2H), 7.8 (d, J=7.6Hz, 2H).

Mixture of isomers (0.60 g): IR (KBr) ν: 2914, 2847, 1596, 1466, 1359, 1187, 1172, 1107, 957 cm$^{-1}$; $^1$H-NMR (60 MHz, CDCl$_3$) δ: 0.6–2.0 (complex signal, 48H), 2.4 (s, 3H), 3.1–4.2 (complex signal, 9H), 7.35 (d, J=7.6Hz, 2H), 7.8 (d, J=7.6Hz, 2H).

(h) Preparation of the Title Compound of this Example

Following the procedure described in example 1f, and using instead of the compound prepared in example 1e, the compound prepared in example 61g, the title compound of this example was obtained as a white solid (74% yield).

mp: 74.8°–80.9° C.; IR (KBr) ν: 2915, 2846, 1559, 1464, 1213, 1193, 1120, 1034, 1010, 817 cm$^{-1}$.

Analysis calculated for C$_{41}$H$_{71}$NO$_6$S$_2$: C 66.7%; H 9.7%; N 1.9%. Found : C 66.79%; H 10.23%; N 1.85%.

EXAMPLE 62

(±)-cis,
trans-3-[5-[(2-octadecyloxymethyltetrahydrofuran-4-yl)methoxy]pentyl]thiazolium
4-methylbenzenesulfonate (a) (±)-cis,
trans-5-[(2-octadecyloxymethyltetrahydrofuran-4-yl)methoxy]pentyl, tetrahydropiranyl ether Following the procedure described in example 1c, and using instead of the compound prepared in example 1b, the compound prepared in example 61d, and instead of 7-(tetrahydropiranyl-2-oxy)heptyl 4-methylbenzenesulfonate, 5-(tetrahydropiranyl-2-oxy)pentyl 4-methylbenzenesulfonate, a colorless oil was obtained (32% yield).

Rf=0.66 (silica gel, hexane:ethyl acetate 1:1); IR (film) v: 2920, 2850, 1463, 1350, 1321, 1120, 1078, 1034 cm$^{-1}$.

(b) (±)-cis,
trans-5-[(2-octadecyloxymethyltetrahydrofuran-4-yl)methoxy]pentanol Following the procedure described in example 1d, and using instead of the compound prepared in example 1c, the compound prepared in example 62a, a colorless oil was obtained (95% yield).

Rf=0.35 and 0.40 (cis and trans isomers, silica gel, hexane:ethyl acetate 1:1); IR (film) v: 3389, 2914, 2847, 2321, 1463, 1373, 1117, 721 cm$^{-1}$.

(c) (±)-cis,
trans-5-[(2-octadecyloxymethyltetrahydrofuran-4-yl)methoxy]pentyl 4-methylbenzenesulfonate Following the procedure described in example 1e and using instead of the compound prepared in example 1d, the compound prepared in example 62b, a white solid was obtained (58% yield).

Rf=0.09 (silica gel, hexane:ethyl acetate 20%); IR (KBr) v: 2916, 2848, 1595, 1464, 1356, 1187, 1175, 1097, 959, 912, 815 cm$^{-1}$.

(d) Preparation of the Title Compound of this Example

Following the procedure described in example 1f, and using instead of the compound prepared in example 1e, the compound prepared in example 62c, the title compound of this example was obtained as a white solid (84% yield).

mp: 81.4°-87.9° C.; IR (KBr) v: 3126, 2914, 2847, 1464, 1210, 1192, 1121 cm$^{-1}$.

Analysis calculated for $C_{39}H_{67}No_6S_2 \cdot \frac{1}{2}H_2O$: 65.1%; H 9.5%. Found: C64.74%; H 9.83%; N 1.87%.

EXAMPLE 63

(3S)-cis,
trans-3-[6-[(2-hexadecyloxymethyltetrahydrofuran-4-yl)methoxy]hexyl]thiazolium 4-methylbenzenesulfonate (a) (±)-cis,
trans-6-[(2-hexadecyloxymethyltetrahydrofuran-4-yl)methoxy]hexyl tetrahydropiranyl ether Following the procedure described in example 1c, and using instead of the compound prepared in example 1b, (±)-cis, trans-(2-hexadecyloxymethyltetrahydrofuran-4-yl)methanol (prepared in a similar way to the compound described in example 61d), and instead of 7-(tetrahydropiranyl-2-oxy)heptyl 4-methylbenzenesulfonate, 6-(tetrahydropiranyl-2-oxy)hexyl 4-methylbenzenesulfonate, a colorless oil was obtained (51% yield).

Rf=0.08 (silica gel, hexane:ethyl acetate 10%); IR (film) v: 2921, 2850, 1462, 1351, 1119, 1078, 1033 cm$^{-1}$; H-NMR (60 MHz, CDCl$_3$) δ: 0.7-2.0 (complex signal, 48H), 3.3-4.2 (complex signal, 15H), 4.7 (m, 1H).

(b) (±)-cis,
trans-6-[(2-hexadecyloxymethyltetrahydrofuran-4-yl)mehtoxyl]hexanol.

Following the procedure described in example 1d, and using instead of the compound prepared in example 1c, the compound prepared in example 63a, a colorless oil was obtained (96% yield).

Rf=0.33 (silica gel, hexane:ethyl acetate 1:1); IR (film) v 3443, 2920, 2850, 2326, 1462, 1375, 1116 cm$^{-1}$.

(c) (±)-cis,
trans-6-[(2-hexadecyloxymethyltetrahydrofuran-4-yl)methoxy]hexyl 4-methylbenzenesulfonate Following the procedure described in example 1e, and using instead of the compound prepared in example 1d, the compound prepared in example 63b, a white solid was obtained (49% yield).

Rf=0.42 (silica gel, hexane:ethyl acetate 1:1); IR (KBr) v: 2921, 2851, 1595, 1361, 1188, 1176, 1115 cm$^{-1}$; $^1$H-NMR (60 MHz, CDCl$_3$) δ: 0.7-2.0 (complex signal, 42H), 2.45 (m, 3H), 3.4 (m, 7H), 3.9 (m, 6H), 7.35 (d, J=7.4Hz, 2H), 7.8 (d, J=7.4Hz, 2H).

(d) Preparation of the Title Compound of this Example

Following the procedure described in example 1f, and using instead of the compound prepared in example 1e, the compound prepared in example 63c, the title compound of this example was obtained as a white solid (84% yield).

mp: 71.8°-82.6° C.; IR (KBr) v: 3140, 2914, 2847, 1556, 1464, 1377, 1212, 1193, 1120, 1034, 1010 cm$^{-1}$.

Analysis calculated for $C_{38}H_{65}NO_6S_2$: C 65.7%; H 10.3%; N2.01%. Found: C 65.46%; H 9.71%; N 2.00%.

EXAMPLE 64

(±)-cis,
trans-3-[6-[(2-octadecyloxymethyltetrahydrofuran-4-yl)methoxy]6-oxohexyl]thiazolium 4-methylbenzenesulfonate (a) (±)-cis,
trans-6-[(2-octadecyloxymethyltetrahydrofuran-4-yl)methoxy]6-oxohexyl 4-methylbenzenesulfonate Following the procedure described in example 5a, and using instead of the compound prepared in example 4b, the compound prepared in example 61d, a white solid was obtained (63% yield).

Rf=0.65 (silica gel, hexane:ethyl acetate 1:1); IR (KBr) v: 2921, 2849, 1732, 1595, 1463, 1359, 1187, 1176, 1097, 954 cm$^{-1}$. $^1$H-NMR (60 MHz, CDCl$_3$) δ: 0.7-2.0 (complex signal, 44H), 2.05 (t, J=6Hz, 2H), 2.3 (s, 3H), 3.35 (m, 4H), 3.8 (m, 7H), 7.3 (d, J=8Hz, 2H), 7.75 (d, J=8Hz, 2H).

(b) Preparation of the Title Compound of this Example

Following the procedure described in example 1f, and using instead of the compound prepared in example 1e, the compound prepared in example 64a, the title compound of this example was obtained as a white solid (65% yield).

mp: 76.2°-87.8° C.; IR (KBr) v: 3443, 3059, 2915, 2846, 1731, 1551, 1464, 1423, 1379, 1224, 1188, 1119 cm$^{-1}$.; $^1$H-NMR (200 MHz, CDCl$_3$) δ: 0.88 (t, J=6.2Hz, 3H), 1.24 (m, 41H), 1.57 (m, 2H), 1.91 (m, 1H), 2.23 (t, J=7.2Hz, 2H), 2.34 (s, 3H), 2.57 (m, 1H), 3.44 (m, 4H), 3.67 (half ABC system, $J_{AB}$=8.9Hz, $J_{AC}$=5.5Hz, 1H), 3.84 (half ABC system, $J_{AB}$=8.9Hz, $J_{BC}$=6.9Hz, 1H), 4.20 (m, 3H), 4.66 (t, J=7.4Hz, 2H), 7.16 (d, J=7.9Hz, 2H), 7.76 (d, J=7.9Hz, 2H), 8.25 (d of d, $J_a$=3.6Hz, $J_b$=2.4Hz, 1H), 8.36 (d of d, $J_a$=3.7Hz, $J_b$=1.3Hz, 1H), 10.85 (s, 1H).

EXAMPLE 65

(±)-cis,
trans-2-[[[[(2-octadecyloxymethyltetrahydrofuran-4-yl)methoxy]carbonyl]amino]methyl]pyridine Following the procedure described in example 9, and using instead of the compound prepared in example 4b, the compound prepared in example 61b, a white-yellowish solid was obtained (77% yield).

Rf=0.14 (silica gel, hexane:ethyl acetate 1:1); $^1$H-NMR (60 MHz, CDCl$_3$) δ: 0.7–2.0 (complex signal, 37H), 2.55 (m, 1H), 3.3–4.3 (complex signal, 9H), 4.45 (d, J=5.4Hz, 2H), 6.45 (m, 1H), 7.2 (m, 2H), 7.65 (t, J=7.5Hz, 1H), 8.5 (d, J=4Hz, 1H).

EXAMPLE 66

(±)-cis,
trans-N-methyl-2-[[[[(2-octadecyloxymethyl-tetrahydrofuran-4-yl)methoxy]carbonyl]amino]methyl]pyridinium iodide Following the procedure described in example 12, and using instead of the compound prepared in example 11, the compound prepared in example 65, the title compound of the example was obtained as a yellow solid (84% yield).

mp: 61.8°–64.7° C.; IR (KBr) v: 3438, 3233, 3039, 2913, 2846, 1711, 1625, 1524, 1463, 1248 cm$^{-1}$; $^1$H-NMR (90 MHz, CDCl$_3$) δ: 0.89 (m, 3H), 1.27 (m, 32H), 1.62 (s, 3H), 2.65 (m, 1H), 3.46 (m, 4H), 4.05 (m, 5H), 4.59 (s, 3H), 4.96 (d, J=5.9 Hz, 2H), 6.75 (m, 1H, NH), 7.9 (t, J=6.7 H), 8.35 (m, 2H), 9.1 (d, J=4.0 Hz, 1H).

Analysis calculated for C$_{32}$H$_{57}$IN$_2$O$_4$.3H$_2$O: C 53.8%; H 8.0%; N 4.0%. Found: C 53.90%; H 8.31%; N 4.54%.

EXAMPLE 67

(±)-cis,
trans-2-[N-acetyl-[[[(2-octadecyloxycarbonyltetrahydrofuran-4-yl)methoxy]carbonyl]amino]methyl]pyridine Following the procedure described in example 11, and using instead of the compound prepared in example 9, the compound prepared in example 65, the title compound of this example was obtained as a yellow oil (52% yield).

Rf=0.31 and 0.27 (cis and trans isomers, silica gel, hexane: ethyl acetate 1:1); IR (film) v: 2915, 2848, 1737, 1698, 1589, 1463, 1430, 1392, 1368, 1343, 1285, 1206, 1188, 1098, 1078, 1047 cm$^{-1}$; $^1$H-NMR (60 MHz, CDCl$_3$: 0.7–1.8 (complex signal, 38H), 2.55 (s, 3H), 3.3 (m, 5H), 4.0 (m, 4H), 5.05 (s, 2H), 7.05 (m, 2H), 7.6 (t, J=7.5 Hz, 1H), 8.04 (d, J=5 Hz, 1H).

EXAMPLE 68

(±)-cis,
trans-N-methyl-2-[N-acetyl-[[[(2-octadecyloxymethyl-tetrahydrofuran-4-yl)methoxy]carbonyl]amino]methyl]pyridinium iodide Following the procedure described in example 12, and using instead of the compound prepared in example 11, the compound prepared in example 67, the title compound of this example was obtained as a white-yellowish solid (86% yield).

mp: 49.0°–69.7° C.; IR (KBr) v: 3443, 2914, 2845, 1746, 1681, 1626, 1579, 1510, 1463, 1427, 1367, 1338, 1278, 1212, 1188, 1117, 1083 cm$^{-1}$; $^1$H-NMR (200 MHz, CDCl$_3$) δ: 0.88 (t, J=7.2Hz, 3H), 1.25 (m, 35H), 1.57 (m, 2H), 1.83 (m, 1H), 2.10 (m, 1H), 2.63 (s, 3H), 2.67 (m, 1H), 3.5 (m, 4H), 3.85 (m, 1H), 4.10 (m, 1H), 4.33 (m, 3H), 4.68 (s, 0.66×3H), 4.69 (s, 0.33×3H), 5.40 (s, 0.33×3H), 5.42 (s, 0.66×3H), 7.85 (m, 1H), 8.06 (m, 1H), 8.53 (t, J=7.6Hz, 1H), 9.46 (m, 1H).

Analysis calculated for C$_{34}$H$_{59}$IN$_2$O$_5$.1½H$_2$O: C 55.9%; H 8.1%; N 3.9%. Found: C 55.72%; H 8.07%; N 4.42%.

EXAMPLE 69

(±)-cis,
trans-N-ethyl-2-[N-acetyl-[[[(2-octadecyloxymethyltetrahydrofuran-4-yl)methoxy]carbonyl]amino]methyl]pyridinium iodide Following the procedure described in example 68, and using instead of methyl iodide, ethyl iodide, the title compound of this example was obtained with a similar yield.

EXAMPLE 70

(±)-cis,
trans-3-[6-[(4-tetradecyltetrahydrofuran-2-yl)methoxy]hexyl]thiazolium 4-methylbenzenesulphonate

(a) ethyl 2-allylhexadecanoate

To a solution of n-butyl lithium (hexane, 0.048 mol) in 120 mL of anhydrous tetrahydrofuran at 0° C. and under argon atmosphere, diisopropylamine was added (6.8 mL, 0.048 mol). Afterwards, ethyl hexadecanoate (11.3 g, 0.04 mol) in tetrahydrofuran (15 mL) was added dropwise and the homogeneous solution was stirred for 1 h at the same temperature. Next, allyl bromide (4.0 mL, 0.048 mol) was added and the resulting mixture was stirred at room temperature for 12 h. The mixture was poured on water, extracted with ethyl acetate, dried over anhydrous sodium sulfate and the solvent evaporated to afford 11.9 g of an oil. The product was chromatographed (silica gel, hexane: ethyl acetate, 3%) to afford 8.7 g of a colorless oil (67% yield).

IR (film) v: 3075, 2921, 2851, 1731, 1638, 1462, 1176, cm$^{-1}$; $^1$H-NMR (60 MHz, CDCl$_3$) δ: 0.7–2 (complex signal, approx. 29H), 2.4 (m, 4H), 4.2 (q, J=7Hz, 2H), 5.1 (m, 2H), 5.8 (m, 1H).

(b) 2-allylhexadecan-1-ol

To a suspension of lithium aluminium hydride (2.0 g, 0.052 mol) in anhydrous tetrahydrofuran (150 mL) at 0° C. it was added a solution of the product prepared in example 70a (8.7 g, 0.026 mol) in tetrahydrofuran (20 mL) and the resulting mixture was stirred at room temperature for 2 h. Afterwards, 120 mL of methylene chloride were added followed by 8.4 mL of a saturated solution of sodium and potassium tartrate and sodium sulfate. The inorganic salts were separated by filtration and the solvent was evaporated to afford 7.4 g of an oil. The product was purified by column chromatography (silica gel, hexane: ethyl acetate 10%) to afford 6.2 g of a colorless oil (82% yield).

IR (film) v: 3339, 3072, 2921, 2850, 1636, 1463, 1375, 1043, 910 cm$^{-1}$; $^1$H-NMR (60 MHz, CDCl$_3$) δ: 0.7–1.7 (complex signal, approx. 29H), 2.1 (m, 4H), 3.5 (d, J=5Hz, 2H, CH$_2$OH), 5.0 (m, 2H), 5.7 (m, 1H).

(c) (±)-cis, trans-(4-tetradecyltetrahydrofuran-2-yl)methanol

The compound prepared in example 70b (6.2 g, 22.2 mmol) was dissolved in methylene chloride (150 mL)

and 85% m-chloroperbenzoic acid (7 g, 34.7 mmol) was added and the mixture was stirred for 16 h. Afterwards, t was diluted with methylene chloride (100 mL) and washed with 20% sodium thiosulfate followed by 2% sodium hydroxide. The organic phase was dried with anhydrous sodium sulfate, the solvent was evaporated and the resulting oil (6.4 g) was purified by chromatography (silica gel, hexane: ethyl acetate 30%), to afford 4.7 g of a (1:1) mixture of the cis and trans isomers as a white solid (71% yield).

mp: 27.1°-27.7° C.; IR (film) ν: 3422, 2919, 2850, 1463, 1375, 1049 cm$^{-1}$; $^1$H-NMR (60 MHz, CDCl$_3$) δ: 0.6-2.2 (complex signal, approx. 32H), 3.0 (m, 1H, OH), 3.5 (m, 3H), 3.95 (m, 2H); $^{13}$C-NMR (50.3 MHz, CDCl$_3$) δ: 14.11 (CH$_3$), 22.69 (CH$_2$), 28.48 (CH$_2$), 28.59 (CH$_2$), 29.37 (CH$_2$), 29.59 (CH$_2$), 29.68 (CH$_2$), 29.76 (CH$_2$), 31.94 (CH$_2$), 33.11 (CH$_2$), 33.19 (CH$_2$), 33.85 (CH$_2$), 34.27 (CH$_2$), 39.48 (CH), 40.17 (CH), 64.97 (CH$_2$), 65.32 (CH$_2$), 73.44 (CH$_2$), 73.88 (CH$_2$), 79.00 (CH), 80.12 (CH).

Analysis calculated for C$_{19}$H$_{36}$O$_2$: C 76.5%; H 12.8%. Found: C 76.19%; H 12.73%.

(d) (±)-cis,
trans-6-[(4-tetradecyltetrahydrofuran-2-yl)methoxy]-hexyl, tetrahydropiran-2-yl ether To a suspension of sodium hydride (0.5 g, 11.4 mmol) in anhydrous dimethylformamide (20 mL) under argon atmosphere it was added the compound prepared in example 70 c (2.58 g, 8.8 mmol) dissolved in 5 mL of anhydrous dimethylformamide and the resulting mixture was heated at 100° C. for 1 h. Afterwards, 6-(tetrahydropiranyl-2-oxy)hexyl 4-methylbenzene sulfonate (3.5 g, 9.8 mmol) was added and after heating the mixture at 100° C. for 4 h 0.25 g of sodium hydride was added, followed by 1.7 g (4.7 mmol) of 6-(tetrahydropiranil-2-oxy)hexyl 4-methylbenzenesulfonate and the resulting mixture was heated again at 100° C. for 3 h. After cooling at room temperature, the mixture was poured on 1M pH 7 phosphate buffer and was extracted with hexane. The organic phase was dried over anhydrous sodium sulfate and after evaporation of the solvent it was obtained 4.4 g of an oil that was purified by column chromatography (silica gel, hexane : ethyl acetate 10%) to afford 2.38 g of the desired product as a colorless oil (56% yield) and 0.63 g of the starting alcohol.

$^1$H-NMR (60 MHz, CDCl$_3$) δ: 0.6-2.3 (complex signal, approx. 51H), 3.2-4.3 (m, 11H), 4.55 (m, 1H, OCHO).

(e) (±)-cis,
trans-[(4-tetradecyltetrahydrofuran-2-yl)methoxy]hexan-1-ol

A mixture of the compound prepared in example 70d 2.38 g, 4.9 mmol), camphorsulfonic acid (20 mg) and 35 mL of methanol was stirred at room temperature for 16 h. Afterwards, the mixture was concentrated to dryness and the residue was treated with 1M pH7 phosphate buffer and extracted with ethyl acetate. The organic phase was dried over anhydrous sodium sulfate and after evaporating the solvent 1.69 g of a colorless oil was obtained (87.5% yield).

IR (film) ν: 3427, 2921, 2850, 1462, 1373, 1121 cm$^{-1}$; $^1$H-NMR (60 MHz, CDCl$_3$) δ: 0.7-1.9 (complex signal, approx. 40H), 3.2 (m, 7H), 4.0 (m, 3H).

(f) (±)-cis,
trans-6-[(4-tetradecyltetrahydrofuran-2-yl)methoxy]-hexyl] 4-methylbenzenesulfonate The compound obtained in example 70e (1.4 g, 3.5 mmol) was dissolved in 15 mL of methylene chloride containing 5 mL pf pyridine, cooled at 0° C. and over this solution it was added dropwise a solution of 4-methylbenzenesulfonyl chloride (1 g, 5 mmol) in 5 mL of methylene chloride. The resulting mixture was stirred at room temperature for 12 h. Then, the reaction mixture was treated with a 0.1M HCl solution, the organic phase was dried over anhydrous sodium sulfate and after evaporation of the solvent, it was obtained 2.5 g of a solid that was purified by column chromatography (silica gel, hexane : ethyl acetate 20%) to afford 1.5 g of a white solid (79% yield).

IR (KBr) ν: 2921, 2850, 1462, 1361, 1187, 1176, 1097 cm$^{-1}$; $^1$H-NMR (60 MHz, CDCl$_3$) δ: 0.7-2.4 (complex signal, approx. 40H), 2.5 (s, 3H), 3.5 (m, 5H), 4.1 (m, 4H), 7.4 (d, J=8 Hz, 2H), 7.9 (d, J=8 Hz, 2H).

(g) Preparation of the Title Compound of this Example

A mixture of 0.31 g of the compound obtained in example 70f and 0.7 mL of thiazole was heated at 100° C. for 4 h. After cooling to room temperature, the mixture was diluted with diethyl ether and the solid that precipitated was filtered, dried and recrystallized from methylene chloride: diethyl ether to afford 0.24 g of a white solid (67% yield).

mp: 74.4°-90.8° C.; IR (KBr) ν: 3466, 3134, 2915, 2847, 1464, 1212, 1192, 1121, 1034, 1010, 817, 683, 561 cm$^{-1}$; $^1$H-NMR (200 MHz, CDCl$_3$) δ: 0.87 (t, J=6.0Hz, 3H), 1.1-2.2 (complex signal, approx. 40H), 2.33 (s, 3H, Tos-CH$_3$), 2.9 (m, 1H, H$_2$O), 3.37 (m, 5H), 4.0 (m, 4H), 4.58 (t, 2H, J=6.0Hz, CH$_2$N), 7.15 (d, J=7.5Hz, 2H), 7.75 (d, J=7.5Hz, 2H), 8.30 (m, 1H, thiazole), 8.45 (m, 1H, thiazole), 10.70 (m, 1H, NCHS).

Analysis calculated for C$_{35}$H$_{59}$NO$_5$S$_2$.½H$_2$O: C 65.0%; H 9.3%; N 2.2%. Found: C 65.06%; H 9.63%; N 2.12%.

EXAMPLE 71

(±)-cis,
trans-6-[6-(4-tetradecyltetrahydrofuran-2-yl)methoxy)]N,N,N-trimethylhexaminium 4-methylbenzenesulfonate A mixture of 0.26 g of the compound obtained in example 70f and 10 mL of a solution prepared dissolving 100 g of trimethylamine in 200 mL of acetonitrile, was refluxed for 4 h. The mixture was cooled to room temperature and, by addition of diethyl ether, 0.20 g of a white solid were precipitated (69% yield).

mp: 175.8°-193.4° C.; IR (KBr) ν: 3031, 2916, 2846, 1488, 1464, 1194, 1120, 1034, 1010, 819, 683, 563 cm$^{-1}$; $^1$H-NMR (200 MHz, CDCl$_3$) δ: 0.88 (t, J=6Hz, 3H), 1.2-1.9 (complex signal, approx. 40H), 2.14 (m, 2H), 2.30 (s, 3H, Tos-CH$_3$), 3.2 (s, 9H, N(CH$_3$)$_3$), 3.1-3.3 (complex signal, 9H), 4.0 (m, 2H), 7.13 (d, J=8 Hz, 2H), 7.72 (d, J=8Hz, 2H).

Analysis calculated for C$_{35}$H$_{65}$NO$_5$S: C 68.7%; H 10.6%; N 2.3%. Found: C 68.50%; H 11.00%; N 2.16%.

EXAMPLE 72

(±)-cis,
trans-1-[6-[(4-tetradecyltetrahydrofuran-2-yl)methoxy]-hexyl]quinolinium 4-methylbenzenesulfonate Following the same procedure described in the example 70g, and using instead of thiazole an equivalent amount of quinoline, a pink solid was obtained (62.5% yield).

mp: 79.1°–82.6° C.; IR (KBr) ν: 2915, 2847, 1623, 1593, 1524, 1463, 1376, 1216, 1193, 1118, 1032, 1011, 816, 809, 775, 680, 560 cm$^{-1}$; $^1$H-NMR (60 MHz, CDCl$_3$) δ0.6–2.2 (complex signal, approx. 40H), 2.3 (s, 3H, Tos-CH$_3$), 3.45 (m, 5H), 4.0(m, 2H), 5.25 (m, 2H, CH$_2$CN), 7.15 (d, J=8Hz, 2H), 7.85 (d, J=8Hz, 2H), 8.1 (m, 5H), 9.1 (m, 1H), 10.2 (m, 1H).

Analysis calculated for C$_{41}$H$_{63}$NO$_5$S: C 72.2%; H 9.3%; N 2.0%. Found: C 72.03%; H 9.70; N 1.96%.

EXAMPLE 73

(±)-cis,
trans-3-methyl-1-[6-[(4-tetradecyltetrahydrofuran-2-yl)methoxy]hexyl]imidazolium 4-methylbenzenesulfonate Following the same procedure described in example 70 g, but using instead of thiazole an equivalent amount of 1-methylimidazole, a white solid was obtained (38% yield).

mp: 47.2°–63.5° C.; IR (KBr) ν: 3453, 3144, 3097, 2919, 2849, 1638, 1566, 1462, 1193, 1121, 1033, 1011, 816, 682, 566 cm$^{-1}$; $^1$H-NMR (60 MHz, CDCl$_3$) δ: 1.6–2.3 (complex signal, approx. 40H), 2.3 (s, 3H, Tos-CH$_3$), 3.4 (m, 5H), 4.0 (s, 3H, CH$_3$CN), 4.1 (m, 4H), 7.2 (d, J=8 Hz, 2H), 7.4 (m, 2H, imidazole), 7.8 (d, J=8 Hz, 2H), 9.8 (m, 1H, N=CHN).

Analysis calculated for C$_{36}$H$_{62}$N$_2$O$_5$S.2H$_2$O: C 64.4%; H 9.8%; N 4.2%. Found C 64.19%; H 9.59%; N 4.43%.

EXAMPLE 74

(±)-cis,
trans-1-[6-[(4-tetradecyltetrahydrofuran-2-yl)methoxy]-hexyl]pyridinium methanesulfonate (a) (±)-cis,
trans-6-[(4-tetradecyltetrahydrofuran-2-yl)methoxy]-hexyl 4-methanesulfonate Following the procedure described in example 70f, but using instead of 4-methylbenzenesulfonyl chloride, an equivalent amount of methanesulfonyl chloride, a colorless oil was obtained (61% yield).

IR (film) ν: 2920, 2850, 1463, 1355, 1175, 1110, 973, cm$^{-1}$; $^1$H-NMR (60 MHz, CDCl$_3$) δ: 0.6–2.0 (complex signal, approx. 40H), 3.0 (s, 3H, CH$_3$Ms), 3.5 (m, 5H), 4.1 (m, 4H).

(b) Preparation of the Title Compound of this Example

Following the procedure described in example 70g, but using instead of the compound prepared in example 70f, the compound obtained in example 74a and instead of thiazole, an equivalent amount of pyridine, a white solid was obtained (41% yield).

mp: 30.9°–36.2° C.; IR (KBr) ν: 3426, 2920, 2850, 1631, 1485, 1463, 1207, 1192, 1120, 1058, 785, 772, 685, 562, 536 cm$^{-1}$; $^1$H-NMR (60 MHz, CDCl$_3$) δ 1.6–2.3 (complex signal, approx. 40H), 2.75 (s, 3H, CH$_3$-Ms), 3.35 (m, 5H), 3.9 (m, 2H), 4.7 (t, J=6 Hz, CH$_2$N), 8.1 (m, 2H), 8.5 (m, 1H), 9.4 (d, J=6Hz, 1H).

Analysis calculated for C$_{31}$H$_{54}$NO$_5$S. ½ H$_2$O: C 63.9%; H 13.9%; N 2.4%. Found: C 63.72%; H 13.45%; N 2.21%.

EXAMPLE 75

(±)-cis,
trans-3-[6-[(4-tetradecyltetrahydrofuran-2-yl)methoxy]-6-oxohexyl]thiazolium 4-methylbenzenesulfonate (a) (±)-cis,
trans-6-[(4-tetradecyltetrahydrofuran-2-yl)methoxy]-6-oxohexyl 4-methylbenzenesulfonate To a solution of the compound prepared in example 70c (0.6 g, 2 mmol) in methylene chloride (5 mL) and pyridine (0.2 mL) 0.43 g (2.3 mmol) of 6-(methylbenzenesulfonyl)hexanoyl chloride was added and the mixture was stirred at room temperature for 12 h. The solvent was evaporated and the residue was purified by column chromatography (silica gel, hexane: ethyl acetate, 20%) to afford 1 g of a white solid (88% yield).

IR (KBr) ν: 2921, 2850, 1732, 1596, 1463, 1361, 1187, 1176 cm$^{-1}$; $^1$H-NMR (60 MHz, CDCl$_3$) δ: 0.6–1.9 (complex signal, approx. 38H), 2.28 (t, J=7Hz, 2H), 2.35 (s, 3H, Tos-CH$_3$), 3.3 (m, 1H), 4.0 (m, 6H), 7.3 (d, J=8 Hz, 2H), 7.75 (d, J=8Hz, 2H).

(b) Preparation of the title compound of this example

To a solution of the compound prepared in example 75a (1 g, 1.7 mmol) in chloroform (7 mL) and acetonitrile (14 mL) 0.9 mL of thiazole was added and the mixture was refluxed under argon atmosphere for 48 h. The mixture was allowed to cool down and diethyl ether was added to induce the precipitation of a solid that was filtered, dried and recrystallized from methylene chloride: diethyl ether, to afford 0.60 g of a white solid (49% yield).

mp: 78.7°–91.5° C.; IR (KBr) ν: 2915, 2846, 1730, 1465, 1210, 1192, 1035, 1011 cm$^{-1}$; $^1$H-NMR (200 MHz, CDCl$_3$) δ: 0.88 (t, J=6Hz, 3H), 1.26 (complex signal, approx. 29H), 1.7 (m, 5H), 2.24 (m, 4H), 2.34 (s, 3H, Tos-CH$_3$), 3.36 (m, 1H), 4.00 (m, 4H), 4.57 (t, J=6Hz, 2H, CH$_2$N), 7.14 (d, J=8HZ, 2H), 7.72 (d, J=8Hz, 2H), 8.28 (m, 1H, thiazole), 8.42 (m, 1H, thiazole), 10.70 (m, 1H, thiazole).

Analysis calculated for C$_{35}$H$_{57}$NO$_6$S$_2$ : C 64.5%; H 8.8%; N 2.1%. Found: C 64.47%; H 9.19%; N 1.90%.

EXAMPLE 76

(±)-cis,
trans-[6-tetradecyltetrahydrofuran-2-yl)methoxy]-N,N,N-trimethylhexanaminium 4-methyl-benzenesulfonate Following the procedure described in example 71a, and using instead of the compound prepared in example 70f, an equivalent amount of compound prepared in example 75a, a white solid was obtained (87% yield).

mp: 149.9°–160.8° C.; IR (KBr) ν: 3029, 2915, 2847, 1735, 1482, 1194, 1171, 1120, 1033, 1010, 819, 683, 563 cm$^{-1}$; $^1$H-NMR (60 MHz, CDCl$_3$) δ: 0.6–1.8 (complex signal, approx. 38H), 2.35 (s, 3H, Tos-CH$_3$), 2.3 (m, 2H), 3.3 (s, 9H, N(CH$_3$)$_3$), 3.35 (m, 6H), 4.05 (m, 3H), 7.2 (d, J=8Hz, 2H).

Analysis calculated for C$_{35}$H$_{63}$NO$_6$S: C 67.2%; H 10.1%; N 2.2%. Found: C 67.63%; H 10.54%; N 2.02%.

EXAMPLE 77

(±)-cis,
trans-1-[6-[(4-tetradecyltetrahydrofuran-2-yl)methoxy]-6-oxohexyl]pyridinium 4-methylbenzenesulfonate Following the procedure described in example 70g, and using instead of the compound prepared in example 70f, the compound prepared in example 75a, and instead of thiazole, an equivalent amount of pyridine, a white solid was obtained (60% yield).

mp: 104.4°–108.5° C.; IR (KBr) v: 2914, 2846, 1725, 1635, 1485, 1464, 1210, 1199, 1034, 1011, 819, 774, 683, 561 cm$^{-1}$; $^1$H-NMR (200MHz, CDCl$_3$) δ: 0.84 (t, J=6Hz, 3H), 1.1–1.3 (complex signal, approx. 34H), 1.60 (m, 2H), 1.86 (m, 2H), 2.18 (m, 1H), 2.25 (t, J=7.3Hz, 2H, CH$_2$CO), 2.30 (s, 3H, Tos-CH$_3$), 3.36 (m, 1H), 4.0 (m, 4H), 4.78 (t, J=6.7Hz, 2H, CH$_2$N), 7.10 (d, J=7.7Hz, 2H), 7.70 (d, J=7.7Hz, 2H), 7.98 (t, J=6.9Hz, 2H, pyridine), 8.38 (t, J=7.7Hz, 1H, pyridine), 9.16 (d, J=5.8Hz, 2H, pyridine).

Analysis calculated for C$_{37}$H$_{59}$NO$_6$S: C 68.8%; H 9.2%; N 2.2%. Found: C 68.42%; H 9.65%; N 2.07%.

EXAMPLE 78

(±)-cis,
trans-3-methyl-1-[6-[(4-tetradecyltetrahydrofuran-2-yl)methoxy]-6-oxohexyl]imidazolium 4-methylbenzenesulfonate Following the procedure described in example 70g, and using instead of the compound prepared in example 70f, the compound prepared in example 75a and instead of thiazole, an equivalent amount of 1-methylimidazole, a white solid was obtained (47% yield).

mp: 57.5°–88.3° C.; IR (KBr) v: 3096, 2920, 2850, 1731, 1634, 1567, 1463, 1192, 1122, 1034, 1011, 814, 683, 569 cm$^{-1}$; $^1$H-NMR (200 MHz, CDCl$_3$) δ: 0.88 (t, J=6.5Hz, 3H), 1.26 (complex signal, approx. 31H), 1.58 (m, 2H), 1.82 (m, 2H), 2.21 (m, 1H), 2.30 (m, 2H), 2.34 (s, Tos-CH$_3$), 3.38 (m, 1H), 3.96 (s, CH$_3$-N), 4.00 (m, 2H), 4.16 (m, 2H), 7.15 (d, J=7.9Hz, 2H), 7.33 (m, 1H, imidazole), 7.43 (m, 1H, imidazole), 7.75 (d, J=7.9Hz, 2H), 9.75 (m, 1H, imidazole).

Analysis calculated for C$_{36}$H$_{60}$N$_2$O$_6$S: C 66.6%; H 9.2%; N 4.3%. Found: C 66.23%; H 9.66%; N 4.29%.

EXAMPLE 79

(±)-cis,
trans-3-[4-[(4-tetradecyltetrahydrofuran-2-yl)methoxy]-butyl]thiazolium 4-methylbenzenesulfonate (a) (±)-cis,
trans-4-[(4-tetradecyltetrahydrofuran-2-yl)methoxy]butyl, tetrahydropiran-2-yl ether Following the procedure described in example 70d, and using instead of 6-tetrahydropiranyl-2-oxy)hexyl 4-methylbenzenesulfonate, an equivalent amount of 4-(tetrahydropiranyl-2-oxy)butyl 4-methylbenzenesulfonate, a colorless oil was obtained (31% yield).

IR (film) v: 2918, 2848, 1463, 1172, 1137, 1119, 1077, 1061, 1035 cm$^{-1}$; $^1$H-NMR (60 MHz, CDCl$_3$) δ: 0.7–2.2 (complex signal, approx. 39H), 3.3–4.3 (m, 11H), 4.6 (m, 1H).

(b) (±)-cis,
trans-4-[(4-tetradecyltetrahydrofuran-2-yl)methoxy]butan-1-ol

Following the procedure described in example 70e, and using instead of the compound prepared in example 70d, an equivalent amount of the compound prepared in example 79a, a colorless oil was obtained (80% yield).

$^1$H-NMR (60 MHz, CDCl$_3$) δ: 0.6–2.4 (complex signal, approx. 36H), 2.8 (m, 1H, OH), 3.55 (m, 6H), 4.05 (m, 3H).

(c) (±)-cis,
trans-4-[(4-tetradecyltetrahydrofuran-2-yl)methoxy]butyl 4-methylbenzenesulfonate Following the procedure described in example 70f, and using instead of the compound prepared in example 70e, an equivalent amount of the compound prepared in example 79b, a white solid was obtained (86% yield).

mp: 53.5°–54.6° C.; IR (KBr) v: 2914, 2847, 1594, 1465, 1354, 1193, 1015 cm$^{-1}$; $^1$H-NMR (60 MHz, CDCl$_3$) δ: 0.6–2.4 (complex signal, approx. 37H), 2.5 (s, 3H, Tos-CH$_3$), 3.35 (m, 2H), 4.1 (m, 7H), 7.35 (d, J=8Hz, 2H), 7.85 (d, J=8Hz, 2H).

Analysis calculated for C$_{30}$H$_{52}$O$_5$S: C 68.7%; H 9.9%. Found: C 69.03%; H 10.28%.

(d) Preparation of the title compound of this example

Following the procedure described in example 70g, and using instead of the compound prepared in example 70f, an equivalent amount of the compound prepared in example 79c, a white solid was obtained (56% yield).

mp: 75.8°–88.1° C.; IR (KBr) v: 3546, 3476, 3076, 2951, 2917, 2848, 1626, 1464, 1217, 1193, 1121, 1034, 683 cm$^{-1}$; $^1$H-NMR (60 MHz, CDCl$_3$) δ: 0.7–2.2 (complex signal, approx. 36H), 2.25 (s, 3H, Tos-CH$_3$), 3.25 (m, 1H), 3.6–4.9 (m, 8H), 7.15 (d, J=8Hz, 2H), 7.75 (d, J=8Hz, 2H), 8.25 (m, 1H, thiazole), 8.45 (m, 1H, thiazole), 10.50 (m, 1H, thiazole).

Analysis calculated for C$_{33}$H$_{55}$NO$_5$S$_2$.H$_2$O: C 63.2%; H 9.1%; N 2.2%. Found: C 63.51%; H 9.39%; N 2.47%.

EXAMPLE 80

(±)-cis,
trans-2-methyl-1-[4-[(4-tetradecyltetrahydrofuran-2-yl)methoxy]butyl]pyridinium 4-methylbenzenesulfonate Following the procedure described in example 70f, and using instead of the compound prepared in example 70e, an equivalent amount of compound prepared in example 79b, and instead of thiazole, 2-methylpyridine, a white solid was obtained (28% yield). mp: 136.9°–148.7° C.; IR (KBr) v: 3045, 2917, 2848, 1626, 1464, 1218, 1194, 1120, 1032, 1009, 682 cm$^{-1}$.

Analysis calculated for C$_{36}$H$_{59}$NO$_5$S: C 70.0%; H 9.6%; N 2.3%. Found: C 70.31%; H 9.98%; N 2.20%.

EXAMPLE 81

(±)-cis,
trans-4-methyl-4-[4-[(4-tetradecyltetrahydrofuran-2-yl)methoxy]butyl]morpholinium 4-methylbenzenesulfonate Following the procedure described in example 70f, and using instead of the compound prepared in example 70e, an equivalent amount of compound prepared in example 79b, and instead of thiazole, N-methylmorpholine, a cream-colored solid was obtained (31% yield).

mp: 53.33°–63.1° C.; IR (KBr) v: 3434, 2919, 2849, 1463, 1191, 1121, 1035, 1012 cm$^{-1}$; $^1$H-NMR (60 MHz, CDCl$_3$) δ: 0.7–1.6 (complex signal, approx. 36H), 2.30 (s, 3H, Tos-CH$_3$), 3.40 (s, 3H, CH$_3$N), 2.8–4.3 (complex signal, approx. 20H), 7.15 (d, J=8Hz), 7.8 (d, J=8Hz, 2H).

Analysis calculated for $C_{35}H_{62}NO_6S \cdot 2H_2O$: C 63.6%; H 10.0%; N 2.1%. Found: C 63.76%; H 9.75%; N 2.51%.

EXAMPLE 82

(±)-cis, trans-3-[7-[(4-tetradecyltetrahydrofuran-2-yl)methoxy]-heptyl]thiazolium 4-methylbenzenesulfonate

(a) (±)-cis, trans-7-[(4-tetradecyltetrahydrofuran-2-yl)methoxy]-heptyl, tetrahydropiran-2-yl ether Following the procedure described in example 70d, and using instead of 6-(tetrahydropiranyl-2-oxy)hexyl 4-methylbenzenesulfonate, an equivalent amount of 7-(tetrahydropiranyl-2-oxy)butyl 4-methylbenzenesulfonate, a colorless oil was obtained (58% yield). $^1$H-NMR (60 MHz, CDCl$_3$) δ: 0.6–2.2 (complex signal, approx. 46H), 3.3–4.3 (m, 1H, OCHO).

(b) (±)-cis, trans-7-[(4-tetradecyltetrahydrofuran-2-yl)methoxy]-heptan-1-ol Following the procedure described in the example 70e, and using instead of the compound prepared in example 70d, an equivalent amount of the compound prepared in example 82a, a colorless solid was obtained (99% yield).

IR (film) ν: 3444, 2925, 2851, 1462, 1312, 1120 cm$^{-1}$; $^1$H-NMR (60 MHz, CDCl$_3$) δ: 0.6–2.4 (complex signal, approx. 41H), 2.8 (m, 1H, OH), 3.35 (m, 6H), 3.95 (m, 3H).

(c) (±)-cis, trans-7-[(4-tetradecyltetrahydrofuran-2-yl)methoxy]-heptyl 4-methylbenzenesulfonate Following the procedure described in example 70f, and using instead of the compound prepared in example 70e, an equivalent amount of compound prepared in example 82b, a white solid was obtained (51% yield).

IR (KBr) ν: 2921, 2850, 1595, 1462, 1361, 1187, 1176, cm$^{-1}$; $^1$H-NMR (60MHz, CDCl$_3$) δ: 0.6–2.3 (complex signal, approx. 46H), 2.45 (s, 3H, Tos-CH$_3$), 3.45 (m, 5H), 4.0 (m, 4H), 7.4 (d, J=8Hz, 2H), 7.85 (d, J=8Hz, 2H).

(d) Preparation of the Title Compound of this Example

Following the procedure described in example 70g, and using instead of the compound prepared in example 70f, an equivalent amount of the compound prepared in example 82c, a white solid was obtained (70% yield).

mp: 78.0°–87.7° C.; IR (KBr) ν: 3136, 2915, 2846, 1560, 1464, 1213, 1193, 1121, 1034, 1010 cm$^{-1}$; $^1$H-NMR (60 MHz, CDCl$_3$) δ: 0.6–2.2 (complex signal, approx. 46H), 2.4 (s, 3H, Tos-CH$_3$), 3.4 (m, 5H), 4.0 (m, 2H), 4.6 (m, 2H), 7.25 (d, J=8Hz, 2H), 7.85 (d, J=8Hz, 2H), 8.45 (m, 2H, thiazole), 10.8 (m, 1H, thiazole).

Analysis calculated for $C_{36}H_{61}O_5NS_2$: C 66.3%; H 9.4%; N 2.1%. Found: C 66.27%; H 9.95%; N 2.01%.

EXAMPLE 83

(±)-cis-3-[6-[(4-tetradecyltetrahydrofuran-2-yl)methoxy]hexyl]thiazolium 4-methylbenzenesulfonate

(a) N,N-dimethylhexadecanamide

A mixture of 100 g of hexadecanoic acid and 100 mL of thionyl chloride was refluxed for 1 h. Afterwards, 200 mL of benzene was added and the solvent was distilled at reduced pressure, to afford the crude acid chloride.

IR (film) ν: 2923, 2851, 1798, 1464, 1402 cm$^{-1}$.

The crude acid chloride prepared in that way was dissolved in 120 mL of N,N-dimethylformamide and the solution was heated at 150° C. for 4 h. The mixture was cooled down and the resulting precipitate was filtered, washed with water and dried, to afford 115.0 g of a solid that was recrystallized from pentane to give 100.4 g of a white solid (95% yield).

mp: 38.1°–39,2° C.; IR (KBr) ν: 2916, 2846, 1704, 1644, 1629, 1462, 1408, 1392, 1262, 1143 cm$^{-1}$; $^1$H-NMR (60 MHz, CDCl$_3$) δ: 0.5–1.9 (complex signal, approx. 29H), 2.3 (m, 2H), 3.0 (m, 6H).

(b) N,N-dimethyl-2-allylhexadecanamide

To a solution of n-butyl lithium (hexane, 44 mmol) in 120 mL of anhydrous tetrahydrofuran at 0° C., under nitrogen atmosphere it was added 6.2 mL (44 mmol) of diisopropylamine. After 5 min., 10 g (35 mmol) of N,N-dimethylhexadecanamide was added dropwise and the solution was stirred for 1 h at the same temperature. To the solution 3.7 mL (44 mmol) of allyl bromide were added and the mixture was stirred at room temperature for 12 h. Afterwards the solution was poured on water and the resulting mixture was acidified with 12 N HCl, and extracted twice with ethyl acetate. The organic phase was dried over anhydrous sodium sulfate and after evaporation of the solvent it was obtained 10.94 g of an oil that was purified by column chromatography (silica gel, hexane: ethyl acetate 15%). In that way, 10.2 g of a colorless oil was obtained (85% yield).

IR (film) ν: 2920, 2850, 1740, 1640, 1480 cm$^{-1}$; $^1$H-NMR (60 MHz, CDCl$_3$) δ: 0.90 (m, 3H), 1.2–2.8 (complex signal, approx. 31H), 3.0 (s, 3H), 3.1 (s, 3H), 4.9–6.2 (m, 3H).

(c) (±)-cis, trans-2-iodomethyl-5-oxo-4-tetradecyltetrahydrofuran

To a solution of 8.25 g (25.5 mmol) of N,N-dimethyl-2-allylhexadecanamide in THF/ H$_2$O (1:3 v/v, 120 mL) 9.69 g (38.2 mmol) of iodine was added at room temperature and the reaction mixture was stirred for 3 days. Then, the mixture was diluted with 200 mL of ethyl acetate, washed twice with 10% sodium thiosulfate and extracted twice with ethyl acetate. The combined organic layers were dried with sodium sulfate and after evaporation of the solvent it was obtained 11.3 g of a solid that was purified by column chromatography (silica gel, hexane: ethyl acetate 7%) to give 6.98 g of the trans isomer, 0.91 g of a mixture of the cis and trans isomers and 0.42 g of the cis isomer (overall yield 87%).

Trans isomer (less polar compound in TLC):

mp: 65.6°–65.7° C.; IR (KBr) ν: 2914, 2845, 1750, 1466, 1171, 1149, 1011 cm$^{-1}$; $^1$H-NMR (200 MHz, CDCl$_3$) δ: 0.88 (t, J=6.0Hz, 3H), 1.26 (complex signal, 26H), 1.82 (m, 1H), 2,20 (m, 2H), 2.72 (m, 1H), 3.28 (half ABC system, $J_{AB}$=10.2Hz, $J_{AC}$=7.4Hz, CHI), 3.38 (half ABC system, $J_{AB}$=10.2Hz, $J_{BC}$=4.5Hz, CHI), 4.60 (t of t, $J_1$=7.9Hz, $J_2$=4.5 Hz, 1H).

Analysis calculated for $C_{19}H_{34}IO_2$: C 54.0%; H 8.3%; I 30.1%. Found: C 53.83%; H 8.71%; I 29.84%.

Cis isomer (more polar compound in TLC):

mp: 67.4°–67.8° C.; IR (KBr) ν: 2952, 2916, 2845, 1758, 1466, 1191, 1178, 994 cm$^{-1}$; $^1$H-NMR (200 MHz, CDCl$_3$) δ: 0.88 (t, 3H, J=6.0 Hz), 1.26 (complex signal, 26H), 1.58 (m, 1H), 1.92 (m, 1H), 2.66 (m, 2H), 3.26 (half ABC system, $J_{AB}=10.5Hz$, $J_{AC}=7.4$ Hz, CHI), 3.46 (half ABC system, $J_{AB}=10.5$ Hz, $J_{BC}=4.3$ Hz, CHI), 4.4 (m, 1H).

Analysis calculated for $C_{19}H_{34}IO_2$: C 54.0%; H 8.3%; I 30.1%. Found: C 54.4%; H 8.51%; I 29.75%.

(d) (±)-cis-(4-tetradecyltetrahydrofuran-2-yl)methanol

To a solution of the trans isomer prepared in example 83c (4 g, 9.4 mmol) in anhydrous tetrahydrofuran (13 mL) under argon atmosphere it was added 10.8 mL (21.6 mmol) of a 2.0M solution of dimethylsulfide.diborane complex in tetrahydrofuran and the mixture was stirred for 48 h. Afterwards, methanol was added to destroy the excess of hydride and the mixture was concentrated to dryness. The residue was treated with ethyl acetate and washed with 1M pH 7 phosphate buffer. After drying over anhydrous sodium sulfate and evaporating the solvent 3.8 g of an oil was obtained. IR (film) v: 3339, 2920, 2852, 1462, 1332, 1180 cm$^{-1}$.

$^1$H-NMR (60 MHz, CDCl$_3$) δ: 0.5–1.9 (complex signal, approx. 31H), 2.9 (s, 2H), 3.2 (q, 2H), 3.55 (m, 3H).

The crude prepared in that way was dissolved in methanol (70 mL), 2.6 g of potassium carbonate was added and the resulting mixture was stirred for 1 h. The solvent was eliminated and the residue was treated with 1M pH=7 phosphate buffer and ethyl acetate. The organic layer was dried and concentrated to give 2.5 g of an oil that was purified by column chromatography (silica gel, hexane:ethyl acetate, 25%). 2.4 g of pure cis alcohol was obtained (86% yield).

mp: 34.6°–35.3° C.; IR (film) v: 3439, 2920, 2849, 1462, 1376, 1050, 817, 721 cm$^{-1}$; $^1$H-NMR (60 MHz, CDCl$_3$) δ: 0.6–2.5 (complex signal, approx. 32H), 3.33 (m, 2H), 3.55 (m, 2H), 3.93 (m, 2H). $^{13}$C-NMR (50.3 MHz, CDCl$_3$) δ 14.11 (CH$_3$), 22.70 (CH$_2$), 28.59 (CH$_2$), 29.36 (CH$_2$), 29.57 (CH$_2$), 29.69 (CH$_2$), 29.75 (CH$_2$), 31.93 (CH$_2$), 33.10 (CH$_2$), 34.24 (CH$_2$), 40.18 (CH), 54.97 (CH$_2$), 73.45 (CH$_2$), 80.04 (CH).

Analysis calculated for $C_{19}H_{38}O_2$: C 76.5%; H 12.8%. Found: C 76.58%; H 12.90%.

(e)
(±)-cis-6-[(4-tetradecyltetrahydrofuran-2-yl)methoxy]-hexyl, tetrahydropiran-2-yl ether Following the procedure described in example 70d, and using instead of a (1:1) mixture of the cis and trans isomers prepared in example 70c, an equivalent amount of the pure cis isomer prepared in example 83d, the desired product was obtained as a colorless oil (56.6% yield).

IR (film) v: 2919, 2848, 1462, 1349, 1163, 1120, 1077, 1034, 734, 721 cm$^{-1}$; $^1$H-NMR (60 MHz, CDCl$_3$) δ: 0.8–2.2 (complex signal, approx. 46H), 3.2–4.2 (m, 11H), 4.55 (m, 1H, OCHO).

(f)
(±)-cis-6-[(4-tetradecyltetrahydrofuran-2-yl)methoxy]-hexan-1-ol

Following the procedure described in example 70e, and using instead of a (1:1) mixture of the cis and trans isomers prepared in example 70d, an equivalent amount of the pure cis isomer prepared in example 83e, the desired product was obtained as a colorless oil (79% yield).

IR (film) v: 3415, 2920, 2850, 1463, 1370, 1238, 1112, 1049, 722 cm$^{-1}$; $^1$H-NMR (60 MHz, CDCl$_3$) δ: 0.6–2.5 (complex signal, approx. 40H), 3.25 (s, 1H, OH), 3.46 (m, 6H), 4.0 (m, 3H).

(g)
(±)-cis-6-[(4-tetradecyltetrahydrofuran-2-yl)methoxy]-hexyl 4-methylbenzenesulfonate Following the procedure described in example 70f, and using instead of a (1:1) mixture of the cis and trans isomers prepared in example 70e, an equivalent amount of the pure cis isomer prepared in example 83f, the desired compound was obtained as a white solid (16% yield).

IR (KBr) v: 2920, 2850, 1595, 1462, 1362, 1187, 1176, 1097 cm$^{-1}$; $^1$H-NMR (60 MHz, CDCl$_3$) δ: 0.6–2.3 (complex signal, approx. 40H), 3.90 (s, 3H, CH$_3$-Tos), 3.35 (m, 5H), 3.90 (m, 4H).

(h) Preparation of the title Compound of this Example

Following the procedure described in example 70 g and using instead of a (1:1) mixture of the cis and trans isomers prepared in example 70f, an equivalent amount of the pure cis isomer prepared in example 83 g, a white solid was obtained (63% yield). mp: 114.7° C.; IR (KBr) v: 3420, 3126, 2913, 2846, 1560, 1464, 1212, 1192, 1121, 1034, 1010, 683 cm$^{-1}$.

Analysis calculated for $C_{35}H_{59}NO_5S \cdot H_2O$: C 64.1%; H 9.0%; N 2.1%. Found: C 64.29%; H 9.45%; N 2.09%.

EXAMPLE 84

(±)-trans-3-[6-[(4-tetradecyltetrahydrofuran-2-yl)methoxy]hexyl]thiazolium 4-methylbenzenesulfonate (a)
(±)-cis-(5-oxo-4-tetradecyltetrahydrofuran-2-yl)methanol To a solution of the trans isomer of the compound prepared in example 83c (6 g, 14 mmol) in anhydrous tetrahydrofuran (100 mL) at 0° C. a solution of lithium hydroxide monohydrate (1.29 g, 30 mmol) in 60 mL of water was added and the mixture was stirred at room temperature for 4 h. Afterwards, it was acidified with 1N HCl, the aqueous phase was saturated with sodium chloride and was extracted twice with ethyl acetate. After drying the combined organic layers and evaporating the solvent a solid product was obtained that was purified by column chromatography (silica gel, chloroform:ethyl acetate 15%). In that way 4 g of a white solid was obtained (93% yield).

mp: 90.4°–90.7° C.; IR (KBr) v: 3327, 2951, 2845, 1747, 1461, 1205, 1050, 950, 894, 722 cm$^{-1}$; $^1$H-NMR (200 MHz, CDCl$_3$) δ: 0.88 (t, J=6.5Hz, CH$_3$), 1.22–1.52 (complex signal, approx. 27H), 1.9 (m, 3H), 2.35 (dd of d, $J_1=6.1Hz$, $J_2=8.9$ Hz, $J_3=12.4$ Hz, 1H), 2.64 (m, 1H), 3.63 (m, 1H), 3.90 (m, 1H), 4.52 (m, 1H).

Analysis calculated for $C_{19}H_{36}O_3$: C 73.0%; H 11.5%. Found: C 73.02%; H 11.36%.

(b)
(±)-cis-(5-oxo-4-tetradecyltetrahydrofuran-2-yl)methyl 4-methylbenzenesulfonate Following the procedure described in example 70f, and using instead of the compound prepared in example 70e, an equivalent amount of the compound prepared in example 84a, a white solid was obtained (54% yield).

mp: 83.9° C.; IR (KBr) v: 2916, 2846, 1758, 1596, 1466, 1356, 1174, 989, 980, 836 cm$^{-1}$; $^1$H-NMR (60 MHz, CDCl$_3$) δ: 0.6–2.2 (complex signal, approx. 32H), 2.33 (m, 1H), 2.42 (s, 3H, Tos-CH$_3$), 4.15 (m, 2H), 4.50 (m, 1H), 7.38 (d, J=8 Hz, 2H), 7.85 (d, J=8 Hz, 2H).

Analysis calculated for C$_{26}$H$_{42}$O$_5$S: C 66.9%; H 9.0%. Found: C 66.79%; H 9.33%.

(c)
(±)-trans-(4-tetradecyltetrahydrofuran-2-yl)methanol

Following the procedure described in example 83d, and using instead of the compound prepared in example 83c, an equivalent amount of compound prepared in example 84b, a colorless oil was obtained (76% yield).

mp: 37.2°–38.6° C.; IR (KBr) ν: 3419, 2918, 2846, 1465, 1423, 1047, 929, 720 cm$^{-1}$; $^1$H-NMR (60 MHz, CDCl$_3$) δ: 0.6–2.5 (complex signal, approx. 32H), 3.05 (s, 1H, OH), 3.43 (m, 3H), 3.97 (m, 2H); $^{13}$C-NMR (50.31 MHz, CDCl$_3$) δ: 14.11 (CH$_3$), 22.68 (CH$_2$), 28.46 (CH$_2$), 29.35 (CH$_2$), 29.57(CH$_2$), 29.60 (CH$_2$), 29.66 (CH$_2$), 29.74 (CH$_2$), 31.91 (CH$_2$), 33.14 (CH$_2$), 33.78 (CH$_2$), 39.44 (CH), 65.28 (CH$_2$), 73.84 (CH$_2$), 78.94 (CH).

Analysis calculated for C$_{19}$H$_{38}$O$_2$: C 76.5%; H 12.75%. Found: C 76.50%; H 13.37%.

(d)
(±)-trans-6-[(4-tetradecyltetrahydrofuran-2-yl)methoxy]hexyl tetrahydropiran-2-yl ether Following the procedure described in example 70d, and using instead of a (1:1) mixture of the cis and trans isomers prepared in example 70c, an equivalent amount of the pure trans isomer prepared in example 84c, a colorless oil was obtained (68% yield).

$^1$H-NMR (60 MHz, CDCl$_3$) δ: 0.6–2.1 (complex signal, 46H), 3.7 (m, 11H), 4.98 (m, 1H, OCHO).

(e)
(±)-trans-6-[(4-tetradecyltetrahydrofuran-2-yl)methoxy]hexan-1-ol

Following the procedure described in example 70e, and using instead of a (1:1) mixture of the cis and trans isomers prepared in example 70d, an equivalent amount of the pure trans isomer prepared in example 84d, a colorless oil was obtained (76% yield).

IR (film) ν: 3412, 2920, 2850, 1462, 1375, 1114, 1057 721 cm$^{-1}$; $^1$H-NMR (60 MHz, CDCl$_3$) δ: 0.6–2.0 (complex signal, 40H), 3.48 (m, 6H), 4.0 (m, 3H).

(f)
(±)-trans-6-[(4-tetradecyltetrahydrofuran-2-yl)methoxy]hexyl 4-methylbenzenesulfonate Following the procedure described in example 70f, and using instead of a (1:1) mixture of the cis and trans isomers prepared in example 70e, an equivalent amount of the pure trans isomer prepared in example 84e, a white solid was obtained (40% yield).

IR (KBr) ν: 2921, 2850, 1595, 1462, 1361, 1187, 1176, 1097 cm$^{-1}$.

(g) Preparation of the Title Compound of this Example

Following the procedure described in example 70 g, and using instead of a (1:1) mixture of the cis and trans isomers prepared in example 70f, an equivalent amount of the pure trans isomer prepared in example 84f, a white solid was obtained (80% yield).

mp: 78.4°–83.4° C.; IR (KBr) ν: 3415, 3129, 2916, 2846, 1560, 1464, 1212, 1192, 1121, 1034, 1010, 683 cm$^{-1}$.

Analysis calculated for C$_{35}$H$_{59}$NO$_5$S$_2$·½H$_2$O: C 65.0%; H 9.3%; N 2.3%. Found: C 65.08%; H 9.63%; N 2.21%.

EXAMPLE 85

(±)-cis, trans-3-[5-[(4-tetradecyltetrahydrofuran-2-yl)methoxy]pentyl]thiazolium 4-methylbenzenesulfonate Following the procedure described in example 70, but using 5-(tetrahydropiranyl-2-oxy)pentyl 4-methylbenzenesulfonate instead of 6-(tetrahydropiranyl-2-oxy)hexyl 4-methylbenzenesulfonate, the title compound of this example was obtained in a similar yield.

EXAMPLE 86

(±)-cis, trans-3-[8-[(4-tetradecyltetrahydrofuran-2-yl)methoxy]octyl]thiazolium 4-methylbenzenesulfonate Following the procedure described in example 70, but using 8-(tetrahydropiranyl-2-oxy)octyl 4-methylbenzenesulfonate instead of 6-(tetrahydropiranyl-2-oxy)hexyl 4-methylbenzenesulfonate, the title compound of this example was obtained in a similar yield.

EXAMPLE 87

(±)-cis, trans-3-[4-[[[(4-tetradecyltetrahydrofuran-2-yl)methoxy]carbonyl]amino]butyl]thiazolium 4-methylbenzenesulfonate Following the procedure described in example 75, but using 4-(4-methylbenzenesulfonyloxy)butyl isocyanate instead of 6-(4-methylbenzenesulfonyloxy)hexanoyl chloride, the title compound of this example was obtained in a similar yield.

EXAMPLE 88

(±)-cis, trans-3-[5-[[[(4-tetradecyltetrahydrofuran-2-yl)methoxy]carbonyl]amino]pentyl]thiazolium 4-methylbenzenesulfonate Following the procedure described in example 75, but using 5-(4-methylbenzenesulfonyloxy)pentyl isocyanate instead of 6-(4-methylbenzenesulfonyloxy)hexanoyl chloride, the title compound of this example was obtained in a similar yield.

EXAMPLE 89

(±)-cis, trans-3-[4-[[[(4-tetradecyltetrahydrofuran-2-yl)methoxy]carbonyl]oxy]butyl]thiazolium 4-methylbenzenesulfonate Following the procedure described in example 75, but using 4-(4-methylbenzenesulfonyloxy)butyl chlorocarbonate instead of 6-(4-methylbenzenesulfonyloxy)hexanoyl chloride, the title compound of this example was obtained in a similar yield.

EXAMPLE 90

(±)-cis, trans-3-[5-[[[(4-tetradecyltetrahydrofuran-2-yl)methoxy]carbonyl]oxy]pentyl]thiazolium 4-methylbenzenesulfonate.

Following the procedure described in example 75, but using 5-(4-methylbenzenesulfonyloxy)pentyl chlorocarbonate instead of 6-(4-methylbenzenesulfonylox-

EXAMPLE 91

(±)-cis,
trans-3-[5-[(4-hexadecyltetrahydrofuran-2-yl)methoxy]-pentyl]thiazolium 4-methylbenzenesulfonate Following the procedure described in example 85, but using ethyl stearate instead of ethyl hexadecanoate, the title compound of this example was obtained in a similar yield.

EXAMPLE 92

(±)-cis,
trans-3-[6-[(4-pentadecyltetrahydrofuran-2-yl)methoxy]hexyl]thiazolium 4-methylbenzenesulfonate Following the procedure described in example 70, but using ethyl heptadecanoate instead of ethyl hexadecanoate, the title compound of this example was obtained in a similar yield.

EXAMPLE 93

(±)-cis,
trans-3-[6-[(4-hexadecyltetrahydrofuran-2-yl)methoxy]-hexyl]thiazolium 4-methylbenzenesulfonate Following the procedure described in example 70, but using ethyl stearate instead of ethyl hexadecanoate, the title compound of this example was obtained in a similar yield.

EXAMPLE 94

(±)-cis,
trans-3-[6-[(4-heptadecyltetrahydrofuran-2-yl)methoxy]hexyl]thiazolium 4-methylbenzenesulfonate Following the procedure described in example 70, but using ethyl nonadecanoate instead of ethyl hexadecanoate, the title compound of this example was obtained in a similar yield.

EXAMPLE 95

(±)-cis,
trans-3-[7-[(4-pentadecyltetrahydrofuran-2-yl)methoxy]heptyl]thiazolium 4-methylbenzenesulfonate Following the procedure described in example 82, but using ethyl heptadecanoate instead of ethyl hexadecanoate, the title compound of this example was obtained in a similar yield.

EXAMPLE 96

(±)-cis,
trans-3-[7-[(4-hexadecyltetrahydrofuran-2-yl)methoxy]-heptyl]thiazolium 4-methylbenzenesulfonate Following the procedure described in example 82, but using ethyl stearate instead of ethyl hexadecanoate, the title compound of this example was obtained in a similar yield.

EXAMPLE 96

(±)-cis,
trans-3-[7-[(4-heptadecyltetrahydrofuran-2-yl)methoxy]heptyl]thiazolium 4-methylbenzenesulfonate Following the procedure described in example 82, but using ethyl nonadecanoate instead of ethyl hexadecanoate, the title compound of this example was obtained in a similar yield.

EXAMPLE 98

(±)-cis,
trans-1-[7-[(4-hexadecyltetrahydrofuran-2-yl)methoxy]-heptyl]pyridinium 4-methylbenzenesulfonate Following the procedure described in example 96, but using pyridine instead of thiazole, the title compound of this example was obtained in a similar yield.

EXAMPLE 99

(±)-cis,
trans-3-[8-[(4-hexadecyltetrahydrofuran-2-yl)methoxy]octyl]thiazolium 4-methylbenzenesulfonate Following the procedure described in example 86, but using ethyl stearate instead of ethyl hexadecanoate, the title compound of this example was obtained in a similar yield.

EXAMPLE 100

(±)-cis,
trans-3-[8-[(4-heptadecyltetrahydrofuran-2-yl)methoxy]octyl]thiazolium 4-methylbenzenesulfonate Following the procedure described in example 86, but using ethyl nonadecanoate instead of ethyl hexadecanoate, the title compound of this example was obtained in a similar yield.

EXAMPLE 101

(±)-cis,
trans-3-[8-[(4-octadecyltetrahydrofuran-2-yl)methoxy]octyl]thiazolium 4-methylbenzenesulfonate Following the procedure described in example 86, but using ethyl eicosanoate instead of ethyl hexadecanoate, the title compound of this example was obtained in a similar yield.

EXAMPLE 102

(±)-cis,
trans-1-[8-[(4-hexadecyltetrahydrofuran-2-yl)methoxy]octyl]pyridinium 4-methylbenzenesulfonate Following the procedure described in example 99, but using pyridine instead of thiazole, the title compound of this example was obtained in a similar yield.

EXAMPLE 103

(±)-cis,
trans-3-[4-[[[(4-hexadecyltetrahydrofuran-2-yl)methoxy]carbonyl]amino]butyl]thiazolium 4-methylbenzenesulfonate Following the procedure described in example 87, but using ethyl stearate instead of ethyl hexadecanoate, the title compound of this example was obtained in a similar yield.

EXAMPLE 104

(±)-cis,
trans-3-[5-[[[(4-hexadecyltetrahydrofuran-2-yl)methoxy]carbonyl]amino]pentyl]thiazolium 4-methylbenzenesulfonate Following the procedure described in example 88, but using ethyl stearate instead of ethyl hexadecanoate, the title compound of this example was obtained in a similar yield.

EXAMPLE 105

(±)-cis, trans-3-[4-[[[(4-hexadecyltetrahydrofuran-2-yl)methoxy]carbonyl]oxy]butyl]thiazolium 4-methylbenzenesulfonate Following the procedure described in example 89, but using ethyl stearate instead of ethyl hexadecanoate, the title compound of this example was obtained in a similar yield.

EXAMPLE 106

(±)-cis, trans-3-[5-[[[(4-hexadecyltetrahydrofuran-2-yl)carbonyl]oxy]pentyl]thiazolium 4-methylbenzenesulfonate Following the procedure described in example 90, but using ethyl stearate instead of ethyl hexadecanoate, the title compound of this example was obtained in a similar yield.

EXAMPLE 107

(±)-cis, trans-2-[[[[(4-tetradecyltetrahydrofuran-2-yl)methoxy]carbonyl]amino]methyl]pyridine Following the procedure described in example 9, and using in place of the compound prepared in example 4b, the compound prepared in example 70c, the title compound was obtained as a white solid (76% yield).

mp: 57.0°-57.1° C.; IR(KBr) v: 3228, 3048, 2921, 2847, 1714, 1566, 1547, 1464, 1431, 1240, 1152 cm$^{-1}$. Analysis calculated for $C_{26}H_{44}O_3N_2 \cdot \frac{1}{2}H_2O$: C 70.7%; H 10.2%; N 6.3%. Found: C 70.85%; H 10.50%; N 6.39%.

EXAMPLE 108

(±)-cis, trans-2-[N-acetyl-[[[(4-tetradecyltetrahydrofuran-4-yl)methoxy]carbonyl]amino]methyl]pyridine Following the procedure described in example 24, and using in place of the compound prepared in example 23, the compound prepared in example 107, the title compound was obtained as a colourless oil (63% yield).

R$_f$: 0.38 (silicagel, hexane:ethyl acetate 1:1); IR (film) v: 3062, 2916, 2847, 1732, 1697, 1589, 1464, 1424, 1367, 1219 cm$^{-1}$; $^1$H-NMR (60 MHz, CDCl$_3$) δ: 0.9 (m, 3H), 0.95-2.3 (complex signal, 29 H), 2.60 (s, 3H), 3.25 (m, 1H), 3.90 (m, 4H), 5.05 (s, 2H), 7.10 (m, 2H), 7.6 (m, 1H), 8.55 (m, 1H).

EXAMPLE 109

(±)-cis,trans-N-methyl-2-[N-acetyl-[[[(4-tetradecyltetrahydrofuran-4-yl)methoxy]carbonyl]amino]methyl]pyridinium iodide Following the procedure described in example 12, and using in place of the compound prepared in example 11, the compound prepared in example 108, the title compound was obtained as yellowish solid (80% yield).

mp: 87.2°-88.4° C.; IR (KBr) v: 2917, 2846, 1757, 1682, 1627, 1465, 1354, 1225, 1214 cm$^{-1}$. Analysis calculated for $C_{29}H_{49}O_4N_2I$: C 56.5%; H 8.0%; N 4.5%. Found: C 56.90%; H 8.19%; N 4.25%.

EXAMPLE 110

(±)-cis,trans-N-ethyl-2-[N-acetyl-[[[(4-tetradecyltetrahydrofuran-4-yl)methoxy]carbonyl]amino]methyl]pyridinium iodide Following the procedure described in example 10, but using in place of the compound prepared in example 9, the compound prepared in example 108, the title compound was obtained as a yellowish solid (67% yield).

mp: 62.0°-63.5° C.; IR (KBr) v: 3409, 2915, 2845, 1747, 1675, 1625, 1463, 1367, 1211 cm$^{-1}$. Analysis calculated for $C_{34}H_{59}O_4N_2I \cdot \frac{1}{2}H_2O$: C 58.7%; H 8.6%; N 4.0%. Found: C 58.95%; H 8.60%; N 4.05%.

EXAMPLE 111

(±)-cis,trans-2-[[[[(4-octadecyltetrahydrofuran-2-yl)methoxy]carbonyl]amino]methyl]pyridine Following the procedure described in example 9, but using in place of the compound prepared in example 4b, (±)-cis,trans-(4-octadecyltetrahydrofuran-2-yl)methanol obtained as in example 70c starting from ethyl eicosanate, the title compound was obtained as a colourless oil and in quantitative yield.

R$_f$: 0.24 (silicagel, hexane:ethyl acetate 1:1); IR (film) v: 3317, 3050, 2913, 2846, 1714, 1588, 1566, 1463, 1211 cm$^{-1}$; $^1$H-NMR (90 MHz, CDCl$_3$) δ: 0.87 (m, 3H), 1.0-2.6 (complex signal, 36 H), 3.40 (m, 1H), 4.08 (m, 4H), 4.50 (d, J=5.4 Hz, 2 H), 5.96 (m, NH), 7.28 (m, 2H), 7.64 (t of d, Ja=7.6 Hz, Jb=1.8 Hz, 1H), 8.51 (d, J=4.6 Hz, 1H).

EXAMPLE 112

(±)-cis,trans-2-[N-acetyl-[[[(4-octadecyltetrahydrofuran-4-yl)methoxy]carbonyl]amino]methyl]pyridine Following the procedure described in example 24, but using in place of the compound prepared in example 23, the compound prepared in example 111, the title compound was prepared as a colourless oil (54% yield).

IR (KBr) v: 3063, 2916, 2847, 1730, 1696, 1589, 1463, 1367, 1220 cm$^{-1}$; $^1$H-NMR (90 Mz, CDCl$_3$) δ: 0.88 (m, 3H), 1.0-2.4 (complex signal, 36H), 2.63 (s, 3H), 3.27 (m, 1H), 4.07 (m, 4H), 5.10 (s, 2H), 7.12 (m, 2H), 7.61 (t of d, Ja=1.8 Hz, Jb=7.1 Hz, 1H), 8.50 (d of d, Ja=5.7 Hz, Jb=2.6 Hz, 1H).

EXAMPLE 113

(±)-cis, trans-N-ethyl-2-[N-acetyl-[[[(4-octadecyltetrahydrofuran-4-yl)methoxy]carbonyl]amino]methyl]pyridinium iodide Following the procedure described in example 10, but using in place of the compound prepared in example 9, the compound prepared in example 112, the title compound was obtained as a yellowish solid (56% yield).

mp: 57.0°-57.1° C.; IR(KBr) v: 3441, 2913, 2845, 1744, 1677, 1624, 1463, 1367, 1209 cm$^{-1}$; $^1$H-NMR (90 MHz, CDCl$_3$) δ: 0.88 (m, 3H), 1.25 (m, 34 H), 1.74 (t, J=7.3 Hz, 3H), 2.19 (m, 2H), 2.66 (s, 3H), 3.33 (t, J=7.2 Hz, 1H), 4.02 (m, 4H), 5.10 (q, J=7.3 Hz, 2H), 5.40 (s, 2H), 7.75 (d, J=7.4 Hz, 1H), 8.04 (t, J=7.1 Hz, 1H), 8.43 (t, J=6.6 Hz, 1H), 9.81 (d, J=6.2 Hz, 1H).

Analysis calculated for $C_{34}H_{59}N_2O_4I \cdot \frac{1}{2}H_2O$:C 57.9%; H 8.7%; N 4.0%. Found:C 57.41%; H 9.01%; N 4.17%.

We claim:

1. A 2,4-disubstituted derivatives of tetrahydrofuran of formula I

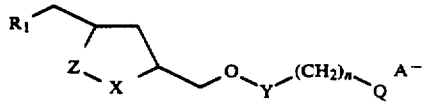

wherein:
  either X is oxygen and Z is $CH_2$ or X is $CH_2$ and Z is oxygen;
  $R_1$ is n-($C_{11}$-$C_{18}$)alkyl, n-($C_{11}$-$C_{18}$)alkoxy or n-($C_{13}$-$C_{18}$)NHC(=O)O—;
  Y is a —C(=O)$NR_4$— group and $R_4$ is hydrogen, $C_1$-$C_4$ acyl, haloacetyl, or $C_1$-$C_4$ alkoxycarbonyl;
  n is an integer from 0 to 4;
  Q is an N-($C_1$-$C_6$)-alkylpyridinium ring connected to the alkylene chain by a ring carbon optionally substituted with a member selected from the group consisting of $C_1$-$C_6$ alkoxy, carbamoyl, $C_1$-$C_6$ hydroxyalkyl or halogen groups;
  $A^-$ is chloride, bromide, iodide, $C_1$-$C_{10}$ alkylsulfonate, or arylsulfonate.

2. A compound according to claim 1 wherein:
  $R_1$ is n-($C_{11}$-$C_{18}$)alkoxy or n-($C_{13}$-$C_{18}$)NHC(=O)O—
  Y is a —C(=O)$NR_4$— group and $R_4$ is acetyl;
  n is 1;
  Q is N-ethyl-2-pyridinium;
  X, Z and $A^-$ are as defined in claim 1.

3. A compound according to claim 2 wherein:
  X is oxygen and Z is $CH_2$; and
  $R_1$, Y, n, Q and $A^-$ are as defined in claim 2.

4. A compound according to claim 3 which is (±)-cis,trans-N-ethyl-2-((((4-hexadecyloxymethyltetrahydrofuran-2-yl)methoxy)carbonyl)amino)methyl)-pyridinium chloride.

5. A compound according to claim 3 which is (±)-cis,trans-N-ethyl-2-((((4-pentadecylaminocarbonyloxymethyltetrahydrofuran-2-yl)methoxy)carbonyl)amino)methyl)pyridinium iodide.

6. A pharmaceutical composition for the treatment of PAF-mediated illnesses in warm-blooded animals comprising an effective amount of a compound of formula I

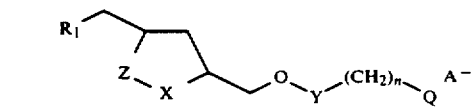

wherein:
  either X is oxygen and Z is $CH_2$ or X is $CH_2$ and Z is oxygen;
  $R_1$ is n-($C_{11}$-$C_{18}$)alkyl, n-($C_{11}$-$C_{18}$)alkoxy or n-($C_{13}$-$C_{18}$)NHC(=O)O—;
  Y is a —C(=O)$NR_4$— group and $R_4$ is hydrogen, $C_1$-$C_4$ acyl, haloacetyl, or $C_1$-$C_4$ alkoxycarbonyl;
  n is an integer from 0 to 4;
  Q is an N-($C_1$-$C_6$)-alkylpyridinium ring connected to the alkylene chain by a ring carbon and which may be further substituted by one or several $C_1$-$C_6$ alkoxy, carbamoyl, $C_1$-$C_6$ hydroxyalkyl or halogen groups;
  $A^-$ is chloride, bromide, iodide, $C_1$-$C_{10}$ alkylsulfonate, or arylsulfonate;
in combination with a pharmaceutically-acceptable carrier or diluent.

7. A method for treating warm-blooded animals suffering of PAF-mediated illnesses which comprises administering an effective amount of a compound of formula I

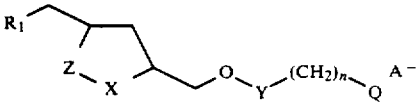

wherein:
  either X is oxygen and Z is $CH_2$ or X is $CH_2$ and Z is oxygen;
  $R_1$ is n-($C_{11}$-$C_{18}$)alkyl, n-($C_{11}$-$C_{18}$)alkoxy or n-($C_{13}$-$C_{18}$)NHC(=O)O—;
  Y is a —C(=O)$NR_4$— group and $R_4$ is hydrogen, $C_1$-$C_4$ acyl, haloacetyl, or $C_1$-$C_4$ alkoxycarbonyl;
  n is an integer from 0 to 4;
  Q is an N-($C_1$-$C_6$)-alkylpyridinium ring connected to the alkylene chain by a ring carbon and which may be further substituted by one or several $C_1$-$C_6$ alkoxy, carbamoyl, $C_1$-$C_6$ hydroxyalkyl or halogen groups;
  $A^-$ is chloride, bromide, iodide, $C_1$-$C_{10}$ alkylsulfonate, or arylsulfonate, in combination with a pharmaceutically-acceptable excipient.

* * * * *